United States Patent
Chatterjee et al.

(10) Patent No.: US 10,040,830 B2
(45) Date of Patent: Aug. 7, 2018

(54) METHODS AND COMPOSITIONS FOR PROTEIN DELIVERY

(71) Applicant: The United States of America, as represented by the Secretary, Dept. of Health and Human Services, Washington, DC (US)

(72) Inventors: Deb Chatterjee, Potomac, MD (US); Stanislaw Jan Kaczmarczyk, Frederick, MD (US)

(73) Assignee: The United States of America, as represented by the Secretary, Dept. of Health and Human Services, Washington, DC (US)

(*) Notice: Subject to any disclaimer, the term of this patent is extended or adjusted under 35 U.S.C. 154(b) by 0 days.

(21) Appl. No.: 15/082,401

(22) Filed: Mar. 28, 2016

(65) Prior Publication Data

US 2016/0199511 A1    Jul. 14, 2016

Related U.S. Application Data

(62) Division of application No. 13/122,513, filed as application No. PCT/US2009/059328 on Oct. 2, 2009, now Pat. No. 9,296,790.

(60) Provisional application No. 61/195,084, filed on Oct. 3, 2008.

(51) Int. Cl.
| | |
|---|---|
| *C07K 14/15* | (2006.01) |
| *C07K 14/005* | (2006.01) |
| *C07K 14/00* | (2006.01) |
| *C07K 14/245* | (2006.01) |
| *C12N 7/00* | (2006.01) |
| *A61K 47/69* | (2017.01) |

(52) U.S. Cl.
CPC ........ *C07K 14/005* (2013.01); *A61K 47/6901* (2017.08); *C07K 14/00* (2013.01); *C07K 14/245* (2013.01); *C12N 7/00* (2013.01); *C07K 2319/09* (2013.01); *C07K 2319/10* (2013.01); *C07K 2319/50* (2013.01); *C07K 2319/705* (2013.01); *C07K 2319/735* (2013.01); *C12N 2740/13043* (2013.01); *C12N 2760/20222* (2013.01); *C12N 2760/20223* (2013.01); *C12N 2810/6072* (2013.01); *C12N 2810/6081* (2013.01)

(58) Field of Classification Search
CPC ............ C07K 14/005; C07K 2319/735; C07K 2319/02; C07K 14/4722; C07K 16/2812; C07K 16/2866; C07K 2319/09; C07K 2319/50; A61K 2039/5258; A61K 2039/622; A61K 39/12; A61K 9/5184; A61K 47/6901; C12Q 1/6897; C12N 2740/11023; C12N 2740/11042
See application file for complete search history.

(56) References Cited

U.S. PATENT DOCUMENTS

| | | | |
|---|---|---|---|
| 5,071,651 | A | 12/1991 | Sabara et al. |
| 5,374,426 | A | 12/1994 | Sabara et al. |
| 5,631,237 | A | 5/1997 | Dzau et al. |
| 6,099,847 | A | 8/2000 | Tobin et al. |
| 6,902,886 | B1 | 6/2005 | Citovsky et al. |
| 9,296,790 | B2 | 3/2016 | Chatterjee et al. |
| 2002/0052040 | A1 | 5/2002 | Hunt |

FOREIGN PATENT DOCUMENTS

| | | |
|---|---|---|
| WO | WO 92/11291 | 7/1992 |
| WO | WO 96/30523 | 10/1996 |
| WO | WO 98/15631 | 4/1998 |
| WO | WO 01/44481 | 6/2001 |
| WO | WO 03/024481 | 3/2003 |
| WO | WO 2005/042695 | 5/2005 |
| WO | WO 2005/115444 | 12/2005 |
| WO | WO 2006/059141 | 6/2006 |
| WO | WO 2007/130330 | 11/2007 |

OTHER PUBLICATIONS

Akkina et al., High-efficiency gene transfer into CD34+ cells with a human immunodeficiency virus type 1-based retroviral vector pseudotyped with vesicular stomatitis virus envelope glycoprotein G., J Virol. Apr. 1996;70(4):2581-5.
Deml et al. "Recombinant HIV-1 Pr55gag virus-like particles: potent stimulators of innate and acquired immune responses," Molecular Immunology, 2005, vol. 42, issue 2, pp. 259-277.
Dunn et al. "Retroviral proteases," Genome Biology, Mar. 2002, vol. 3, (4), pp. 3006.1-3006.7.
Gonzalez-Navajas et al. "Immunomodulatory functions of type 1 interferons," Nature Review/Immunology, col. 12, Feb. 2012, pp. 125-135.
Guibinga et al. "Baculovirus GP64-Pseudotyped HIV-Based Lentivirus Vectors are Stabilized Against Complement Inactivation by Codisplay of Decay Accelerating Factor (DAF) or of a GP64-DAF Fusion Protein," Molecular Therapy, Apr. 2005, vol. 11, No. 4, pp. 645-651.
Haglund et al. "Expression of Human Immunodeficiency Virus Type 1 Gag Protein Precursor and Envelope Proteins from a Vesicular Stomatitis Virus Recombinant: High-Level Production of Virus-like Particles Containing HIV Envelope," Virology, 2000, vol. 268, pp. 112-121.
Hajek et al. "Proteolytic Processing and Assembly of gag and gag-pol Proteins of TED, a Baculovirus-Associated Retrotransposon of the Gypsy Family," Journal of Virology, Nov. 1998, vol. 72, No. 11, pp. 8718-8724.

(Continued)

*Primary Examiner* — Bao Li
(74) *Attorney, Agent, or Firm* — Sheridan Ross P.C.

(57) ABSTRACT

The present invention provides methods and compositions for protein delivery. The invention features virus like particles, methods of making virus like particles and methods of using virus like particles to deliver proteins to a cell, to provide protein therapy and to treat diseases or disorders. The invention also features methods of targeting a protein to a cell, methods of protein therapy and methods of treating diseases or disorders using a TUS protein, a NLS or NES identified from full length TUS.

20 Claims, 35 Drawing Sheets

(56) References Cited

OTHER PUBLICATIONS

Harvey et al. Tetracycline-Inducible Packaging Cell Line for Production of Flavivirus Replicon Particles, Journal of Virology, Jan. 2004, vol. 78, No. 1, pp. 531-538.
Kent et al. "Evaluation of recombinant Kunjin replicon SIV vaccines for protective efficacy in macaques," Virology, May 2008, vol. 374, No. 2, pp. 528-534.
Lewis et al. "Development of an Avian Leukosis-Sarcoma Virus Subgroup A Pseudotyped Lentiviral Vector," Journal of Virology, Oct. 2001, vol. 75, No. 19, pp. 9339-9344.
Luo et al. "Chimeric gag-V3 virus-like particles of human immunodeficiency virus induce virus-neutralizing antibodies," PNAS, Nov. 1992, vol. 89, No. 21, pp. 10527-10531.
Luo et al. "Induction of V3-Specific Cytotoxic T Lymphocyte Responses by HIV gag Particles Carrying Multiple Immunodominant V3 Epitopes of gp 120," Virology, 1998, vol. 240, pp. 316-325.
Mazarakis et al. "Rabies virus glycoprotein pseudotyping of lentiviral vectors enables retrograde axonal transport and access to the nervous system after peripheral delivery," Human Molecular Genetics, 2001, vol. 10, No. 19, pp. 2109-2121.
Mervis et al. "The gag gene products of human immunodeficiency virus type 1: alignment within the gag open reading frame, identification of posttranslational modifications, and evidence for alternative gag precursors." Journal of Virology, 1988, vol. 62 (11 ), pp. 3993-4002.
Michel et al. "Optimisation of secretion of recombinant HBsAg virus-like particles: Impact on the development of HIV-1/HBV bivalent vaccines," Vaccine, 2007, available on line by Aug. 22, 2006, vol. 25, pp. 1901-1911.
Morling et al. "Masking of Retroviral Envelope Functions by Oligomerizing Polypeptide Adaptors," Virology, 1997, vol. 234, pp. 51-61.
Naldini et al. "In Vivo Gene Delivery and Stable Transduction of Nondividing Cells by a Lentiviral Vector," Science, Apr. 1996, vol. 272, pp. 263-267.
Naldini et al. "Efficient transfer, integration, and sustained long-term expression of the transgene in adult rat brains injected with a lentiviral vector," Pro. Natl. Acad. Sci. USA, Oct. 1996, vol. 93, pp. 11382-11388.
Peretti et al: "Cell Death Induced by the Herpes Simplex Virus-1 Thymidine Kinase Delivered by Human Immunodeficiency Virus-1-Based Virus-like Particles", Molecular Therapy, Academic Press, San Diego, CA, US, vo 1 . 12, No. 6, Dec. 1, 2005 (Dec. 1, 2005), pp. 1185-1196.
Perez et al. "The Transmembrane Glycoprotein of Human Immunodeficiency Virus Type 1 Induces Syncytium Formation in the Absence of the Receptor Binding Glycoprotein," Journal of Virology, Jul. 1992, vol. 66, No. 7, pp. 4134-4143.
Smit et al. "Flavivirus Cell Entry and Membrane Fusion," Virus, 2011, vol. 3, pp. 160-171.
Varnavski et al. "Noncytopathic Flavivirus Replicon RNA-Based System for Expression and Delivery of Heterologous Genes," Virology 1999, vol. 255 (2), pp. 366-375.
Wagner et al. "Construction, Expression, and Immunogenicity of Chimeric HIV-1 Virus-like Particles," Virology, 1996, vol. 220, pp. 128-140.
International Search Report prepared by the European Patent Office dated Jun. 9, 2010, for International Application No. PCT/US09/059328.
Official Action for U.S. Appl. No. 13/122,513, dated Aug. 7, 2012 10 pages.
Official Action for U.S. Appl. No. 13/122,513, dated Oct. 11, 2012 17 pages.
Official Action for U.S. Appl. No. 13/122,513, dated Mar. 25, 2013 10 pages.
Official Action for U.S. Appl. No. 13/122,513, dated Jan. 14, 2014 13 pages.
Official Action for U.S. Appl. No. 13/122,513, dated Jul. 7, 2014 7 pages.
Official Action for U.S. Appl. No. 13/122,513, dated Feb. 11, 2015 7 pages.
Official Action for U.S. Appl. No. 13/122,513, dated Jun. 18, 2015 5 pages.
Notice of Allowance for U.S. Appl. No. 13/122,513, dated Nov. 17, 2015 10 pages.
Alefantis et al., "Characterization of a Nuclear Export Signal within the Human T Cell Leukemia Virus Type I Transactivator Protein Tax," The Journal of Biological Chemistry, 2003, vol. 278(24), pp. 21814-21822.
Altschul et al., "Basic Local Alignment Search Tool," Journal of Molecular Biology, 1990, vol. 215, pp. 403-410.
Altschul et al., "Gapped BLAST and PSI-BLAST: a new generation of protein database search programs," Nucleic Acids Research, 1997, vol. 25(17), pp. 3389-3402.
Bogerd et al., Protein Sequence Requirements for Function of the Human T-Cell Leukemia Virus Type 1 Rex Nuclear Export Signal Delineated by a Novel in Vivo Randomization-Selection Assay, Molecular and Cellular Biology, 1996, vol. 16(8), pp. 4207-4214.
Briggs, "Protein Sequence Requirements for Function of the Human T-Cell Leukemia Virus Type 1 Rex Nuclear Export Signal Delineated by a Novel in Vivo Randomization-Selection Assay," Nature Structural & Molecular Biology, 2004, vol. 11(7), pp. 672-675.
Carriere et al., "Sequence Requirements for Encapsidation of Deletion Mutants and Chimeras of Human Immunodeficiency Virus Type 1 Gag Precursor into Retrovirus-Like Particles," Journal of Virology, 1995, vol. 69(4), pp. 2366-2377.
Chauhan et al., "The taming of the cell penetrating domain of the HIV Tat: Myths and realities," Journal of Controlled Release, 2007, vol. 117, pp. 148-162.
Chazal et al., "Virus Entry, Assembly, Budding, and Membrane Rafts," Microbiology and Molecular Biology Reviews, 2003, vol. 67(2), pp. 226-237.
Coskun-Ari et al., "Sequence-specific Interactions in the Tus-Ter Complex and the Effect of Base Pair Substitutions on Arrest of DNA Replication in *Escherichia coli*," The Journal of Biological Chemistry, 1997, vol. 272(42), pp. 26448-26456.
Cyert, "Regulation of Nuclear Localization during Signaling," The Journal of Biological Chemistry, 2001, vol. 276(24), pp. 20805-20808.
Dworetzky et al., "Translocation of RNA-Coated Gold Particles Through the Nuclear Pores of Oocytes," The Journal of Cell Biology, 1988, vol. 106, pp. 575-584.
Facke et al., "A Large Deletion in the Matrix Domain of the Human Immunodeficiency Virus gag Gene Redirects Virus Particle Assembly from the Plasma Membrane to the Endoplasmic Reticulum," Journal of Virology, 1993, vol. 67(8), pp. 4972-4980.
Fischer et al., "The HIV-1 Rev Activation Domain Is a Nuclear Export Signal That Accesses an Export Pathway Used by Specific Cellular RNAs," Cell, 1995, vol. 82, pp. 475-483.
Fornerod et al., "CRM1 Is an Export Receptor for Leucine-Rich Nuclear Export Signals," Cell, 1997, vol. 90, pp. 1051-1060.
Gangeten et al., "Brief expression of a GFPcre fusion gene in embryonic stem cells allows rapid retrieval of site-specific genomic deletions," Nucleic Acids Research, 1997, vol. 25(16), pp. 3326-3331.
Gerace, "Nuclear Export Signals and the Fast Track to the Cytoplasm," Cell, 1995, vol. 82, pp. 341-344.
Gorlich et al., "Nucleocytoplasmic Transport," Science, 1996, vol. 271, pp. 1513-1518.
Gottlieb et al., "Equilibrium, Kinetic, and Footprinting Studies of the Tus-Ter Protein-DNA Interaction," The Journal of Biological Chemistry, 1992, vol. 267(11), pp. 7434-7443.
Gottlinger et al., "Role of capsid precursor processing and myristoylation in morphogenesis and infectiveity of human immunodeficiency virus type 1," PNAS, 1989, vol. 86(15), pp. 5781-5785.
Hong et al., "Assembly-Defective Point Mutants of the Human Immunodeficiency Virus Type 1 Gag Precursor Phenotypically Expressed in Recombinant Baculovirus-Infected Cells," Journal of Virology, 1993, vol. 67(5), pp. 2787-2798.

(56) References Cited

OTHER PUBLICATIONS

Ikuta et al., "Nuclear Localization and Export Signals of the Human Aryl Hydrocarbon Receptor," The Journal of Biological Chemistry, 1998, vol. 273(5), pp. 2895-2904.
Jans et al., "Nuclear targeting signal recognition: a key control point in nuclear transport?," BioEssays 22.6, pp. 532-544.
Jiang et al., "Norwalk Virus Genome Cloning and Characterization," Science, 1990, vol. 250, pp. 1580-1583.
Kalderon et al., "A Short Amino Acid Sequence Able to Specify Nuclear Location," Cell, 1984, vol. 39, pp. 499-509.
Kamada et al., "Structure of a replication-terminator protein complexed with DNA," Nature, 1996, vol. 383, pp. 598-603.
Karlin et al., "Methods for assessing the statistical significance of molecular sequence features by using general scoring schemes," PNAS, 1990, vol. 87, pp. 2264-2268.
Karlin et al., "Applications and statistics for multiple high-scoring segments in molecular sequences," PNAS, 1993, vol. 90, pp. 5873-5877.
Kuempel et al., "Bidirectional Termination of Chromosome Replication in *Escherichia coli*," Moled. Gen. Genet., 1973, vol. 125, pp. 1-8.
Kurisaki et al., "The Mechanism of Nuclear Export of Smad3 Involves Exportin 4 and Ran," Molecular and Cellular Biology, 2006, Voo. 26(4), pp. 1318-1332.
Le et al., "Nuclear targeting determinants of the phage P1 Cre DNA recombinase," Nucleic Acids Research, 1999, vol. 27(24), pp. 4703-4709.
Link et al., "Therapeutic protein transduction of mammalian cells and mice by nucleic acid-free lentiviral nanoparticles," Nucleic Acids Research, 2006, vol. 34(2), e16, pp. 1-10.
Masters et al., "Evidence for the Bidirectional Replication of the *Escherichia coli* Chromosome," Nature New Bioology, 1971, vol. 232, pp. 137-140.
Matsui et al., "The Isolation and Characterization of a Norwalk Virus-specific cDNA," Journal of Clinical Investigation, 1991, vol. 87, pp. 1456-1461.
Moll et al., "Designed heterodimerizing leucine zippers with a range of pIs and stabilities up to 10-15 M," Protein Science, 2001, vol. 10, pp. 649-655.
Mulugu et al., "Mechanism of termination of DNA replication of *Escherichia coli* involves helicase-contrahelicase interaction," PNAS, 2001, vol. 98(17), pp. 9569-9574.
Murriel et al., "Influence of protein transduction domains on intracellular delivery of macromolecules," Expert Opinion on Drug Delivery, 2006, vol. 3(6), pp. 739-746.
Newmeyer et al., "Nuclear Import Can Be Separated into Distinct Steps in Vitro: Nuclear Pore Binding and Translocation," Cell, 1988, vol. 52, pp. 641-653.
Neylon et al., "Interaction of the *Escherichia coli* Replication Terminator Protein (Tus) with DNA: A Model Derived from DNA-Binding Studies of Mutant Proteins by Surface Plasmon Resonance," Biochemistry, 2000, vol. 39, pp. 11989-11999.
Neylon et al., Replication Termination in *Escherichia coli*: Structure and Antihelicase Activity of the Tus-Ter Complex, Microbiology and Molecular Biology Reviews, 2005, vol. 69(3), pp. 501-526.
Owais et al., "Liposome-mediated cytosolic delivery of macromolecules and its possible use in vaccine development," European Journal of Biochemistry, 2000, vol. 267, pp. 3946-3956.
Patel et al., "Natively Unfolded Nucleoporins Gate Protein Diffusion across the Nuclear Pore Complex," Cell, 2007, vol. 129, pp. 83-96.
Peitz et al., "Ability of the hydrophobic FGF and basic TAT peptides to promote cellular uptake of recombinant Cre recombinase: A tool for efficient genetic engineering of mammalian genomes," PNAS, 2002, vol. 99(7), pp. 4489-4494.
Pelczar et al., "Agrobacterium proteins VirD2 and VirE2 mediate precise integration of synthetic T-DNA complexes in mammalian cells," European Molecular Biology Organization, 2004, vol. 5(6), pp. 632-637.
Richardson et al., "Nuclear Protein Migration Involves Two Steps: Rapid Binding at the Nuclear Envelope Followed by Slower Translocation through Nuclear Pores," Cell, 1988, vol. 52, pp. 655-664.
Robbins et al., "Two Interdependent Basic Domains in Nucleoplasmin Nuclear Targeting Sequence: Identification of a Class of Bipartite Nuclear Targeting Sequence," Cell, 1991, vol. 64, pp. 615-623.
Royer et al., "Expression and Extracellular Release of Human Immunodeficiency Virus Type 1 Gag Precursors by Recombinant Baculovirus-Infected Cells," Journal of Virology, 1992, vol. 66(5), pp. 3230-3235.
Sasnauskas et al., "Generation of Recombinant Virus-Like Particles of Human and Non-Human Polyomaviruses in Yeast *Saccharomyces cerevisiae*," Intervirology, 2002, vol. 45, pp. 308-317.
Sasnauskas et al., "Yeast Cells Allow High-Level Expression and Formation of Polyomavirus-Like Particles," Biological Chemistry, 1999, vol. 380, pp. 381-386.
Schwarze et al., "Protein transduction: unrestricted delivery into all cells?," Cell Biology, 2000, vol. 10, pp. 290-295.
Skokotas et al., "Mutations in the *Escherichia coli* Tus Protein Define a Domain Positioned Close to the DNA in the Tus-Ter Complex," The Journal of Biological Chemistry, 1995, vol. 270(52), pp. 30941-30948.
Spearman et al., "Identification of Human Immunodeficiency Virus Type 1 Gag Protein Domains Essential to Membrane Binding and Particle Assembly," Journal of Virology, 1994, vol. 68(5), pp. 3232-3242.
Twomey et al., "Structure and immunogenicity of experimental foot-and-mouth disease and poliomyelitis vaccines," Vaccine, 1995, vol. 13(16), pp. 1603-1610.
Ulrich et al., "Core Particles of Hepatitis B Virus as Carrier for Foreign Epitopes," Advances in Virus Research, 1998, vol. 50, pp. 141-182.
Warnes et al., "Expression of the measles virus nucleoprotein gene in *Escherichia coli* and assembly of nucleocapsid-like structures," Gene, 1995, vol. 160, pp. 173-178.
Wilk et al., "Organization of Immature Human Immunodeficiency Virus Type 1," Journal of Virology, 2001, vol. 75(2), pp. 759-771.
International Preliminary Report on Patentability for International (PCT) Patent Application No. PCT/US2009/059328, dated Apr. 14, 2011, 11 pages.
Advisory Action for U.S. Appl. No. 13/122,513, dated Oct. 4, 2013 3 pages.
Advisory Action for U.S. Appl. No. 13/122,513, dated Sep. 19, 2014 4 pages.
Advisory Action for U.S. Appl. No. 13/122,513, dated Dec. 26, 2014 3 pages.
Advisory Action for U.S. Appl. No. 13/122,513, dated Sep. 30, 2015 4 pages.

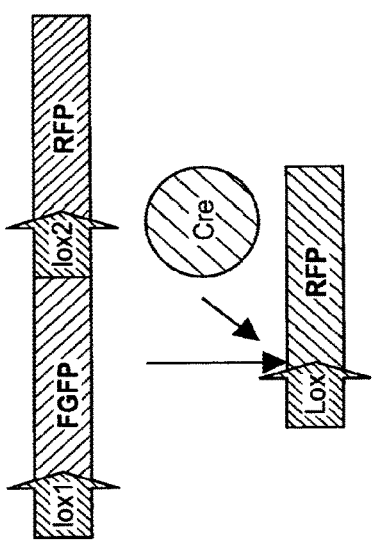
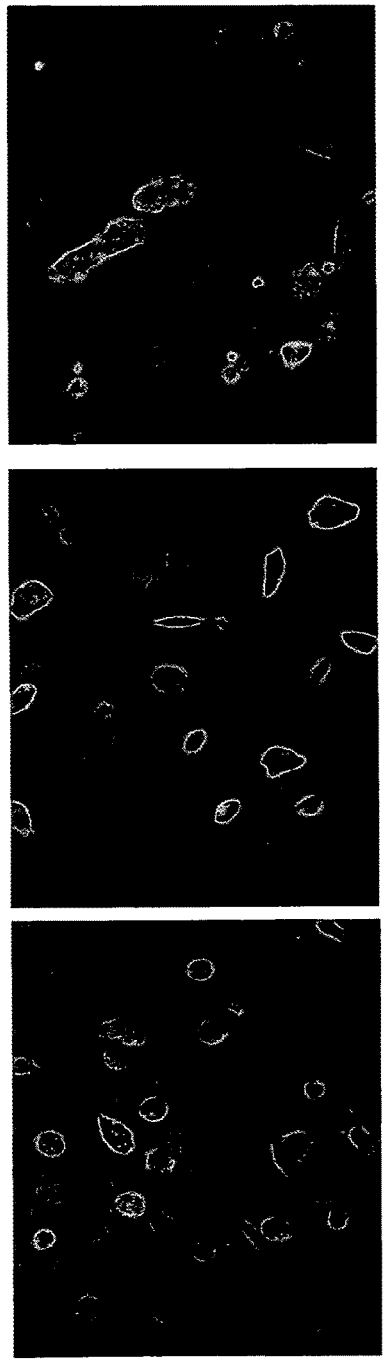
FIG. 1C
A -- non transduced cells
B -- cells transduced with VLP containing GAG-Cre
C -- cells transduced with VLP containing GAG-Cre and pseudotyped with VSV-g envelope

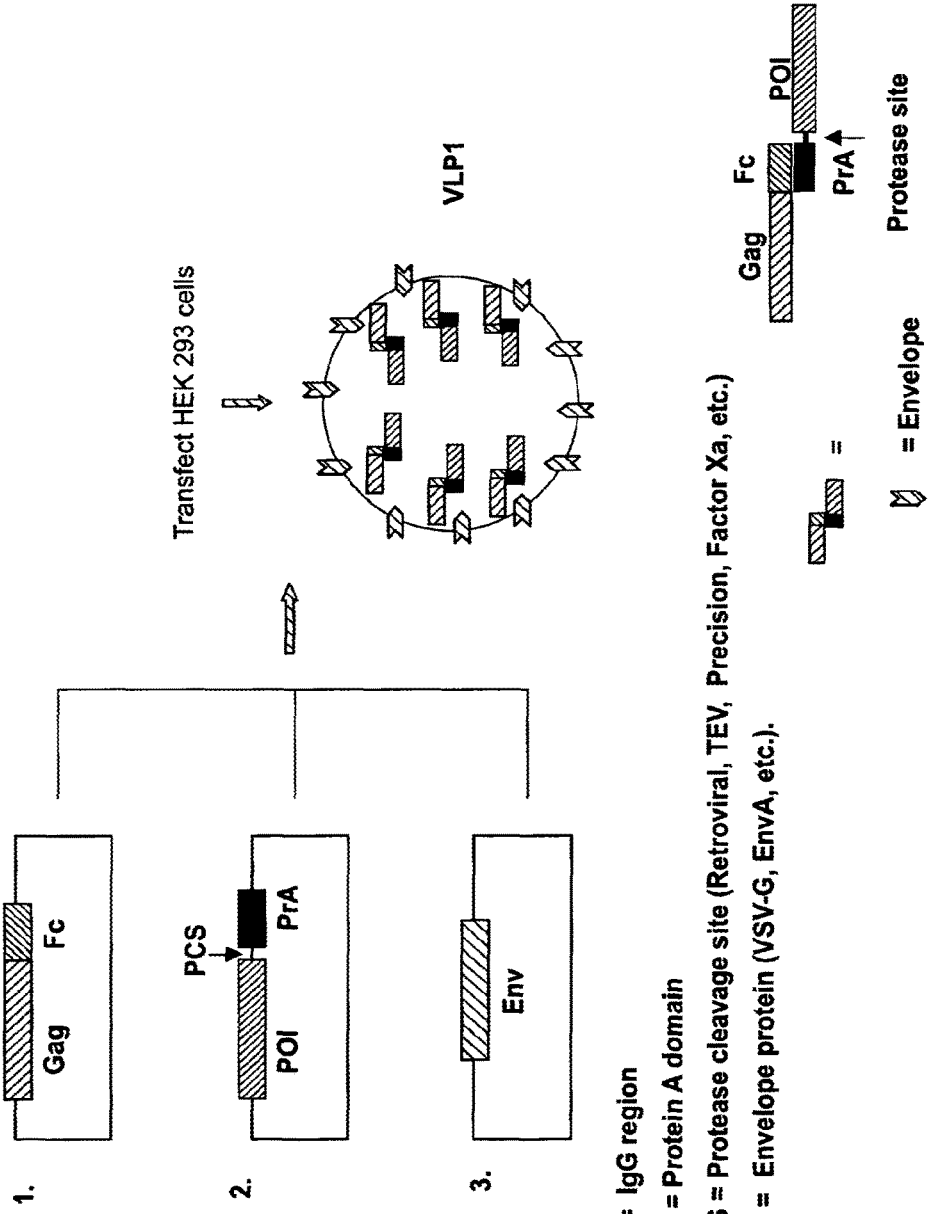

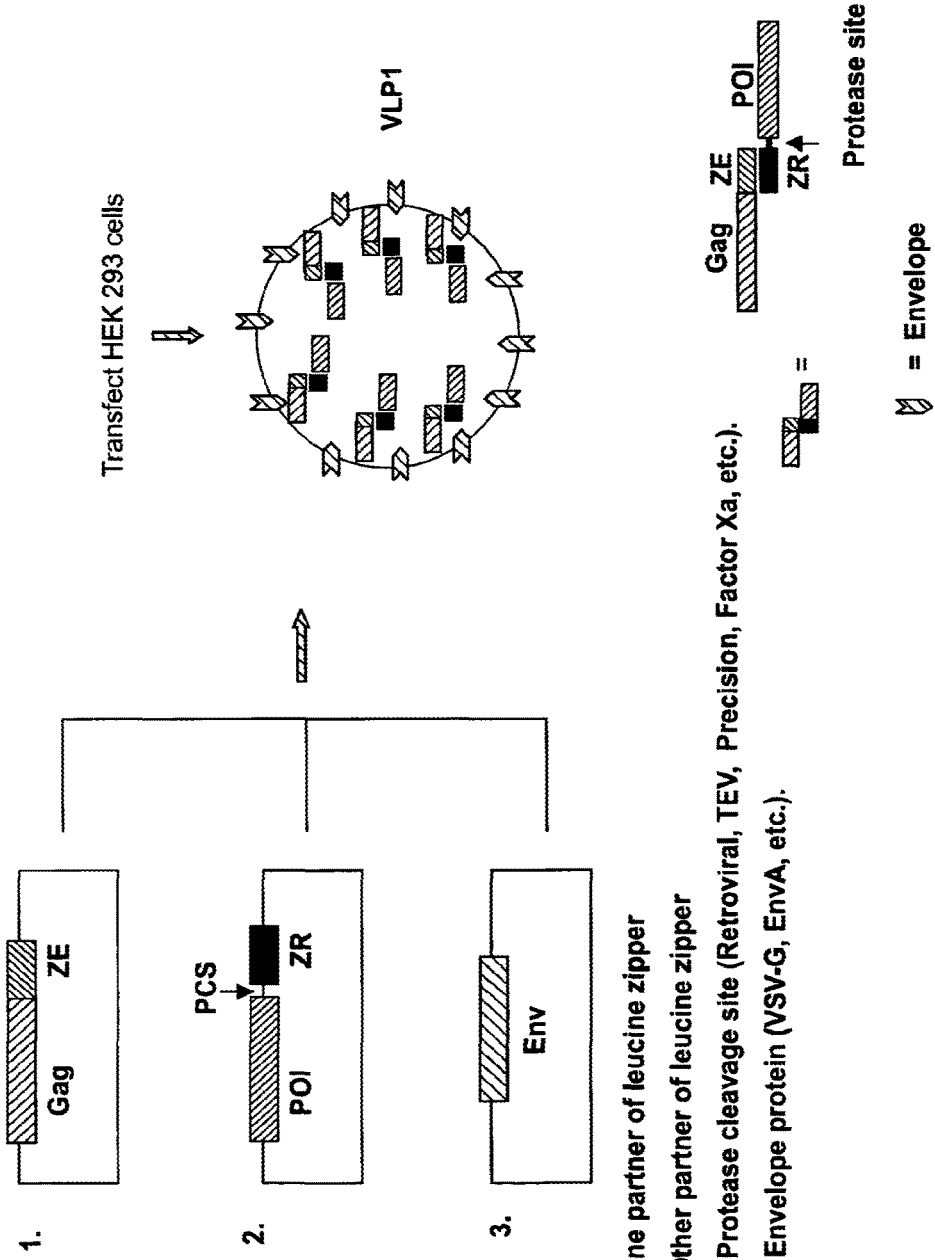

VLPs needed to remove protein of interest from Gag fusion
A. VLP made with Gag-ZE (VLP1)
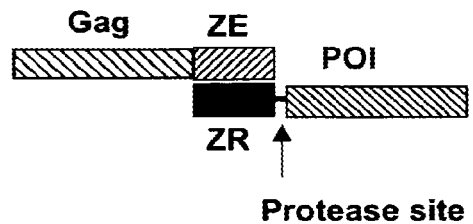
B. VLP made with Gag-Fc of IgG (VLP1)
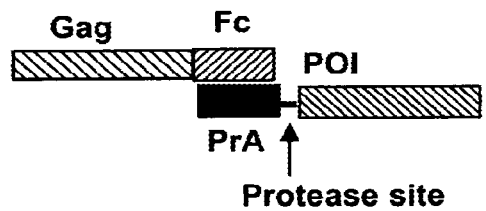
C. VLP made with Gag-Protease (VLP2)
FIG. 3C

Simultaneous Transduction of Recipient cells with VLP 1 and VLP2
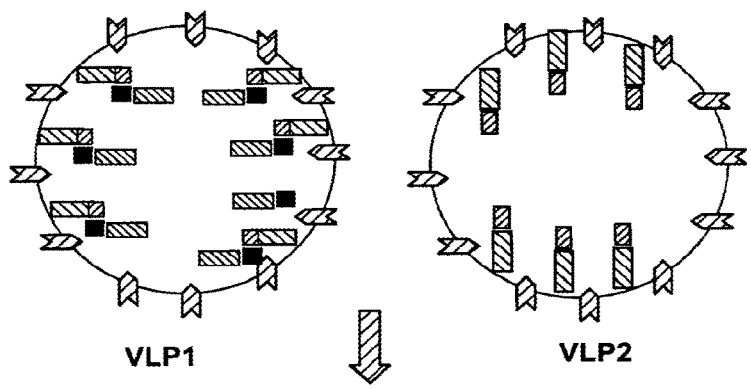
VLP1　　　　　　　　VLP2
Transduce target cell line containing respective receptor for the envelope in the VLP
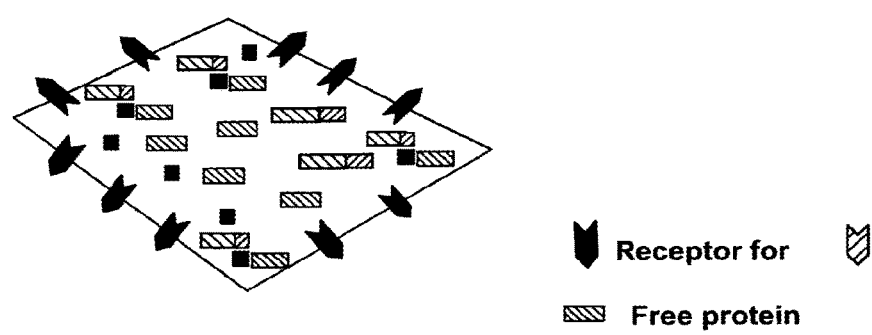
▼ Receptor for ⬠
▨ Free protein
FIG. 3E

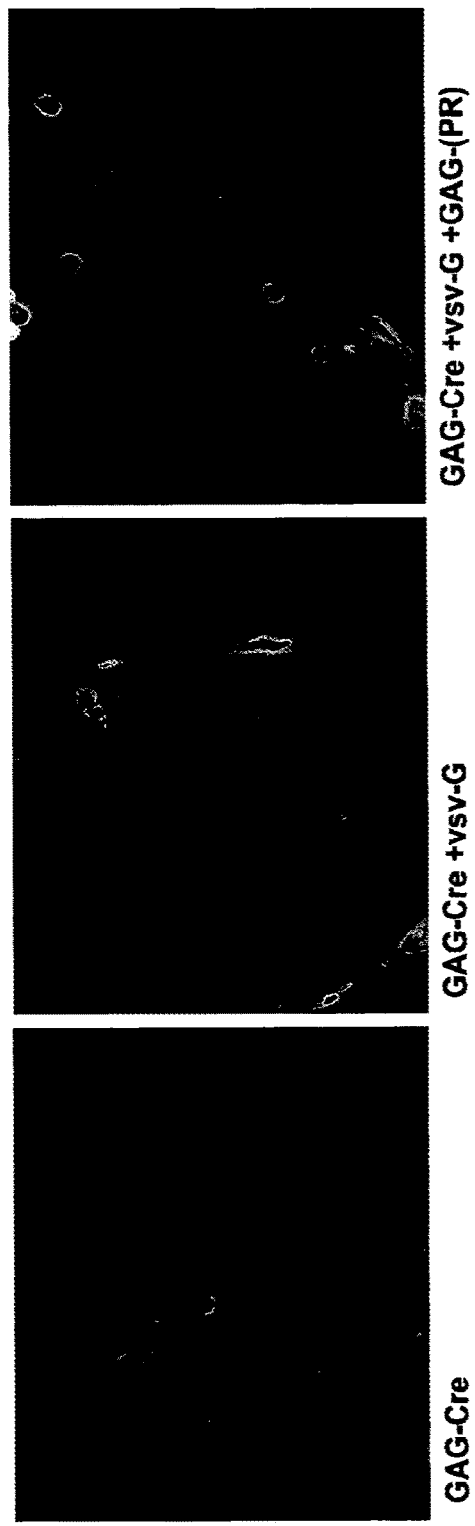

Generation of VLPs to deliver cytotoxic enzymes consisting of FCY-Fur and VSV-G envelope

FIG. 9

Killing of PC3 (prostate cancer cell line) with VLP containing FCY-FUR in the presence of 5FC

VLP containing POI pseudotyped with VSV-GC2 (fusion) and NA-Ligand (Target)

FIG. 16

In this configuration peptide ligand (target) is expressed on VPLs surface as fusion, Hemmagglutinin-(HA)-Ligand protein.

FIG. 17

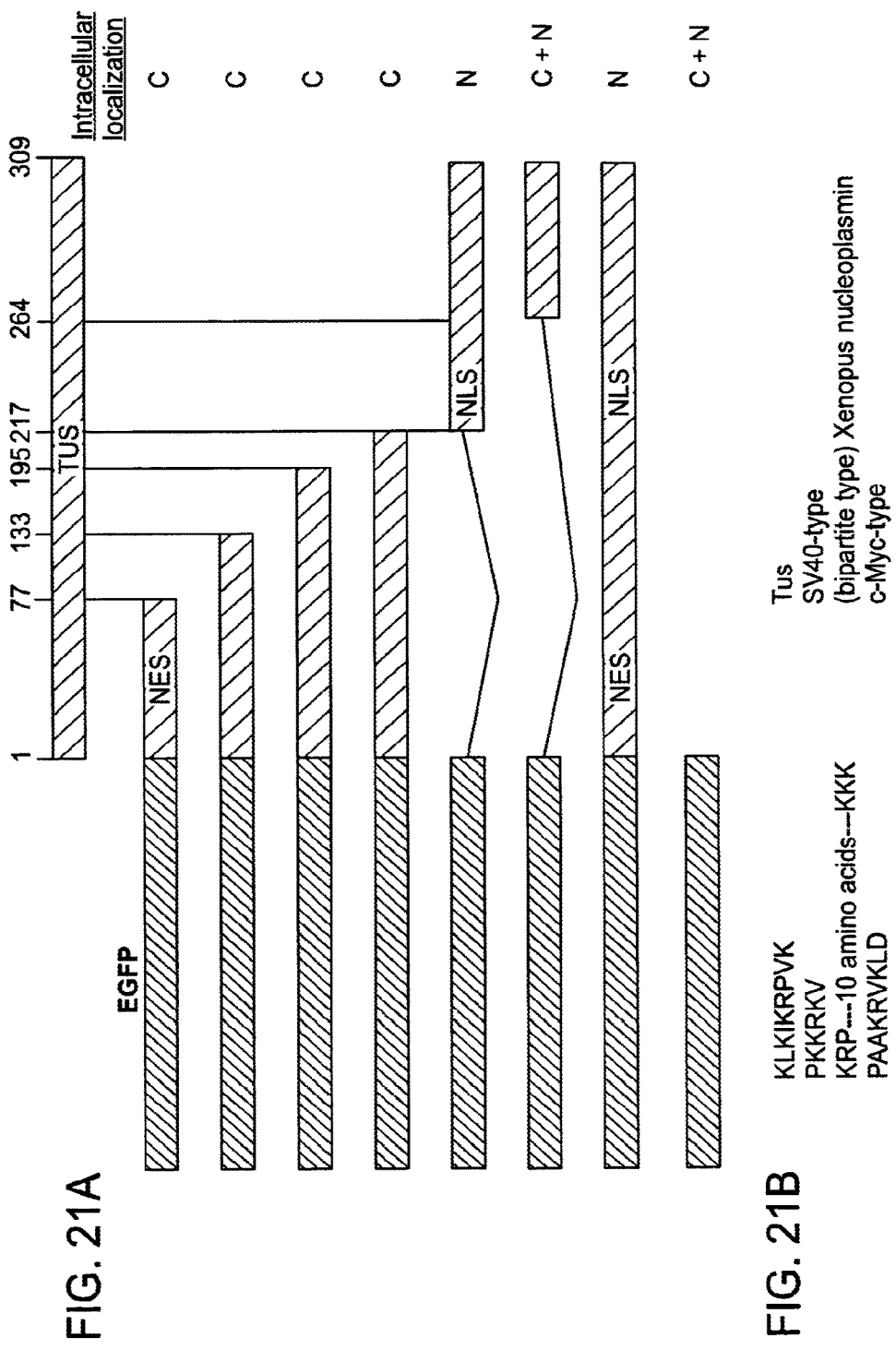

|  |  | NES |
|---|---|---|
| 1 ⊢————————————————⊣ 77 | Yes |
| 1 ⊢————————————⊣ 41 | Yes |
| 1 ⊢——————————⊣ 30 | No |
| 27 ⊢————————⊣ 41 | No |
| 22 ⊢—————————⊣ 41 | No |
| 21 ⊢—————————⊣ 40 | No |
| 21 ⊢—————————⊣ 41 | Yes |

LAIFAAHLEQHKLLVARVFSL

| LAIFAAHLEQHKLLVARVFSL | Tus |
| LQLPPLERLTL | Rev HIV |
| LALKLAGLDIN | PKI |
| MFRELNEALELK | Human p53 |

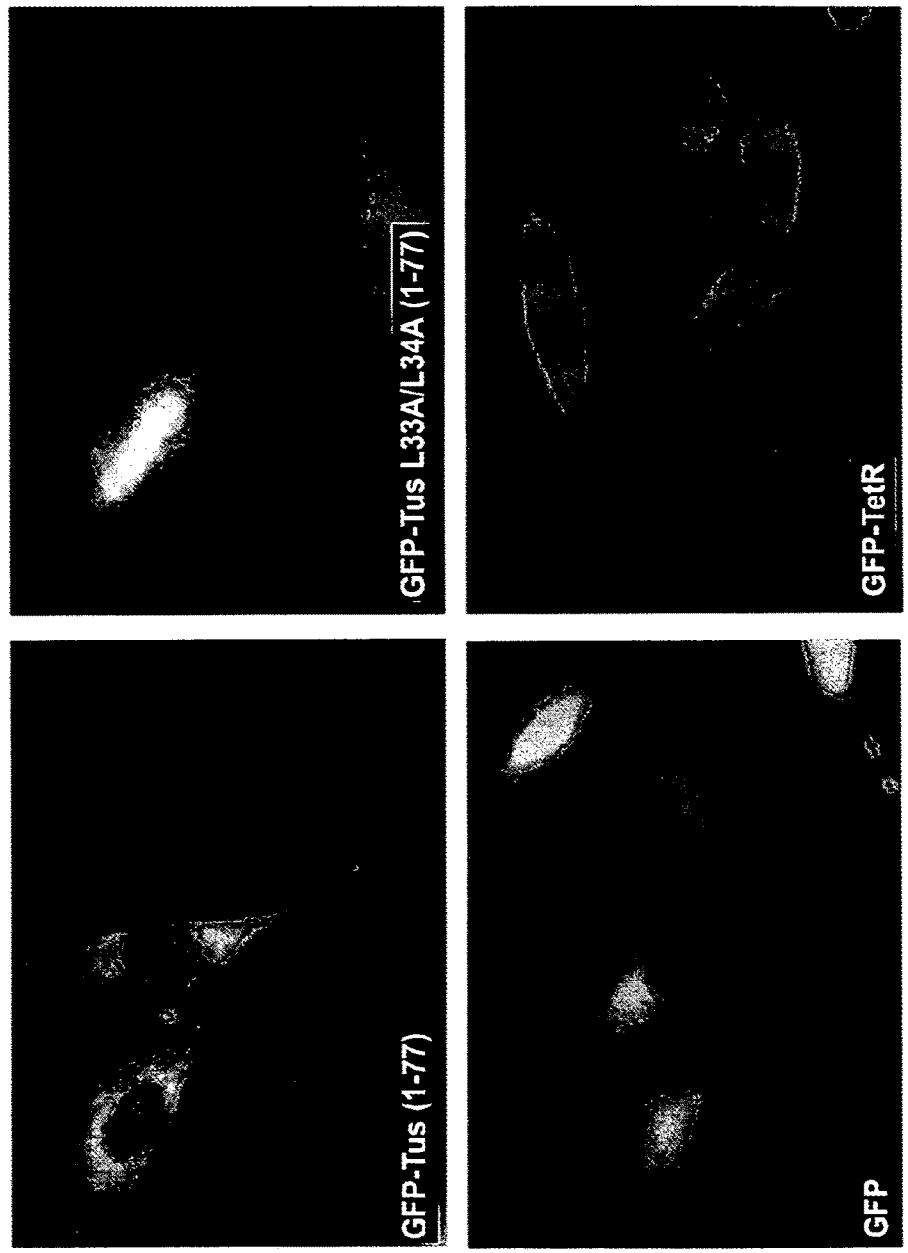

METHODS AND COMPOSITIONS FOR PROTEIN DELIVERY

CROSS-REFERENCE TO RELATED APPLICATION

This application is a divisional application of U.S. patent application Ser. No. 13/122,513, filed Apr. 4, 2011, which is a 35 U.S.C. § 371 U.S. national entry of International Application PCT/US2009/059328 (WO 2010/040023) having an International filing date of Oct. 2, 2009 which claims the benefit of U.S. Provisional Application No. 61/195,084, filed on Oct. 3, 2008, the entire contents of which are incorporated herein by reference.

STATEMENT OF RIGHTS TO INVENTIONS MADE UNDER FEDERALLY SPONSORED RESEARCH

This project has been funded in whole or in part with Federal funds from the National Cancer Institute, National Institutes of Health, under Contract No. NO1-CO-12400. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan.22, 2013, is named 69949479.txt and is 9,786bytes in size.

BACKGROUND OF THE INVENTION

Protein delivery to cells, for example protein delivery for therapeutic purposes, or gene therapy, is typically achieved by one of two approaches to deliver of the therapeutic sequence. One approach uses naked nucleic acid or non-viral vectors Another approach uses viral vectors. Viral vectors can be non-integrative, like adenovirus (Ad) or herpesvirus (HSV), or integrative, like adeno-associated virus (AAV) and retroviruses (e.g. MLV). In the case of Ad and HSV the expression of the therapeutic gene is only transient. In the case of integrative vectors, retroviruses or AAV, there is a long-term (and theoretically cell-life time) expression.

These gene therapy approaches have several drawbacks, including transfer efficiency or oncogenic integration events. Viral vectors inevitably induce neutralizing antibodies or meet pre-existing antibodies in their hosts and this limits the efficiency of gene transfer and the life-time of transduced cells. All viral vectors, even replication-defective ones, have the theoretical possibility to revert back to a replicative form, and/or to recombine with another virus of the same or related family present at the same time in the same host. In addition, the viral genome may insert itself into an essential region causing other problems. Thus, transfer of such material is associated with biological risks and thus requires careful consideration of bio safety.

To address these issues safer and more efficient synthetic vectors for nucleic acid transfer are needed.

Virus Like Particles (VLPs) are structures resembling a virus particle but devoid of the viral genome. Accordingly they are incapable of replication and devoid of pathogenicity. A VLP typically comprises at least one type of structural protein from a virus.

In most cases this protein will form a proteinaceous capsid (e.g. VLPs comprising a retrovirus, adenovirus or bacteriophage structural protein). In some cases the capsid will also be enveloped in a lipid bilayer originating from the cell from which the assembled VLP has been released.

VLPs are typically formed when a gene encoding a viral structural protein is overexpressed in a host cell in isolation from other viral genes. In the cytosol, the structural proteins assemble into the VLP in a process analogous to the process in which a bona fide virus particle assembles. Formation of VLPs results in their release from the host cell. In most cases, VLPs are used for making antibodies using only GAG or structural proteins. It might also possible to assemble VLPs in vitro. Enveloped virus-like particles can be engineered to be fusogenic and thus capable of delivering both membrane bound and non-membrane-bound proteins to cells.

The present invention makes use of virus-like particles (VLPs) as delivery vehicles for proteins to cells.

There is a need in the art for safer, more effective delivery and targeting of protein to cells, which is satisfied by the present invention.

SUMMARY

The present invention is based on novel compositions and methods for delivery of proteins to cells, for example, for therapeutic methods. The present invention is based on the finding that a protein of interest can be delivered to a cell as fused or an unfused protein. In particular, the present invention has shown that a virus like particle (VLP) was made with two GAG-fusion (GAG-protein of interest and GAG-Protease) to deliver the protein of interest to the cell as an unfused protein. This finding is important because the GAG-protein of interest may not be active in some cases, while the protein of interest in its unfused form, after delivery to the cell, will be active.

In a first aspect, the invention provides a virus-like particle (VLP) comprising a first polypeptide, comprising one or more viral structural proteins, or fragments or derivatives thereof, linked to a protein of interest; and a second polypeptide comprising a fusogenic protein.

In another aspect, the invention provides a virus-like particle (VLP) comprising a first polypeptide, comprising one or more viral structural proteins, or fragments or derivatives thereof, linked to a protein of interest; and a second polypeptide comprising one or more viral structural proteins, or fragments or derivatives thereof, linked to a protease.

In one embodiment, the VLP further comprises a fusogenic protein.

In another embodiment, the fusogenic protein is selected from the group consisting of influenza haemagglutinin (HA), the respiratory syncytial virus fusion protein, the E proteins of tick borne encephalitis virus and dengue fever virus, the E1 protein of Semliki Forest virus, the G proteins of rabies virus and vesicular stomatitis virus and baculovirus gp64, neuroamidase (NA) or fragments or derivatives thereof.

In another embodiment, the fusogenic protein is an envelope glycoprotein, or fragment or derivative thereof.

In another further embodiment, the envelope glycoprotein is from a RNA virus or a retrovirus, or fragments or derivatives thereof.

In still another embodiment, the envelope glycoprotein is Vesicular Stomatitis Virus (VSV–G) or Avian sarcoma-leukosis virus envelope A (EnvA).

In another aspect, the present invention provides a VLP comprising a first polypeptide, comprising one or more viral structural proteins, or fragments or derivatives thereof, linked to a protein of interest; and a second polypeptide comprising one or more viral structural proteins, or fragments or derivatives thereof, linked to a protease, and VSV-G glycoprotein.

In one embodiment, the VSV-G comprises an alteration. In another embodiment, the alteration is a deletion, substitution or addition. In a further related embodiment, the alteration is a substitution of a second amino acid (F) of mature VSV-G glycoprotein to cysteine 2 (Cys2). For example, the substitution may comprise a change in mkellylaflfigvncKFTIVF . . . to . . . mkellylaflfigvncKCTIVF (SEQ ID NOS 4 and 5, respectively, in order of appearance), where the lower case amino acids represent the signal peptide sequence and the mature peptide sequence is shown in bold.

In another embodiment, the protein of interest is selected from the group consisting of cytotoxic enzymes, interferons, tumor suppressors, proteases, recombinases, hormones, and stem cell transcription factors. In another related embodiment, the cytotoxic enzyme converts a prodrug into an active drug. In still another further embodiment, the cytotoxic enzyme is selected from the group consisting of a yeast cytosine deaminase/uracil phospho-ribosyltransferase fusion (Fcy::Fur), E. coli CodA gene, and a Herpes thymidine kinase (HSVtk) gene.

In one embodiment of the above aspects, the one or more viral structural proteins are from a virus from a family selected from the group consisting of Retroviridae, Coronaviridae, Herpesviridae, Hepadnaviridae, and Orthomyxoviridae. In another further related embodiment, the one or more viral structural proteins is a Retroviridae viral protein from the Human Immunodeficiency Virus.

In a particular embodiment, the structural protein, or fragments or derivative thereof, is a GAG protein.

In another aspect, the invention features a VLP comprising a GAG protein, or fragments or derivatives thereof, linked to a protein of interest; and a second polypeptide comprising a GAG protein, or fragments or derivatives thereof, linked to a protease, and a VSV-G glycoprotein.

In one embodiment of the above aspects, the GAG protein, or fragments or derivatives thereof is capable of forming an enveloped VLP.

In preferred embodiment, the VLP pf any one of the above aspects further comprises a a protease cleavage site linked to the protein of interest.

In another embodiment, the present invention features a pharmaceutical composition comprising: the VLP of any one of the above aspects, and an acceptable pharmaceutical carrier.

In another aspect, the present invention features a VLP comprising a GAG protein, or fragments or derivatives thereof, linked to a protein of interest; and a second polypeptide comprising a GAG protein, or fragments or derivatives thereof, linked to a protease, and a VSV-G glycoprotein.

In one embodiment of any one of the above aspects, the VLP comprises at least 1000-4000 copies of the viral structural protein.

In one embodiment, the first plasmid further comprises nucleic acids encoding a protease cleavage site. In a related embodiment, the protease cleavage site is linked to the protein.

In a related embodiment, the protease cleavage site is a tobacco etch virus (TEV) protease cleavage site.

In a further embodiment, the VLP of the above mentioned aspects further comprises a binding domain.

In a related embodiment, the binding domain is linked to the one or more viral structural proteins.

In one embodiment of any one of the above aspects, the binding domain is a component of a leucine zipper.

In another embodiment, the component of the leucine zipper is ZE or ZR. In a further embodiment of the above aspects, the binding domain is IgGFc.

In another related embodiment of the above aspects, the link is a conjugation.

In another embodiment, the present invention features a nucleotide sequence encoding the VLP of the above mentioned aspects.

The invention also features in another embodiment a method for producing the VLP of any one of the aspects described herein comprising preparing a first plasmid comprising one or more genes encoding one or more viral structural proteins, or fragments or derivatives thereof, linked to a gene encoding a protein of interest; and a second polypeptide comprising one or more genes encoding one or more viral structural proteins, or fragments or derivatives thereof, linked to a gene encoding a protease; preparing a second plasmid comprising a gene encoding a fusogenic protein; contacting a target cell with the first plasmid and the second plasmid, where the expressed proteins are capable of forming VLPs; and purifying the VLPs, thereby producing the VLP.

In one embodiment, the first polypeptide and the second polypeptide are packaged at a molar ratio of 10:1, 9.9:1, 9.8:1, 9.7:1, 9.6:1, 9.5:1, 9.4:1, 9.3:1, 9.2:1, 9.0:1, 8.9:1, 8.8:1, 8.7:1, 8.6:1, 8.5:1, 8.4:1, 8.3:1, 8.2:1, 8.1:1, 8.0:1, 7.9:1, 7.8:1, 7.7:1, 7.6:1, 7.5:1, 7.4:1, 7.3:1, 7.2:1, 7.1:1, 7.0:1, 6.9:1, 6.8:1, 6.7:1, 6.6:1, 6.5:1, 6.4:1, 6.3:1, 6.2:1, 6.1:1, 6.0:1, 5.9:1, 5.8, 5.7:1, 5.6:1, 5.5:1, 5.4:1, 5.3:1, 5.2:1, 5.1:1, 5.0:1, 4.9:1, 4.8:1, 4.7:1, 4.6:1, 4.5:1, 4.4:1, 4.3:1, 4.2:1, 4.1:1, 4.0:1, 3.9:1, 3.8:1, 3.7:1, 3.6:1, 3.5:1, 3.4:1, 3.3:1, 3.2:1, 3.1:1, 3.0:1, 4.9:1, 2.8:1, 2.7:1, 2.6:1, 2.5:1, 2.4:1, 2.3:1, 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1.

In one embodiment, the contacting is a method of cell transfection.

In another embodiments, the target cell is growing in a culture medium.

In a related embodiment, the target cell is growing in a culture medium for 24 hours. In another related embodiment, the target cell is growing in a culture medium for 48 or more hours.

In another embodiment, the VLP is collected from the culture medium.

In one embodiment, the first plasmid further comprises nucleic acids encoding a protease cleavage site. In a related embodiment, the protease cleavage site is linked to the protein.

In a related embodiment, the protease cleavage site is a tobacco etch virus (TEV) protease cleavage site.

In another embodiment, the invention features a method of treating or preventing a disease or a disorder in a subject, comprising administering to a subject the VLP of any one of the above aspects, or the pharmaceutical composition of the aspects described herein.

In one embodiment, the disease or disorder is selected from the group consisting of: cancer, metabolic diseases, inflammatory diseases, cardiovascular diseases, aging diseases, and diseases of abnormal cell proliferation.

In another embodiment, the invention features a kit comprising the VLP of any one of the aspects described herein, and a host cell line.

The invention features a kit comprising a VLP of any one of the above embodiments, and a host cell line, and instructions for making a VLP.

The invention features a kit comprising a VLP of any one of the above embodiments, and a host cell line, and instructions for use in treating or preventing a disease or a disorder in a subject.

In another aspect, the invention features a kit comprising a first plasmid comprising one or more genes encoding one or more viral structural proteins, or fragments or derivatives thereof, linked to a gene encoding a protein of interest; and a second plasmid comprising one or more genes encoding one or more viral structural proteins, or fragments or derivatives thereof, linked to a gene encoding a protease, and instructions for use for making a VLP.

In one embodiment, the kit further comprises a plasmid comprising a gene encoding a fusogenic protein.

In another aspect, the invention features a method of targeting one or more proteins to a cell comprising contacting the cell with a nucleic acid molecule that comprises a sequence encoding at least a portion of SEQ ID NO: 1 or SEQ ID NO: 2, and a sequence encoding a protein of interest, thereby targeting one or more proteins to a cell.

In one embodiment, the protein is targeted to the nucleus of the cell.

In another aspect, the invention features a method of transporting one or more proteins into a cell comprising contacting the cell with a nucleic acid molecule that comprises a sequence encoding at least a portion of SEQ ID NO: 1 or SEQ ID NO: 2 and a sequence encoding a protein of interest, thereby transporting one or more proteins into the cell.

In one embodiment, the protein is transported to the nucleus.

In another embodiment of the above aspects, the cell is in vitro or in vivo.

In another aspect, the invention features a method of providing protein therapy to a target cell comprising contacting the cell with a nucleic acid molecule that comprises a sequence encoding at least a portion of SEQ ID NO: 1 or SEQ ID NO: 2, and a sequence encoding a protein of interest, thereby providing protein therapy to the target cell.

In one embodiment, the protein of interest is targeted to the nucleus of the cell.

In another aspect, the invention features a method of providing protein therapy to a target cell comprising contacting the cell with a nucleic acid molecule that comprises a sequence encoding at least a portion of SEQ ID NO: 3 and a sequence encoding a protein of interest, thereby providing protein therapy to the target cell.

In one embodiment, the protein of interest is exported from the nucleus.

In another embodiment, the protein of interest is targeted to the cytoplasm of the cell.

In another aspect, the invention features a method for treating or preventing a disease or disorder in a subject comprising contacting the cell with a nucleic acid molecule that comprises a sequence encoding at least a portion of SEQ ID NO: 1 or SEQ ID NO: 2 and a sequence encoding a protein of interest, thereby treating or preventing a disease or disorder in a subject.

In another aspect, the invention features a method for treating or preventing a disease or disorder in a subject comprising contacting the cell with a nucleic acid molecule that comprises a sequence encoding at least a portion of SEQ ID NO: 3 and a sequence encoding a protein of interest, thereby treating or preventing a disease or disorder in a subject.

In another aspect, the invention features a plasmid comprising a nucleic acid molecule that comprises a sequence encoding at least a portion of SEQ ID NO: 1 and a sequence encoding a protein of interest.

In another aspect, the invention features a plasmid comprising a nucleic acid molecule that comprises a sequence encoding at least a portion of SEQ ID NO: 2 and a sequence encoding a protein of interest.

In another aspect, the invention features a plasmid comprising a nucleic acid molecule that comprises a sequence encoding at least a portion of SEQ ID NO: 3 and a sequence encoding a protein of interest.

In one embodiment of the above aspects, the plasmid comprises a promoter suitable for expression in a mammalian cell.

In another aspect, the invention features a cell comprising the plasmid of the above aspects. In one embodiment, the cell is in vitro or in vivo.

In one embodiment of the above aspects, the invention features a kit comprising any one of the plasmid of any one of the above aspects, and instructions for use in treating a disease or disorder.

In one embodiment of the above aspects, the invention features a kit comprising any one of the plasmid of any one of the above aspects, and instructions for use in providing protein therapy to a target cell.

In another embodiment of the above aspects, the invention features a kit comprising any one of the plasmid of any one of the above aspects, and instructions for use in transporting one or more proteins into a cell.

In another aspect, the invention features an isolated polypeptide comprising the amino acid sequence of SEQ ID NO: 1.

In another aspect, the invention features an isolated polypeptide comprising the amino acid sequence of SEQ ID NO: 2.

In one embodiment, the polypeptide comprises a nuclear localization signal.

In another embodiment, the nuclear localization signal comprises amino acids 218-264 of SEQ ID NO: 1.

In another further embodiment, the polypeptide comprises a nuclear export signal.

In still another embodiment, the nuclear export signal comprises amino acids 1-217 of SEQ ID NO: 1.

In another embodiment, the invention features a kit comprising the isolated polypeptide of the above aspects, and instructions for its use as a nuclear localization signal.

In another embodiment, the invention features a kit comprising the isolated polypeptide of the above aspects, and instructions for its use as a nuclear export signal.

Other aspects of the invention are described infra.

shows plasmid components needed to make VLP2. (*c*) shows simultaneous transduction of recipient cells with VLP1 and VLP2. The target cells or organs are simultaneously transduced with both VLPs (VLP1 and VLP2) resulting in delivery of therapeutic protein processed in target site by the specific protease.

FIGS. 3 (*a-e*) are schematics showing various VLP modules. (*a*) shows plasmid components needed to make VLP1 with PrA and Fc of IgG. (*b*) shows plasmid components needed to make VLP1 with ZE and ZR. (*c*) shows VLPs needed to remove protein of interest from Gag fusion. (*d*) shows plasmid components needed to make VLP2. (*e*) shows simultaneous transduction of recipient cells with VLP1 and VLP2.

FIGS. 4 (*a* and *b*) are schematics. (*a*) shows generation of the GAG–Cre recombinase VLP used for in vivo studies. (*b*) is a schematic of the in vivo studies using VLPs.

FIG. 5 shows GAG–Cre fusion and processed Cre recombinase activity in PC3 cell line. The expression of the POI as part of GAG-fusion can sometimes compromise biological activity of POI. In order to maintain biological activity of POI, chimeric VLPs have been generated consisting of GAG-POI and GAG-protease co-packaged at 10:1 molar ratio to the same VLP. Upon maturation of VLPs, protease cleaves all GAG components resulting in the generation of native POI. In these VLPs the cargo protein was successfully processed and was delivered to its target—cellular nucleus as biologically active Cre recombinase.

Figure 6:
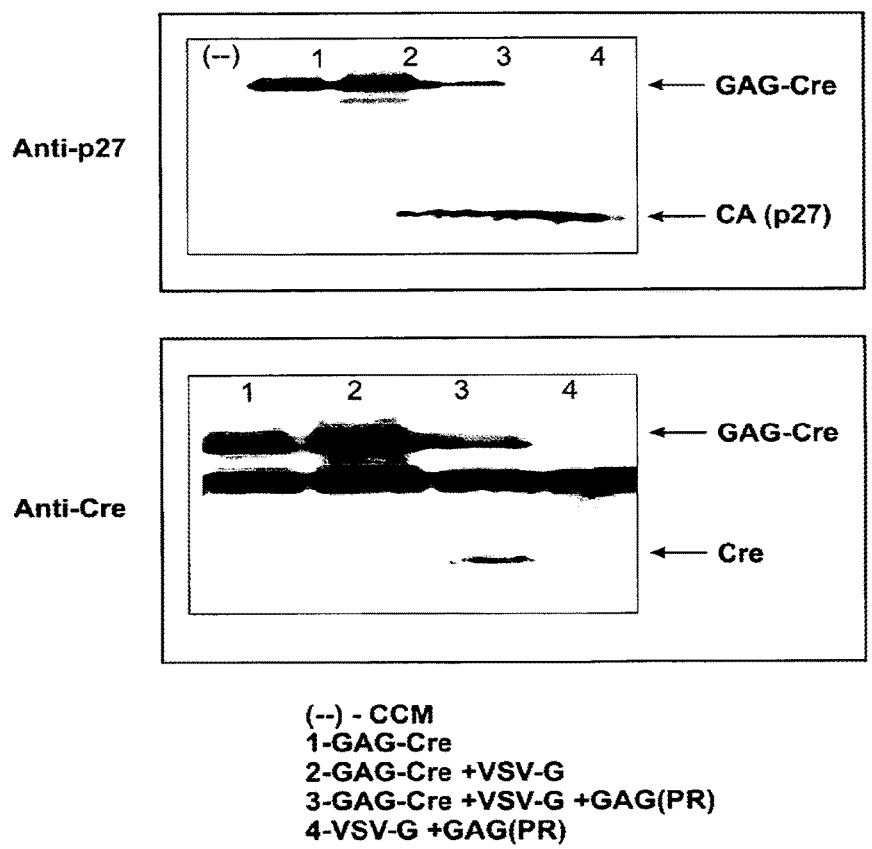

FIG. 6 shows processing of GAG and GAG–Cre fusion in the presence of retroviral protease. VLPs were probed with anti-p27 (CA of GAG) and anti-Cre. The processed GAG (p27) can be observed only where VLPs were co-packaged with GAG-Pr (lanes 3 and 4). Lanes 1 and 2 show unprocessed GAG due to absence of protease. On lower panel the processed Cre recombinase is observed only where VLPs were co-packaged with GAG-Protease (lane 3), unprocessed GAG–Cre is observed in lanes 1 and 2.

Figure 7:
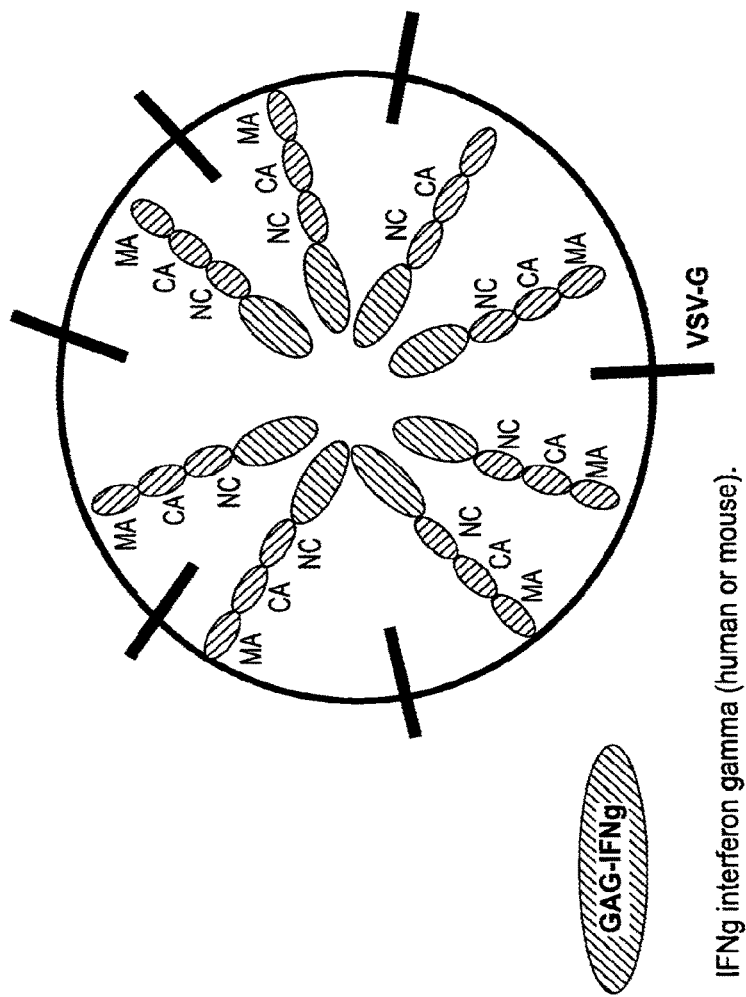

FIG. 7 is a schematic that shows generation of VLPs consisting of GAG-INFg. In the Figure matrix (MA), capsid (CA), nucleocapsid (NC) represents GAG protein.

Figure 8:
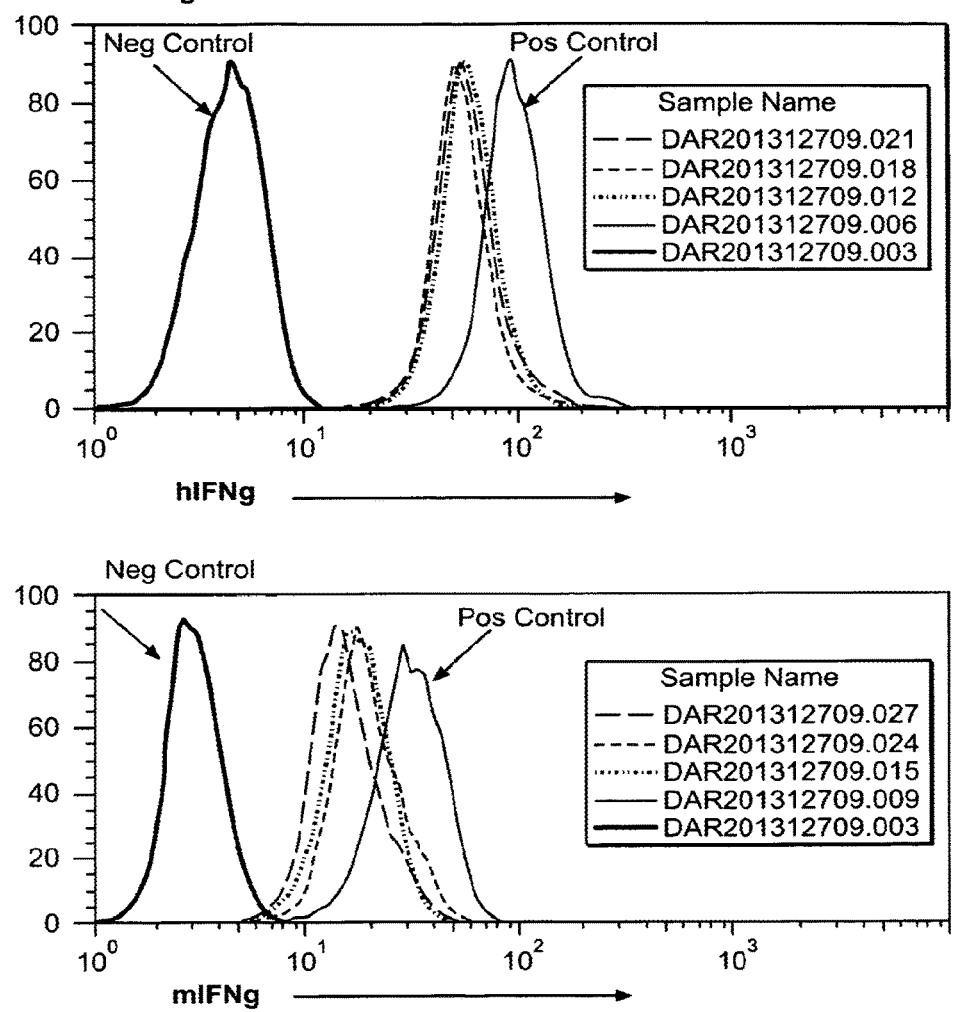

FIG. 8 is two graphs that show results from experiments where the 293T cell line was transduced with VLPs consisting of GAG-IFN-gamma (human or mouse) pseudotyped with VSV–G envelope. $3.0\times10^6$ cells were plated in 10 cm dish (10 ml of DMEM containing 10% FBS) 24 hr before transduction. At the time of transduction fresh complete culture medium was added to cells (total 10 ml supplemented with VLPs (proxy $2\times10^6$ VPLs). The flow cytometry assay was performed 1 hr post-transduction.

FIG. 9 is a schematic that shows cell killing with cytotoxic enzymes and Pro-drugs. Here, VLPs were generated to deliver cytotoxic enzymes and to test effectiveness of GAG-fusion-Fcy::Fur (Fcy and Fur enzymes convert pro-drug 5FC into cell toxic 5FU) in cell killing process. The VLPs were pseudotyped with wild type VSV–G.

Figure 10:
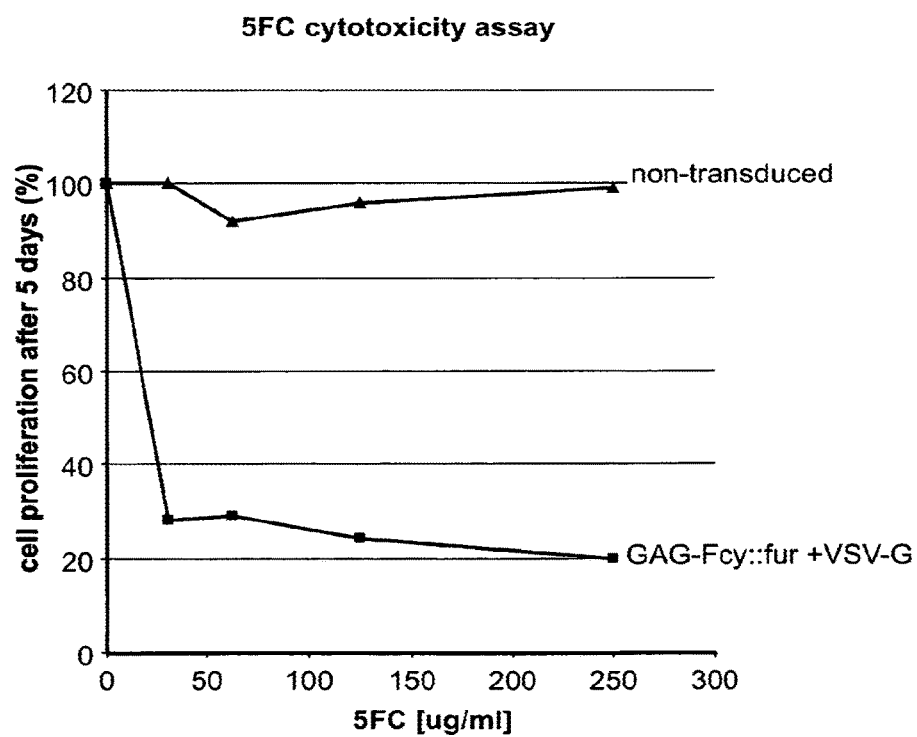

FIG. 10 is a graph that shows the results of treatment of 293T cells with VLPs consisting of GAG-Fcy::Fur–/+VSV–G envelope) in dose dependent manner of 5FC. An extensive killing of cells was observed where VLPs were pseudotyped with VSV–G envelope.

Figure 11:
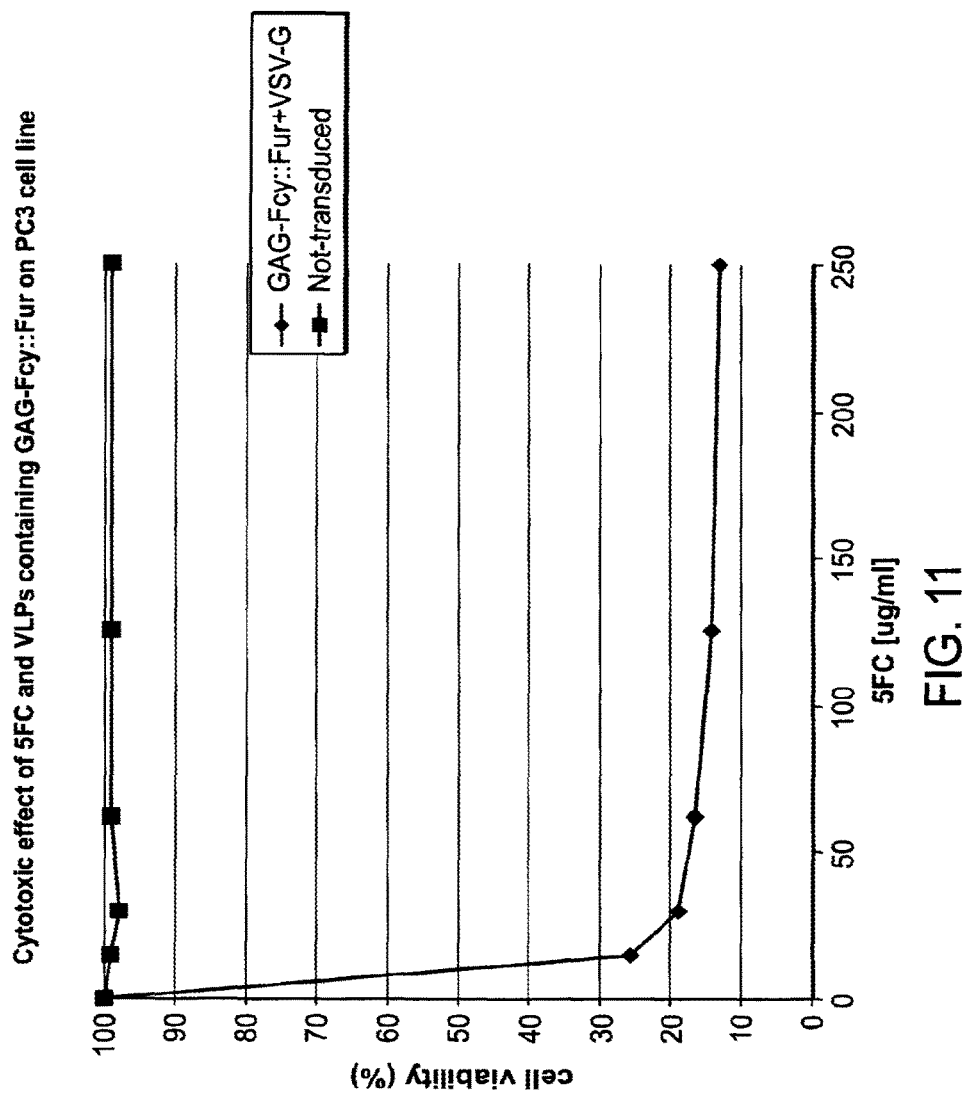

FIG. 11 is a graph that shows the results of VLPs mediated cytotoxicity on PC3 (prostate cancer) cell line. In this experiment, PC3 cells were simultaneously exposed to given VLPs and 5FC and different doses.

Figure 12:
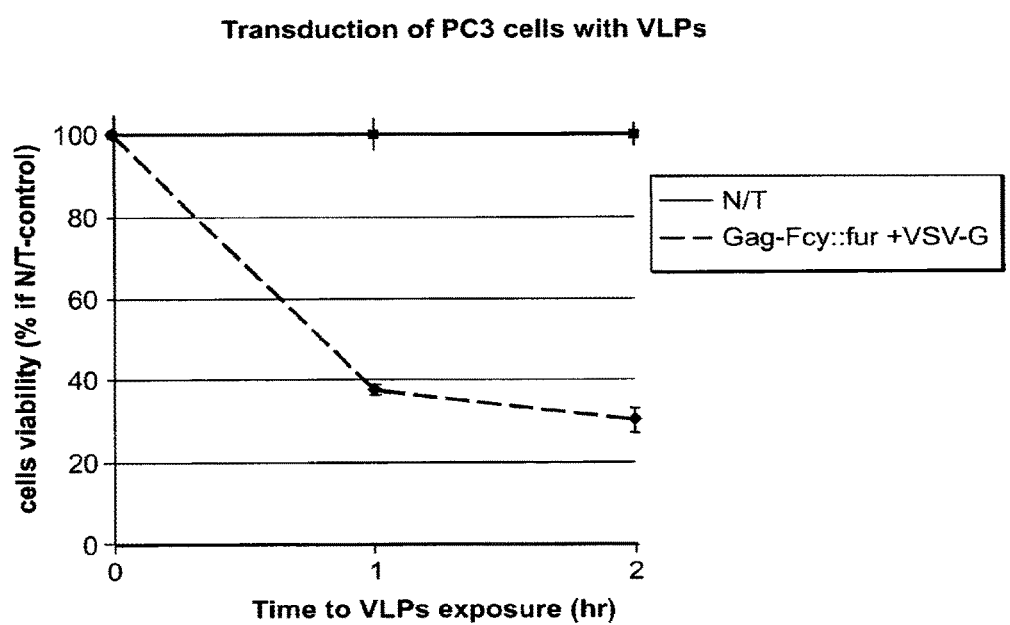

FIG. 12 is a graph that shows the effect of limited exposure to VIPs of PC3 cell line to VLPs.

Figure 13:
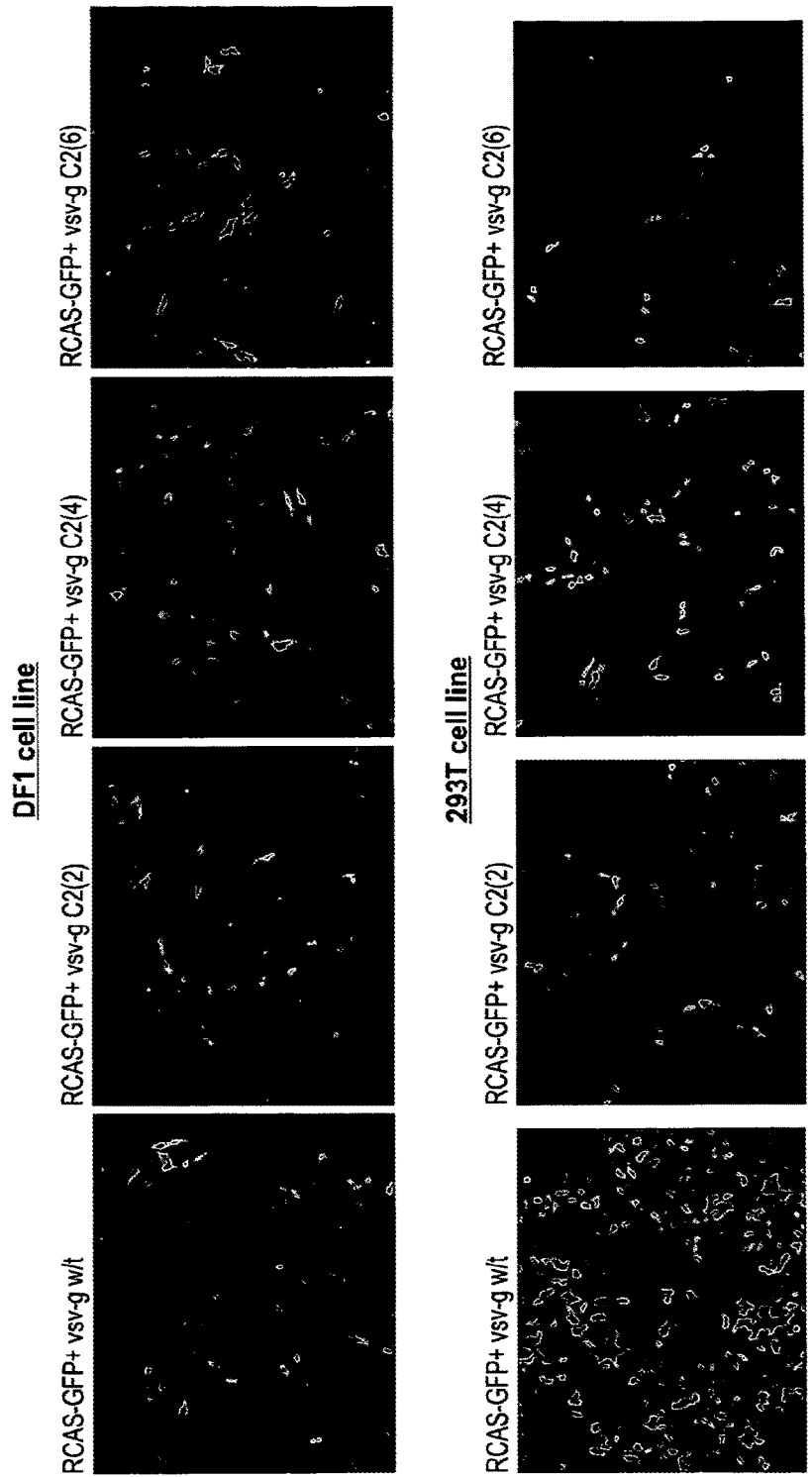

FIG. 13 is a panel of images that shows the generation of VSV–G mutant and that the VSV–G Cys 2 mutant has lower ligand binding activity. A VSV–G mutant Cys2 (C2) was generated to keep its fusogenic activity with low or no ligand biding activity. The VSV–G mutant (s) are used for target (ligand) specific delivery of proteins. The VSV–G wild type (w/t) and VSV–G(C2) envelope can be efficiently incorporated into retrovirus. The results show that binding to cellular receptor on 293T cells using VSV–G(C2) is very limited resulting in only fractional infectivity compared to retrovirus pseudotyped with w/t VSV–G envelope. Three independent mutants of Cys 2-2, 4 and 6 were tested.

Figure 14:
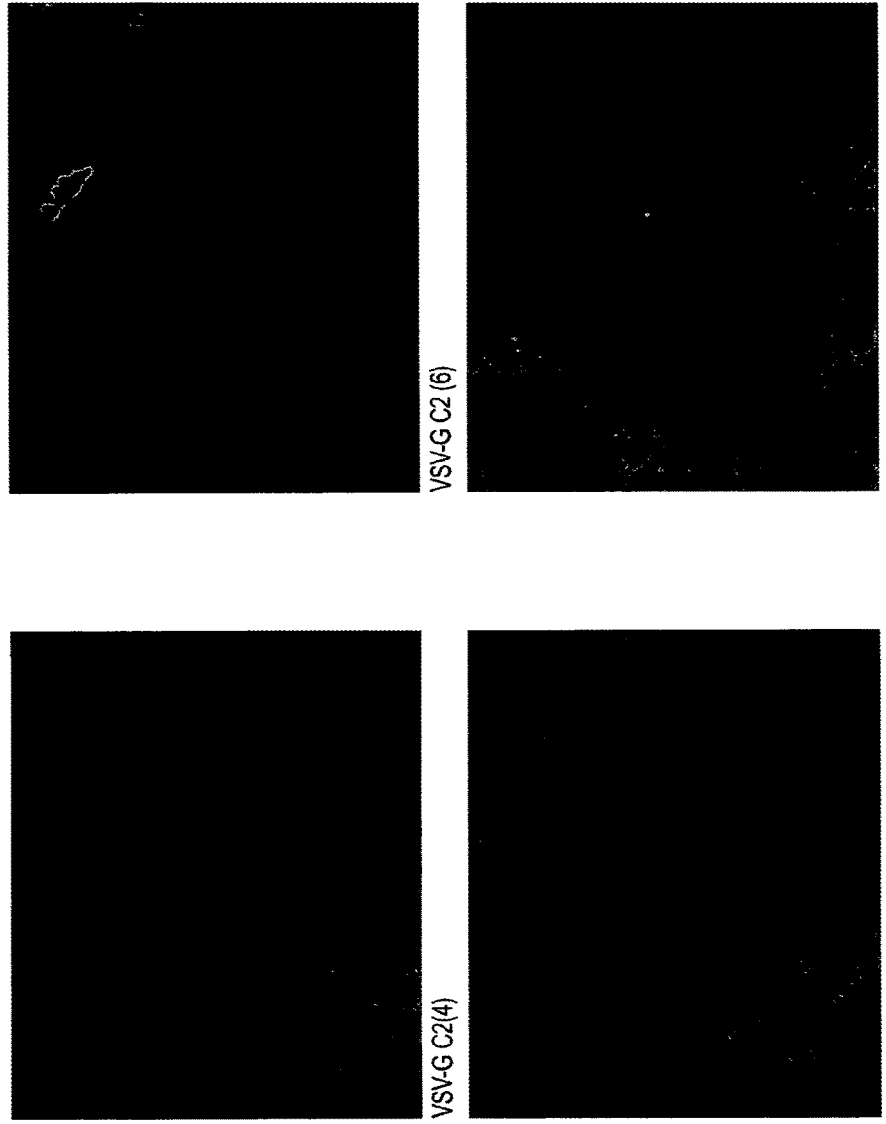

FIG. 14 shows that VSV–G Cys2 mutant has fusogenic activity. The targeted delivery of VLPs carrying therapeutic or cytotoxic proteins to target cell and organs in vivo would make very attractive method for in vivo therapy. The results here show that mutant VSV–G (C2) contains non-functional binding domain but functional fusion domain. This mutant was isolated to complement its fusogenic activity with target specific binding mediated by cell specific ligand (protein expressed on VLPs surface). The VSV–G(C2) mutant shows good fusion activity in cell fusion assay at pH 5.14 compared to wild type VSV–G envelope.

Figure 15:
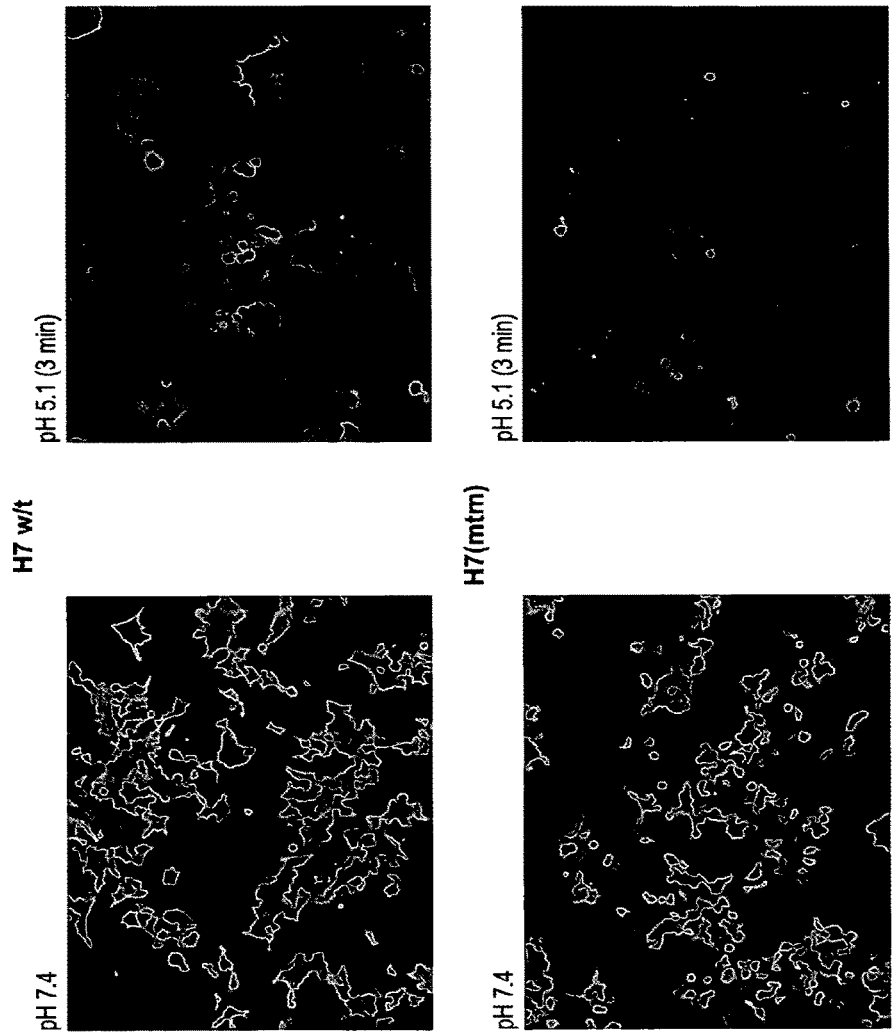
Figure 18:
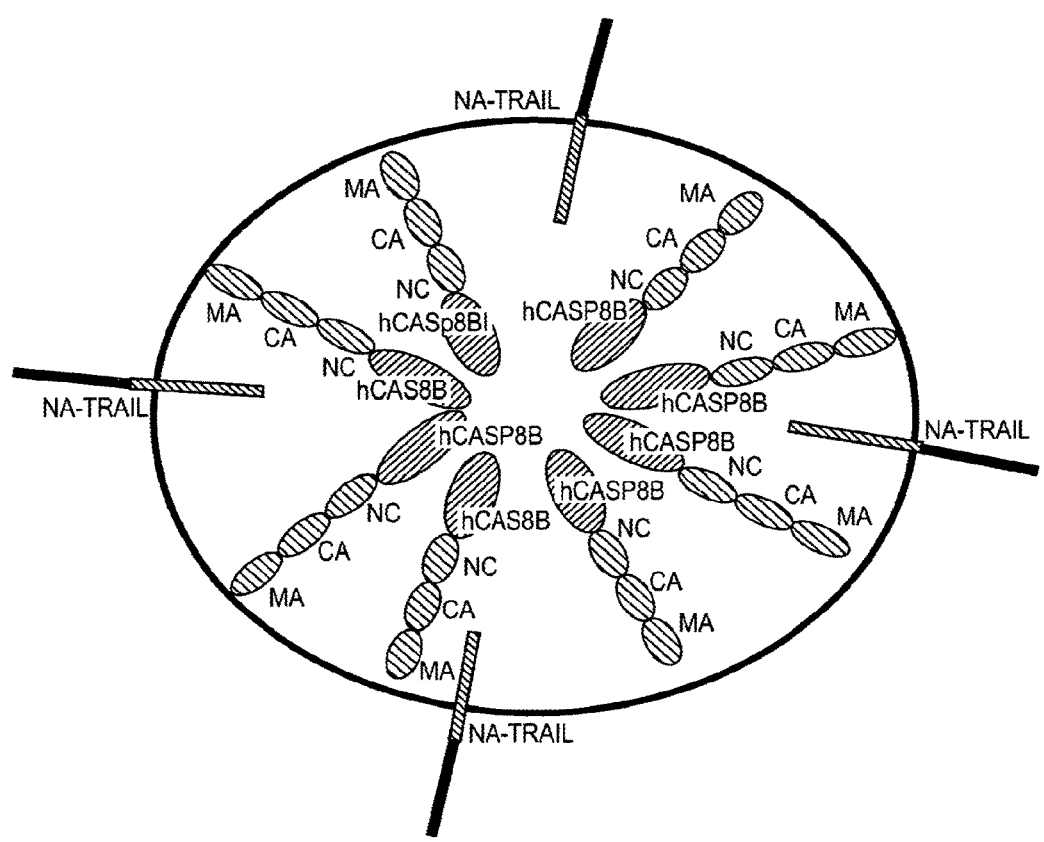

FIG. 15 shows that mutated Hemagglutinin (HA) of H7 Influenza virus can also be used for targeted delivery. Another candidate for targeted delivery of VLPs is mutated form of H7 influenza virus HA envelope. It was shown that this mutated form of HA (mtm) envelope results in limited infectivity compared to wild type (w/t) H7 HA envelope. As shown here the fusogenic activity of mutated envelope is as good as w/t. This is another potential candidate for complementation with target specific ligand for targeted VLPs delivery.

FIG. 16 is a schematic illustrating the concept of delivering of VLPs consisting of protein of interest (POI) and cell specific targeting ligand through neuraminidase, NA-Ligand, (for targeting) complemented by fusogenic activity of VSV–G (C2) envelope.

FIG. 17 is a schematic showing a VLP of the invention. In this configuration peptide ligand is expressed on VLP surface as fusion Ligand-HA protein for targeting and VSV–G(C2) for fusion.

FIG. 18 is a schematic showing the design of VLPs consisting of GAG-human Caspase 8 and TRAIL targeting ligand on VLPs surface for delivery to cells over-expressing DR4 (death receptor) and DR5. This type of VLPs can be used to target cancer cells and induce programmed cell death (apoptosis) through TRAIL receptor and Caspase 8 activity in target cells.

FIG. 19 is a schematic showing generation of VLPs for generation of i-Stem cells. Here, stem cell transcription factors are cloned as GAG-fusion for stem cell generation from fibroblasts.

FIGS. 20 (A-C) shows (A) Subcellular localization of GFP and GFP-Tus derivatives. Panel (*a*), GFP only; Panel (b), GFP-TUS is the fusion of eGFP with full-length Tus; Panel (c), GFP-TUS-AC is GFP fused with amino acids Tus containing 1-217 of Tus. (B) shows confirmation of nuclear localization of GFP-Tus proteins. Panel (a), GFP fluorescence of GFP-Tus protein; Panel (b), cells were stained with DAPI; and Panel (c), Superimpose of panels (a) and (b). (C) shows cytoplasmic localization of GFP fused with 1-217 amino acids of Tus. Panel (a), GFP fluorescence; Panel (b), DAPI staining and Panel (c), Superimpose of panels (a) and (b).

FIGS. 21 (A and B) is a schematic where (A) shows localization of NLS and NES determinants of Tus by deletion analysis. Full length and various deletions of Tus were fused with eGFP and localization of the fusion protein in nucleus (N), cytoplasm (C) and all over the cell (C+N) were indicated on right. The boundary of the NLS region was between amino acids 218 to 264 and the boundary of the NES region was between 1 and 77 amino acids. (B) shows comparison of various types of known NLS (SEQ ID NOS 25 and 26, respectively, in order of appearance) with putative NLS sequence of Tus (SEQ ID NO: 2).

FIGS. 22 (A and B) are two panels showing results of immunoflouresence where (A) shows subcellular localization of un-mutated NLS and NLS mutants. Mutation was done using a plasmid containing GFP fused to Tus (218-309) expressed in PC3 cells. Expression of only GFP was shown in the top left panel. Localization of un-mutated GFP-Tus (218-308) fusion was shown in the upper right panel. Mutants (indicated) of specific amino acids Tus within 218-309 amino acids fused to GFP were expressed in PC3 cells. (B) shows 9 Putative NLS region containing 9 amino acids was fused to GFP expressed in PC3 cells.

FIG. 23 (A-D) is four panels where (A) shows location of NES sequence (SEQ ID NO:3). Replacement of full-length Tus in pDest 472 GFP-Tus vector with the indicated region of Tus was used to localize the region of NES. (B) shows comparison of Tus NES (SEQ ID NO:3) with known NES (p53 (SEQ ID NO: 29), HIV Rev (SEQ ID NO: 27) and PKI (SEQ ID NO: 28)) were shown. Amino acids in red indicate leucine and isoleucine residues are hallmarks of NES. (C) shows effect of mutation of leucine 33 and 34 in NES function. (a) Localization of GFP-Tus(1-77) and (b) GFP-Tus (1-77:L33A-L34A) in PC3 cells. (D) shows distribution of GFP and GFP-TetR fusion proteins in PC3 cell line.

Figure 24A:
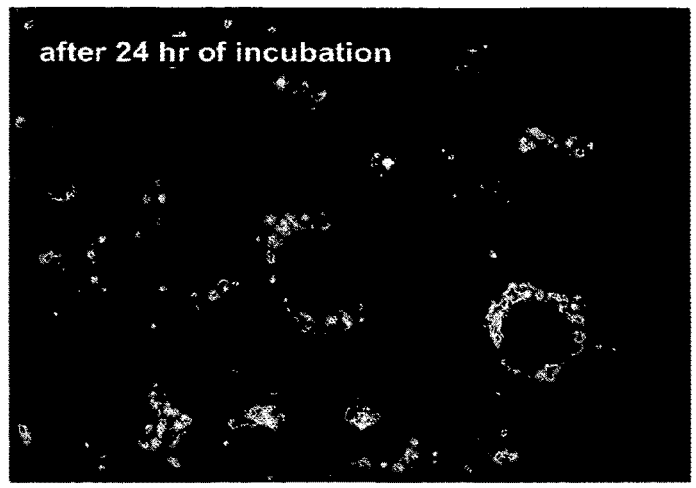
Figure 24B:
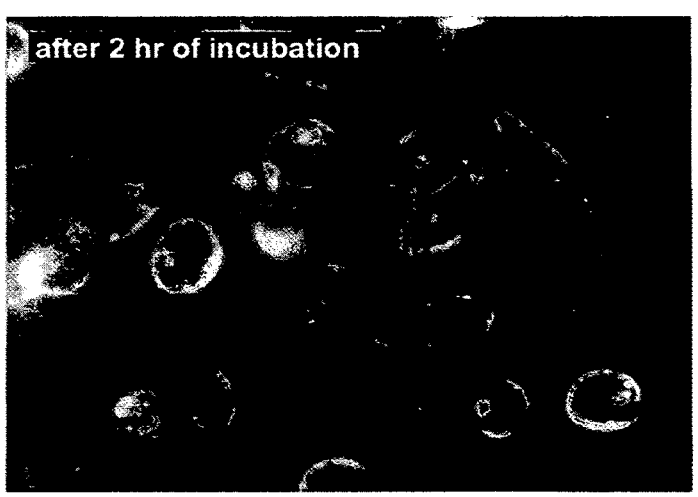
Figure 24C:
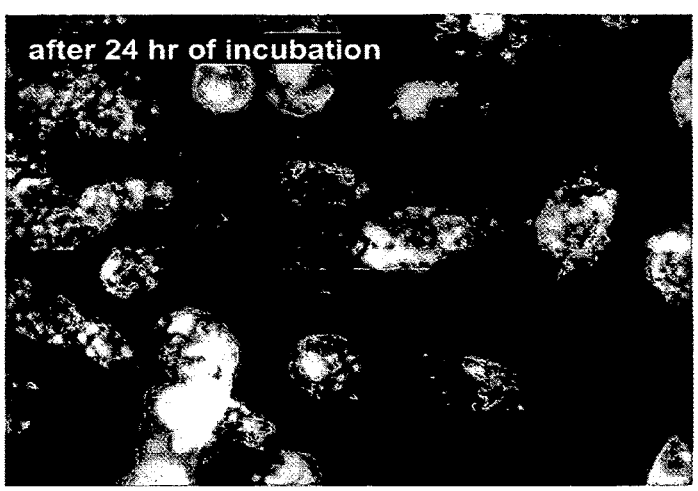

FIG. 24 (A-C) shows protein delivery using GFP-Tus and GFP-Tus NLS fusion protein. (A) shows internalization of GFP-Tus protein in PC3 cell line after 24 hrs post addition of the fusion protein. (B) shows internalization of GFP-Tus NLS after 2 hrs and (C) 24 hrs post addition of the fusion protein. Addition of GFP fusion protein (control) showed no internalization (data not shown).

Figure 25:
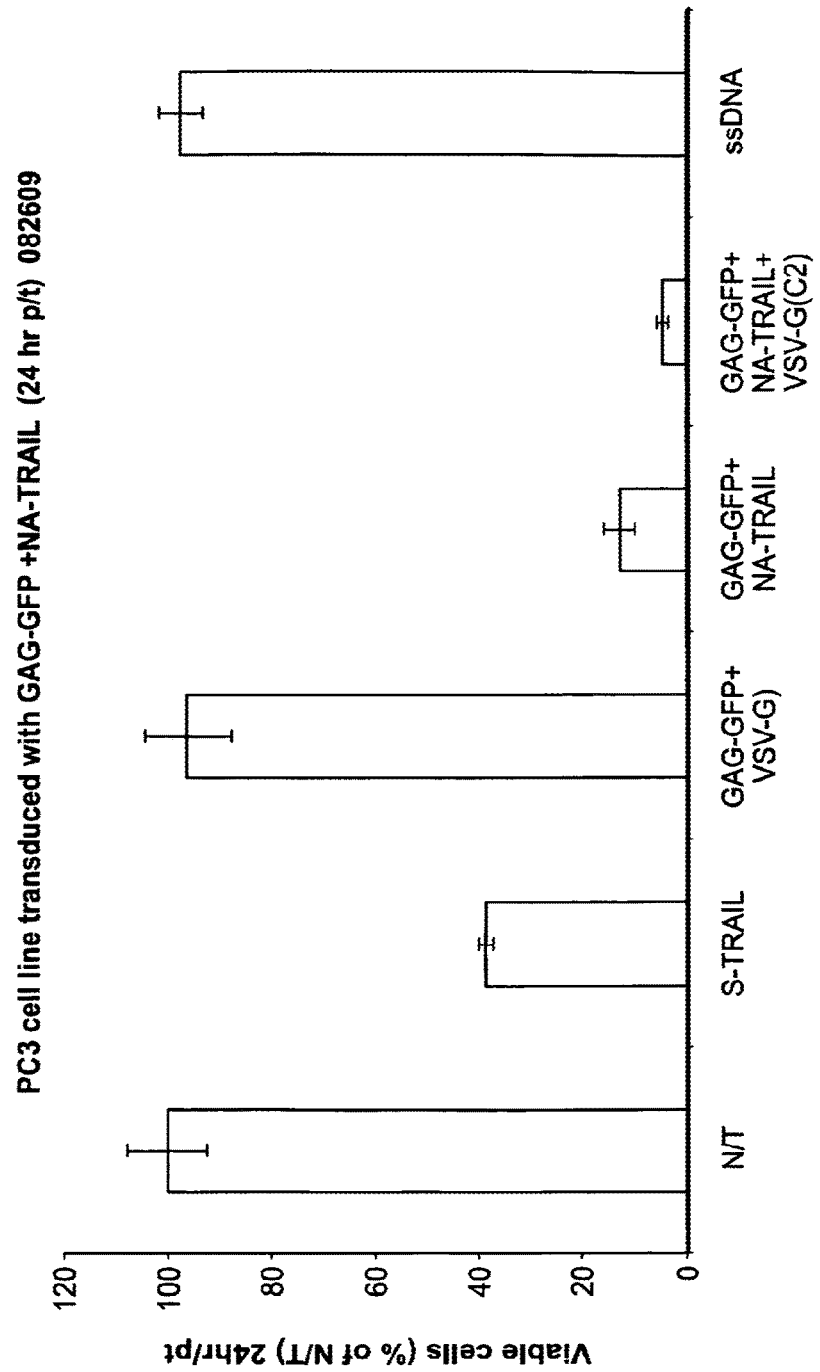

FIG. 25 is a graph that shows transduction of recipient PC3 cell line with VLPs consisting of GAG–GFP+NA–TRAIL+VSV–G(C2) caused over 90% cell death, whereas TRAIL at 100 ng/ml and GAG–GFP+NA–TRAIL caused 60% and 80% cell death, respectively.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When the terms "one," "a," or "an" are used in this disclosure, they mean "at least one" or "one or more," unless otherwise indicated.

As used herein, the terms "about" or "approximately" when referring to any numerical value are intended to mean a value of ±10% of the stated value. For example, "about 50° C." (or "approximately 50° C.") encompasses a range of temperatures from 45° C. to 55° C., inclusive. Similarly, "about 100 mM" (or "approximately 100 mM") encompasses a range of concentrations from 90 mM to 110 mM, inclusive.

The term "conjugation" as used herein refers to attachment by covalent bonds or by strong non-covalent interactions. Any method normally used by those skilled in the art for the coupling of biologically active materials can be used in the present invention. Covalent bonds can be, for example, ester, ether, phosphoester, amide, peptide, imide, carbon-sulfur bonds, carbon-phosphorus bonds, and the like.

The term "fusogenic protein" as used herein is meant to refer to a viral protein that can induce the fusion of the plasma membrane derived envelope of the VLP to the membrane of the recipient cell.

The term "link" as used herein is meant to refer to an attachment between two proteins, for example a structural protein and a protein of interest. The term "link" includes terms such as "conjugated", "fused", "enclosed", "packaged" and "attached". For example, a link either associates a first protein with an attachment site associate with the second protein, or, the second protein already comprises or contains the second attachment site, typically—but not necessarily—as one amino acid residue. The term "link" or "linker" does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occurring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1-C6 alkyl-, cycloalkyl (C5,C6), aryl or heteroaryl moiety. However, in addition to an amino acid linker, a linker comprising preferably a C1-C6 alkyl-, cycloalkyl-(C5,C6), aryl- or heteroaryl-moiety and devoid of any amino acid(s) shall also be encompassed within the scope of the invention.

As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the term "mixed" refers to the combination of two or more substances, ingredients, or elements that are added together, are not chemically combined with each other and are capable of being separated.

As used herein a "nuclear export signal (NES)" is meant to refer to an amino acid sequence in a protein that targets the protein for export from the nucleus to the cytoplasm. Preferably, the NES is hydrophobic. In certain preferred embodiments, the NES is 5-25 amino acids in length. In further preferred embodiments, the NES is 21 amino acids in length. In certain embodiments, the NES comprises SEQ ID NO: 3.

As used herein a "nuclear localization signal (NLS)" is meant to refer to an amino acid sequence in a protein that targets a protein located in the cytoplasm for import to the nucleus. In certain preferred embodiments, the NLS is 5-10 amino acids in length. In further preferred embodiments, the NLS is 9 amino acids in length. In certain preferred embodiments, the NLS comprises SEQ ID NO: 1. In other preferred embodiments, the NLS comprises SEQ ID NO: 2.

The term "polypeptide" as used herein refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. Post-translational modifications of the polypeptide, for example, glycosylations, acetylations, phosphorylations, and the like are also encompassed.

The term "a fragment of a polypeptide" or "a fragment of a protein," as used herein, should encompass any polypeptide comprising, or alternatively or preferably consisting of, at least 6, 7, 8, 9, 10, 11, 12, 17, 18, 19, 20, 25, 30 contiguous or discontinuous amino acids of the protein or polypeptide, as defined herein, as well as any polypeptide having more than 65%, preferably more than 80%, more preferably more than 90% and even more preferably more than 95% amino acid sequence identity thereto.

The term "a variant of a polypeptide" or "a variant of a protein" or "derivative of a polypeptide" or "derivative of a protein" as used herein, should encompass any polypeptide comprising, or alternatively or preferably consisting of, any natural or genetically engineered polypeptide having more than 70%, preferably more than 80%, even more preferably more than 90%, again more preferably more than 95%, and most preferably more than 97% amino acid sequence identity with the sequence of the protein or polypeptide. Preferred methods of generating a variant of a protein is by genetic engineering, preferably by insertion, substitution, deletion or a combination thereof.

As used herein, the term "subject" is meant to refer to include, for example, humans, sheep, horses, cattle, pigs, dogs, cats, rats, mice, mammals, birds, reptiles, fish, insects and arachnids.

As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse. In certain examples, the terms are meant to refer to an approach for obtaining beneficial or desired clinical results. For purposes of embodiments of this disclosure, beneficial or desired clinical results include, but are not limited to, alleviation of symptoms, diminishment of extent of disease, stabilization (e.g., not worsening) of disease, preventing spread of disease, delaying or slowing of disease progression, amelioration or palliation of the disease state, and remission (partial or total) whether detectable or undetectable. In addition, "treat", "treating", and "treatment" can also mean prolonging survival as compared to expected survival if not receiving treatment.

The term "Tus" as used herein is meant to refer to an *E. coli* DNA replication terminus site binding protein that terminates replication of DNA in *E. coli*. In certain embodiments, the Tus protein is encoded by NCBI Accession No. AAC74682. (SEQ ID NO: 1).

As used herein "viral structural protein" is a protein that contributes to the overall structure of the capsid protein or the protein core of a virus. The viral structural protein of the present invention can be obtained from any virus which can form enveloped VLPs.

"Virus-like particle (VLP)", as used herein, refers to a structure resembling a virus particle. In preferred embodiments, a VLP contains at least one fusogenic protein displayed on the surface of the particle. A virus-like particle in accordance with the invention is non-replicative and noninfectious since it lacks all or part of the viral genome, typically and preferably lacking all or part of the replicative and infectious components of the viral genome. Typically, a virus-like particle in accordance with the invention does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. A virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997)). Fundamental laboratory techniques for working with tissue culture cell lines (Celis, J., ed., CELL BIOLOGY, Academic Press, 2nd edition, (1998)) and antibody-based technologies (Harlow, E. and Lane, D., "Antibodies: A Laboratory Manual," Cold Spring Harbor Laboratory, Cold Spring Harbor, N.Y. (1988); Deutscher, M. P., "Guide to Protein Purification," Meth. Enzymol. 128, Academic Press San Diego (1990); Scopes, R. K., "Protein Purification Principles and Practice," 3rd ed., Springer-Verlag, New York (1994)) are also adequately described in the literature, all of which are incorporated herein by reference.

DETAILED DESCRIPTION OF THE INVENTION

The present invention is based on the finding that a protein of interest can be delivered to a cell as a fused or an unfused protein. The present invention describes, in part, a mutant VSV–G (envelop protein) that has lost ligand binding activity but has retained its cell fusion activity. The VSVs described in the present invention have a particular use in targeted delivery of proteins. In addition, this type of VSV–G mutant (fusion proficient) can be used in conjunction with NA- or HA fused ligand (target specific ligand, binding protein) for targeted protein delivery.

In particular, the present invention has shown that a virus like particle (VLP) was made with two GAG-fusion (GAG-protein of interest and GAG-Protease) to deliver the protein of interest to the cell as an unfused protein. This finding is important because the GAG-protein of interest may not be active, while the protein of interest in its unfused form, after delivery to the cell, will be active.

For example, the present invention described targeted delivery of proteins, such as interferon (both human and mouse) in cells, and that cytotoxic enzymes that convert pro-drug into active drug can be delivered into cells. Further, the present invention described a mutant VSV-G (envelop protein) that lost ligand binding activity but retained it cell fusion activity, and has a particular use in targeted delivery of proteins.

The present invention also describes TUS protein, an *E. coli* replication fork arresting protein, that contains separate sequences that function as nuclear localization signals (NLS) and nuclear export signals (NES). According to embodiments of the invention described herein, the localized delivery of proteins (for example nuclear delivery versus cytosolic delivery) can be suitably carried out by the addition of either NLS or NES of Tus (or other proteins) on the protein of interest, preferably at the end of the protein of interest, fused with gag or other structural proteins used for making VLPs.

A protein of interest is only limited by the skilled practitioner making use of the invention as described herein. Accordingly, a protein of interest can be, for example, a therapeutic, for example a chemotherapeutic, a cytotoxic enzyme, a stem cell transcription factor, an immunostimulatory protein. In certain preferred examples, the protein is selected from the group consisting of, but not to be limited to, growth factors, antiapoptotic proteins, hormones, proteases, recombinases, and integrases.

I. Virus Like Particles

Virus-like particles refer to structures resembling a virus particle but which are not pathogenic. In preferred embodiments, VLPs can be made in vivo or in vitro.

VLPs are structures resembling a virus particle but devoid of the viral genome. Accordingly they are incapable of replication and devoid of pathogenicity. The particle typically comprises at least one type of structural protein from a virus. In most cases this protein will form a proteinaceous capsid (e.g. VLPs comprising a retrovirus, adenovirus or bacteriophage structural protein). In some cases the capsid will also be enveloped in a lipid bilayer originating from the cell from which the assembled VLP has been released (e.g. VLPs comprising a human immunodeficiency virus structural protein such as GAG).

VLPs are typically formed when a gene encoding a viral structural protein is overexpressed in a host cell in isolation from other viral genes.

Examples of VLPs that are known in the art include, but are not limited to, the capsid proteins of Hepatitis B virus (Ulrich, et al., Virus Res. 50:141-182 (1998)), measles virus (Warnes, et al., Gene 160:173-178 (1995)), Sindbis virus, rotavirus (U.S. Pat. Nos. 5,071,651 and 5,374,426), foot-and-mouth-disease virus (Twomey, et al., Vaccine 13:1603-1610, (1995)), Norwalk virus (Jiang, X., et al., Science 250:1580-1583 (1990); Matsui, S. M., et al, I Clin. Invest. 87:1456-1461 (1991)), the retroviral GAG protein (PCT Patent Appl. No. WO 96/30523), the retrotransposon Ty protein pl, the surface protein of Hepatitis B virus (WO 92/11291), human papilloma virus (WO 98/15631), human polyoma virus (Sasnauskas K., et al., Biol. Chem. 380(3): 381-386 (1999); Sasnauskas K., et al., Generation of recombinant virus-like particles of different polyomaviruses in yeast. 3rd International Workshop "Virus-like particles as vaccines." Berlin, Sep. 26-29 (2001)), RNA phages, Ty, fr-phage, GA-phage, AP 205-phage and Q(3)-phage.

Virus-like particles refer to VLPs that are described in detail in WO 03/024481, the disclosure of which is incorporated herein by reference. Examples of VLPs include, but are not limited to, the capsid proteins of Hepatitis B virus, RNA phages, Ty, fr-phage, GA-phage, AP 205-phage and, in particular, Qβ-phage. In a more specific embodiment, the VLP can comprise, or alternatively essentially consist of, or alternatively consist of recombinant polypeptides, or fragments thereof. In a preferred embodiment, the virus-like particle comprises, consists essentially of or alternatively consists of recombinant proteins, or fragments thereof, of a RNA-phage.

A VLP refers to a structure resembling a virus particle but which has not been demonstrated to be pathogenic. Typically, a virus-like particle in accordance with the invention does not carry genetic information encoding for the proteins of the virus-like particle. In general, virus-like particles lack the viral genome and, therefore, are noninfectious. Also, virus-like particles can often be produced in large quantities by heterologous expression and can be easily purified. Some virus-like particles may contain nucleic acid distinct from their genome. As indicated, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome.

The term "plasma membrane-derived lipid bilayer envelope" refers to a lipid bilayer derived from the plasma membrane of the host cell from which the VLP has been released. This envelope either partially or totally encloses the VLP. The VLP can be completely (or substantially completely) enclosed within the envelope. The lipid bilayer will have a macromolecular composition corresponding to the composition of the plasma membrane of the host cell. The bilayer will have similar proportions of the same lipids, proteins and carbohydrates. Such macromolecules would include transmembrane receptors and channels (such as receptor kinases and ion channels), cytoskeletal proteins (such as actin), lipid or protein linked carbohydrates, phospho lipids (such as phosphatidylcho line, phosphatidylserine and phosphatidylethanolamine), and cholesterol. The composition will be complex and distinct from the typical composition of artificial bilayer preparations such as liposomes. Liposomes typically comprise a small number of different types of lipids. They are formed spontaneously after sonification of a suspension of these lipids in an aqueous solution. The liposomes will encapsulate part of the aqueous solution and so liposomes can be packed with substrates of interest by including those substrates in the aqueous solution. Liposomes can also be produced with transmembrane proteins embedded in the bilayer however technical limitations mean that the numbers and variety of proteins that can be included in liposomes is severely curtailed. Thus, a liposome bilayer is known by one of skill in the art as distinct in terms of complexity from the plasma membrane derived lipid bilayer of the VLPs of the invention.

As used herein, a "viral structural protein" is a protein that contributes to the overall structure of the capsid protein or the protein core of a virus. The viral structural protein of the present invention can be obtained from any virus which can form enveloped VLPs. These are typically proteins from viruses that are naturally enveloped. Such viruses include, but are not limited to, the Retroviridae (e.g. HIV, Moloney Murine Leukaemia Virus, Feline Leukaemia Virus, Rous Sarcoma Virus), the Coronaviridae, the Herpesviridae, the Hepadnaviridae, and the Orthomyxoviridae (e.g. Influenza Virus). However, naturally non-enveloped viruses may form enveloped VLPs and these are also encompassed by the invention.

Naturally non-enveloped viruses include the Picornaviridae, the Reoviridae, the Adenoviridae, the Papillomaviridae and the Parvoviridae.

Preferred structural proteins are the Retroviridae Gag proteins. Particularly preferred as the structural protein is the protein corresponding to the HIV-1 gag gene. This is because the production and assembly of GAG VLPs is highly efficient and these VLPs have low cytotoxicity. The gag gene of the RSV codes for the polyprotein GAG which is a precursor of the structural proteins matrix (MA), capsid (CA), nucleocapsid (NC). GAG is cleaved into the individual proteins in mature, infectious virions of RSV by retroviral protease. In absence of retroviral protease GAG remains as a single protein, however, VLPs complemented with retroviral protease will consist of processed GAG components.

The mechanisms underlying and proteins involved in Gag VLP formation are extensively discussed in the prior art (see Carriere et al., 1995 J. Virol. 69:2366-2377; Wilk et al., 2001 J. Virol. 75:759-77130; US2002/0052040; Chazal and Gerlier, 2003 Microbiol. Molec. Biol. Rev. 67:226-237; Hong and Boulanger, 1993 J. Virol. 67:2787-2798; Royer et al., 1992 J. Virol. 66:3230-3235; Spearman et al., 1994 J. Virol. 68:3232-3242 and references cited therein).

Fragments and derivatives of these naturally occurring structural proteins that retain the ability to form VLPs are encompassed by the invention. The skilled practitioner will be aware of how to determine if a particular fragment or derivative retains the ability to form VLPs. For instance see Carriere et al., 1995 J. Virol. 69:2366 and Wilk et al., 2001J. Virol. 75:759-77130 and references cited therein (for instance Facke, et al 1993, J. Virol. 67, 4972-4980) provide direction as to the identification of regions and fragments of Gag that retain the ability to form VLPs. Such technique can be readily applied to other viral structural proteins. These derivatives of naturally occurring sequences will typically have at least 40%, preferably 50 or 60% or more, particularly 70 or 80% or more sequence homology with the native sequence. For the purposes of the present invention, and in accordance with common understanding in the art, "sequence homology" is not used to refer only to sequence identity but also to the use of amino acids that are interchangeable on the basis of similar physical characteristics such as charge and polarity. Substitution of an amino acid within a signal sequence with an amino acid from the same physical group is considered a conservative substitution and would not be expected to alter the activity of the signal peptide. Thus a derivative which just replaced leucine with isoleucine throughout would be considered to have 100% "sequence homology" with the starting sequence. Convenient groups are, glycine and alanine; serine, threonine, asparagine, glutamine and cysteine; lysine arginine and histidine; glutamic acid and aspartic acid; valine, leucine, isoleucine, methionine, phenylalanine, tryptophan and tyrosine. Preferred subgroups within this last group include leucine, valine and isoleucine; phenylalanine, tryptophan and tyrosine; methionine and leucine. Sequence homology may be calculated as for sequence identity' discussed below but allowing for conservative substitutions as discussed above.

Preferably, the derivatives of naturally occurring virus structural proteins or active fragments thereof exhibit at least 50%, preferably at least 60% or 70%, e.g. at least 80% sequence identity to a naturally occurring structural protein or portion thereof (as determined by, e.g. using the SWISS-PROT protein sequence databank using FASTA pep-cmp with a variable pamfactor, and gap creation penalty set at 12.0 and gap extension penalty set at 4.0, and a window of 2 amino acids.

Naturally occurring structural proteins, or fragments or derivatives thereof, may be provided as a fusion protein with one or more domains of structural proteins belonging to different species, subgroups families or subfamilies of viruses (e.g. Lentivirus and spumavirus; see Carriere et al, supra), or with non-viral protein sequences.

Preferably, the VLP will typically comprise multiple copies of the viral structural protein (Briggs, J. A., et al., 2004. Nat. Struct. Mol. Biol. 11:672-675). Preferably the VLP will comprise between 1000 and 4000 copies of the viral structural protein.

The term "protein of interest" refers to the protein that is to be delivered to the recipient cell. Such proteins may include proteins not found in the recipient cell, proteins from different species or cloned versions of proteins found in the recipient cell. Certain preferred target proteins of the invention will be proteins with the same status as that found in the recipient cell expressed in such a way that post-translational modification is the same as that found in the recipient cell. Such modification includes glycosylation or lipid modification addition of coenzyme groups or formation of quaternary structure. Other preferred proteins are wild type proteins corresponding to proteins found in mutated form or absent in the recipient cell.

The protein is limited only by what is envisioned by the skilled practitioner. For example, in a therapeutic setting, the protein is only limited by what is envisioned by the clinician for therapeutic use.

In certain preferred examples, the protein is selected from the group consisting of, but not to be limited to, growth factors, antiapoptotic proteins, hormones, proteases, recombinases, and integrases.

In further particular examples, the recombinase is selected from Cre recombinase or Flp recombinase.

Preferably, in certain embodiments of the invention, the protein is a protease. More particularly, in certain examples, for example when two VLPs are being delivered into a cell, and one VLP (e.g. VLP1) contains a protease and a second VLP (e.g. VLP2) contains a protease cleavage site, then the protease is tobacco etch virus (TEV) protease as an example. Other protease could be of retroviral origin (including RCAS), precision, factor Xa, enterokinase, etc.

As will be readily apparent to those skilled in the art, the VLP of the invention is not limited to any specific form. The particle can be synthesized chemically or through a biological process, which can be natural or non-natural.

The invention features, in preferred embodiments, a virus-like particle (VLP) comprising a first polypeptide, comprising one or more viral structural proteins, or fragments or derivatives thereof, linked to a protein of interest; and a second polypeptide comprising one or more viral structural proteins, or fragments or derivatives thereof, linked to a protease. In further embodiments, the VLP further comprises a fusogenic protein.

In another aspect, the invention features a VLP comprising one or more viral structural proteins, or fragments or derivatives thereof, linked to a protein, wherein a protease cleavage site is linked to the protein, a fusogenic protein, or fragment or derivative thereof. In preferred embodiments, a binding domain is linked to the one or more viral structural proteins.

In further embodiments, a cleavage site is linked to the protein of interest.

Further, a binding domain may be linked to the one or more viral structural proteins.

In another aspect, the invention features a VLP comprising one or more viral structural proteins, or fragments or derivatives thereof, wherein a binding domain is linked to the one or more viral structural proteins and a protease cleavage site is linked to the protein, a fusogenic protein, or fragment or derivative thereof.

Also featured in the invention is a VLP comprising one or more viral structural proteins, or fragments or derivatives thereof, linked to a protein, wherein the protein is a protease, a fusogenic protein, or fragment or derivative thereof.

According to preferred embodiments of the invention as described herein, the binding domain may be a component of a leucine zipper, for example the leucine zipper is ZE or ZR.

In other embodiments, the binding domain is IgGFc.

In other embodiments, the link in a fusion. As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

In other embodiments, the link is a conjugation.

Accordingly, the invention features in certain preferred embodiments, that a partner for the binding domain is linked to the protease cleavage site.

Preferably, in certain embodiments, the partner for the binding domain is Protein A.

In other cases, the partner for the binding domain is ZE or ZR.

In certain examples, the protease cleavage site is a tobacco etch virus (TEV) protease cleavage site.

In particular embodiments of the invention, the one or more viral structural proteins are from a virus from a family selected from the group consisting of: Retroviridae, Coronaviridae, Herpesviridae, Hepadnaviridae, and Orthomyxoviridae. More particularly, the one or more viral structural proteins is a Retroviridae viral protein from the Human Immunodeficiency Virus. In preferred examples, the structural protein, or fragments or derivative thereof, is a Gag protein.

In preferred embodiments, the Gag protein, or fragments or derivatives thereof is capable of forming an enveloped VLP. Particularly, the fusogenic protein is an envelope glycoprotein, or fragment or derivative thereof.

The term "fusogenic protein" means a viral protein that can induce the fusion of the plasma membrane derived envelope of the VLP to the membrane of the recipient cell. It is this mechanism that results in entry of the proteinaceous component of the VLP to the cytosol. The envelope glycoproteins of RNA viruses and retroviruses are well known to bind cell receptors and induce this fusion.

Accordingly these proteins are responsible for the infectivity of these viruses. Other examples of fusogenic proteins include, but are not limited to, influenza haemagglutinin (HA), the respiratory syncytial virus fusion protein (RS-VFP), the E proteins of tick borne encephalitis virus (TBEV) and dengue fever virus, the E1 protein of Semliki Forest virus (SFV), the G proteins of rabies virus and vesicular Stomatitis virus (VSV) and baculovirus gp64 (Guibing a GH & Friedmann T., 2004, Mol. Ther. 11: 645-651). Functionally equivalent fragments or derivatives of these proteins may also be used. The functionally equivalent fragments or derivatives will retain at least 50%, more preferably at least 75% and most preferably at least 90% of the fusogenic activity of the wild type protein.

Particularly preferred is the envelope glycoprotein from the Vesicular Stomatitis Virus (VSV-G). VSV-G has high fusogenic activity and virtually all mammalian cells can bind VSV-G, via the carbohydrate moiety of their plasma membrane glycoproteins. Without wishing to be being bound by theory, the molecular mechanism of VSV-G-cell surface interaction consists of attachment, followed by a step of membrane fusion between the membrane of the cell and the viral envelope. This process has been well documented for the influenza virus haemagglutinin and host cell plasma membranes (Hunter, E. 1997. Viral entry and receptors, in Retroviruses. Cold Spring Harbor Laboratory Press, New York.).

In certain embodiments, VSV-G comprises an alteration. The alteration can be, for example, a deletion, substitution or addition. In preferred exemplary embodiments, the alteration is a substitution at cysteine 2 (Cys2)

II. Methods of Making VLPs

The present invention also provides methods for making VLPs.

Certain preferred methods of making VLPs include, for example, preparing a first plasmid comprising a nucleic acid sequence encoding one or more viral structural proteins, or fragments or derivatives thereof, linked to a nucleic acid sequence encoding a protein of interest; and a second polypeptide comprising a nucleic acid sequence encoding one or more viral structural proteins, or fragments or derivatives thereof, linked to a nucleic acid sequence encoding a protease; preparing a second plasmid comprising a nucleic acid sequence encoding a fusogenic protein; contacting a target cell with the first plasmid and the second plasmid, where the expressed proteins are capable of forming VLPs; and purifying the VLPs, thereby producing the VLP.

In another aspect the invention provides a method for the production of a VLP as defined above, said method comprising preparing a first plasmid comprising one or more viral structural proteins, or fragments or derivatives thereof, linked to a protein, preparing a second plasmid comprising a fusogenic protein, or fragment or derivative thereof, contacting a target cell with the first plasmid, contacting the target cell with the second plasmid; and collecting the VLP, thereby making a VLP.

Contacting includes cell transfection. Preferably, the cell is grown in culture medium. A cell grown in culture, therefore, will, in exemplary embodiments, consist of a cell layer or portion and a supernatant portion.

In certain embodiments, the target cell grows in culture for 12, 24, 48, 72, or more hours. Following the time period of growth in culture as set forth above, the VLP is collected from the culture medium. Purification of VLPs is well-known to one of skill in the art. Accordingly, purification of VLPs can be carried out by standard procedure known in the art.

In addition, VLPs can be assembled in vitro in the presence of all necessary protein components as well as some form of lipids or liposomes.

Also featured are methods of making a VLP, where the method comprises preparing a first plasmid comprising one or more viral structural proteins, or fragments or derivatives thereof, wherein a binding domain is linked to the one or more viral structural proteins and a protease cleavage site is linked to the protein, preparing a second plasmid comprising a fusogenic protein, or fragment or derivative thereof, contacting a target cell with the first plasmid, contacting the target cell with the second plasmid, collecting the VLP, thereby making a VLP.

Also featured in the invention is a method for making a VLP, where the method comprises preparing a first plasmid comprising one or more viral structural proteins, or fragments or derivatives thereof, linked to a protein, wherein the protein is a protease, preparing a second plasmid comprising a fusogenic protein, or fragment or derivative thereof, contacting a target cell with the first plasmid, contacting the target cell with the second plasmid, and collecting the VLP, thereby making a VLP.

III. Methods of Delivering Protein to a Cell

The invention features in certain aspects delivery of proteins to cell, for example, delivery of therapeutic proteins to cells.

Delivery of proteins to cells has certain advantages over delivery of nucleic acids. Since these proteins can be selected to carry correct post translational modifications if any (e.g. glycosylation, phosphorylation) and can be of the same origin as the host, they will be well tolerated by the hosts and should not induce any immunogenic reaction. This will allow for iterative administrations.

One drawback of virus based gene therapy is the immunogenicity of the vectors. Not only could the vector provoke an immediate adverse reaction to itself, immune protection can develop over time to the extent that repeated administration of the viral vector becomes useless. There is also no possibility of oncogenic integration of a therapeutic protein, which is not the case for all viral vectors. Furthermore, the delivery of a therapeutic protein means the cell machinery of transcription, translation and posttranslational modifications and intracellular trafficking/targeting to a specific cellular compartment (e.g. plasma membrane in case of receptors and cell surface molecules, or nucleus for nuclear factors) is bypassed. This may minimize stress to the cell.

Moreover, delivery of proteins to cells in sufficient amounts by, for example, liposome mediated techniques, can be difficult. Owais, et al. (Eur. J. Biochem, 2000, Vol 267: 3946-3956) have used fusogenic lipids in liposomes to promote fusion with recipient cells and result in delivery of encapsulated protein. In U.S. Pat. No. 5,631,237 Sendai virus proteins were used to promote the fusion of liposomes to recipient cells.

The present invention makes use of VLPs to deliver proteins to cells.

The present invention also makes use of Tus protein, and specifically the NLS or NES that was identified in Tus protein, to deliver protein to a cell nucleus or cytoplasm, respectively.

In one aspect, the invention features a method of delivering one or more proteins to a cell comprising providing one or more VLPs as described herein, and contacting the target cell with the one or more VLPs, thereby delivering one or more proteins to the cell.

The present invention also features a method of delivering one or more proteins to a cell comprising providing a first VLP comprising one or more viral structural proteins, or fragments or derivatives thereof, linked to a protein, wherein a protease cleavage site is linked to the protein and a fusogenic protein, or fragment or derivative thereof to the target cell, providing a second VLP comprising one or more viral structural proteins, or fragments or derivatives thereof, linked to a protein, wherein the protein is a protease and a fusogenic protein, or fragment or derivative thereof to the target cell, and contacting the target cell with the first and second VLP, wherein the protease from the second VLP recognizes the protease cleavage site from the first VLP and releases the protein, thereby delivering one or more proteins to the target cell.

The present invention also features a method of delivering one or more proteins to a cell comprising providing a first VLP comprising one or more viral structural proteins, or fragments or derivatives thereof, wherein a binding domain is linked to the one or more viral structural proteins and a protease cleavage site is linked to the protein, and a fusogenic protein, or fragment or derivative thereof to the target cell, providing a second VLP comprising one or more viral structural proteins, or fragments or derivatives thereof, linked to a protein, wherein the protein is a protease and a fusogenic protein, or fragment or derivative thereof to the target cell; and contacting the target cell with the first and second VLP, wherein the protease from the second VLP recognizes the protease cleavage site from the first VLP and releases the protein, thereby delivering one or more proteins to the cell.

Protein Delivery-Tus

Transient gene expression in mammalian cells is intensively used for generation of recombinant proteins. However, the principles behind DNA transfer to the cells and the cellular events that ultimately dictate protein expression levels are poorly understood. PE1(polyethylenimine) is a cost-effective transfection reagent that has been reported many times as one of the most efficient cationic compound for in vitro delivery of plasmid DNA into mammalian cells. In addition, a variety of commercially available cationic lipids are used to deliver plasmids into mammalian cells for protein expression.

To express proteins, nuclear translocation of plasmids is essential for transcription to occur in the nucleus. How nuclear translocation of proteins occurs is not well characterized, and it is believed to be one of the major obstacles to high transfection efficiency. Most studies on transfection are focused on designing better in vivo delivery systems for therapeutic applications, and as such, less effort is dedicated toward optimization of recombinant protein production.

The inventors of the instant application have shown that Tus, an *E. coli* replication fork protein when fused to green fluorescent protein (GFP), the full-length fusion protein is localized to the nucleus upon expression in mammalian cells, thus suggesting that Tus contains an NLS (nuclear localization signal).

The Tus protein (*E. coli* DNA replication terminus site binding protein) terminates replication of DNA in *E. coli* and consists of two α-helical bundles at the amino and carboxy termini, connected by a large β-sheet region and binds DNA as a monomer. The DNA-binding region of the Tus family is made of four antiparallel β strands which links the amino- and carboxy-terminal domains and produces a large central cleft in the protein. The DNA is bound in this cleft, with the inter-domain β strands contacting bases in the major groove. DNA backbone contacts are provided by the whole protein. The β strands are positioned almost perpendicular to the base edges in the groove, enabling contacts from amino acids that expose their side chains on either face of the sheet (Kamada et al. (1996) Nature 383, p 598-603).

The tus gene is located immediately adjacent to the TerB site. The Tus DNA-binding protein comprises 309 amino acids (35.8 kilodaltons) that have no apparent homology to the helix-turn-helix, zinc finger, or leucine zipper motifs of other DNA-binding proteins. Binding of Tus arrests DNA replication at the second base pair of the Ter site by preventing DNA unwinding by the DnaJ3 helicase. The equilibrium binding constant ($K_D$) for the Tus DNA binding protein is 0.34 μM. The half life of a Tus-DNA complex is about 550 min., with a dissociation rate constant of 2.1-7.7× $10^{-5}$ $s^{-1}$ and an association rate constant of 1.0-1.4×$10^{-8}$ $M^{-1}$ $s^{-1}$ (Gottlieb et al. (1992) J. Biol. Chem. 267, p 7434-7443 and Skokotas et al., (1995) J Biol. Chem. 29; 270(52):30941-8).

The full length sequence of TUS is encoded NCBI Accession No. AAC74682, represented by the amino acid sequence set forth in SEQ ID NO:1, shown below:

```
                                                    SEQ ID NO: 1
  1  marydlvdrl  nttfrqmeqe  laifaahleq  hkllvarvfs  lpevkkedeh  npinrievkq 61  hlgndaqsla  lrhfrhlfiq  qqsenrsska  avrlpgvlcy  qvdnlsqaal  vshiqhinkl 121  kttfehivtv  eselptaarf  ewvhrhlpgl  itlnayrtlt  vlhdpatlrf  gwankhiikn 181  lhrdevlaql  ekslksprsv  apwtreewqr  klereyqdia  alpqnaklki  krpvkvqpia 241  rvwykgdqkq  vqhacptpli  alinrdngag  vpdvgellny  dadnvqhryk  pqaqplrlii 301  prlhlyvad
```

Tus is known bind to a 20 bp DNA sequence, called the ter site in *E. coli* chromosome, with a binding constant of 3-10×$10^{-13}$ M.

The inventors in the instant application have shown that Tus, an *E. coli* replication fork arresting protein, contains separate sequences that function efficiently as NLS and NES in mammalian cell lines. Here, the NLS is encoded by the amino acid sequence that is set forth as SEQ ID NO: 2, shown below.

```
                            (SEQ ID NO: 2)
KLKIKRPVK
```

The NES is encoded by the amino acid sequence that is set forth as SEQ ID NO: 3, shown below.

```
                                       SEQ ID NO: 3
LAIFAAHLEQHKLLVARVFSL
```

In certain cases, the sequences may comprise certain substitutions, insertions or deletions, such that the sequences still maintain their biological activity that is the activity of a NLS or NES.

For example an isolated polypeptide of the present invention is a homologue of the at least one of the polypeptides set forth as SEQ ID NO: 1, SEQ ID NO: 2, or SEQ ID NO: 3 (e.g., comprises an amino acid sequence at least about 30-40% identical, advantageously about 40-50% identical, more advantageously about 50-60% identical, and even more advantageously about 60-70%, 70-80%, 80-90%, 90-95% or more identical to the amino acid sequence of SEQ ID NO: 1, SEQ ID NO: 2, or SEQ ID NO: 3, and has an activity that is substantially similar to that of the polypeptide encoded by the amino acid sequence of SEQ ID NO: 1, SEQ ID NO: 2, or SEQ ID NO: 3, respectively.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) Nucleic Acids Research 25(17): 3389-3402. When utilizing BLAST and Gapped BLAST programs, the default parameters of the respective programs (e.g., XBLAST and NBLAST) can be used. See ncbi.nlm-.nih.gov. Another particular, non-limiting example of a mathematical algorithm utilized for the comparison of sequences is the algorithm of Myers and Miller (1988) Comput Appl Biosci. 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another embodiment, the percent identity between two amino acid sequences can be determined using the GAP program in the GCG software package, using either a Blossom 62 matrix or a PAM250 matrix, and a gap weight of 12, 10, 8, 6, or 4 and a length weight of 2, 3, or 4. In yet another embodiment, the percent homology between two nucleic acid sequences can be accomplished using the GAP program in the GCG software package (available at gcg.com), using a gap weight of 50 and a length weight of 3.

A convenient method to deliver proteins into cells would have wide ranging applications in cell biology including gene therapy and targeted killing of tumors. The objective of gene therapy was the delivery of genes through plasmids and concomitant expression of proteins that either possess a therapeutic activity or induce an altered cellular phenotype. However, the amount of protein synthesized is largely dependent on the ability of the cell of interest to express the protein.

Other alternative methods to deliver native proteins include microinjection, which is time and labor intensive, or complexing the protein with lipids, which is inefficient and often toxic to cells.

To address some of these issues, an emerging technology called "protein transduction" emerged. This process relies on the inherent property of a small number of proteins and peptides (protein transduction domains, PTDs or cell penetrating peptides) of being able to penetrate the cell membrane. The transducing property of these molecules can be conferred upon proteins which are expressed as fusions. Three of the most commonly used protein transduction vehicles; the antennapedia peptide, the herpes simplex virus VP22 protein and HIV TAT protein transduction domain.

A consideration of PTD mediated protein delivery is that <1% of PTD-fused proteins is released from the endosomes and the rest of the protein remains trapped and unavailable.

Accordingly, the present invention considers novel methods to deliver protein to cells using Tus, and nuclear localization signals that have been discovered in Tus by the inventors of this application.

In one aspect, the invention features a plasmid comprising a nucleic acid molecule that comprises a sequence encoding at least a portion of SEQ ID NO: 1 and a sequence encoding a protein of interest.

In another aspect, the invention features a plasmid comprising a nucleic acid molecule that comprises a sequence encoding at least a portion of SEQ ID NO: 2 and a sequence encoding a protein of interest.

In another aspect, the invention features a plasmid comprising a nucleic acid molecule that comprises a sequence encoding at least a portion of SEQ ID NO: 3 and a sequence encoding a protein of interest.

It is preferable that, in certain embodiments, the plasmid comprises a promoter suitable for expression in a mammalian cell.

A cell that comprises the plasmid as described herein is featured in certain examples. The cell can be in vitro or in vivo, or ex vivo.

Accordingly, the invention features a method of targeting one or more proteins to a cell comprising contacting the cell with a nucleic acid molecule that comprises a sequence encoding at least a portion of SEQ ID NO: 1 or SEQ ID NO: 2, and a sequence encoding a protein of interest, thereby targeting one or more proteins to a cell.

Also featured are methods of transporting one or more proteins into a cell comprising contacting the cell with a nucleic acid molecule that comprises a sequence encoding at least a portion of SEQ ID NO: 1 or SEQ ID NO: 2, and a sequence encoding a protein of interest, thereby transporting one or more proteins into the cell.

In certain cases, the sequences may comprise certain substitutions, insertions or deletions, such that the sequences still maintain their biological activity.

In certain examples, the protein is targeted to the nucleus.

In certain cases, using the methods as described herein the protein is transported to the nucleus.

By delivering the protein(s) to a cell in this way, the methods provided herein may be an efficient means to improve recombinant protein (e.g. both therapeutic and general) expression in cells, particularly, for example, mammalian cells. The methods have unlimited applications, including targeted delivery of therapeutic proteins to combat even solid tumors. Moreover, the methods may be amenable to ex vivo application in stem cells expansion for transplantation.

As described herein Tus has both nuclear localization signal and a nuclear export signal. Using the Tus, it might be possible to conditionally keep essential cytoplasmic proteins out of cytoplasm upon fusion with Tus, as most will be retained in nucleus. Also, using the NES, it may be possible to keep essential nuclear protein in the cytoplasm when fusion made with NES of Tus.

Protein Therapy

Protein therapy involves the delivery of proteins to cells to achieve a therapeutic effect. Typically the cell will be deficient in the therapeutic protein. By deficient it is meant that the cell does not have sufficient quantities of correctly functioning protein. This may mean that the cell does not express the protein at all but it may also mean that the cell expresses a mutated version of the protein. Through delivery of therapeutic amounts of the protein to a cell deficient in the protein the disease state induced by the deficiency may be reversed.

Any protein of therapeutic value to the practitioner is of use in the instant invention.

Provided herein are methods of providing protein therapy to a cell comprising providing a first VLP comprising one or more viral structural proteins, or fragments or derivatives thereof, linked to a protein, wherein a protease cleavage site is linked to the protein and a fusogenic protein, or fragment or derivative thereof to the target cell providing a second VLP comprising one or more viral structural proteins, or fragments or derivatives thereof, linked to a protein, wherein the protein is a protease and a fusogenic protein, or fragment or derivative thereof to the target cell; and contacting the target cell with the first and second VLP, wherein the protease from the second VLP recognizes the protease cleavage site from the first VLP and releases the protein thereby providing protein therapy to the cell.

Also featured are methods of providing protein therapy to a cell comprising providing a first VLP comprising one or more viral structural proteins, or fragments or derivatives thereof, wherein a binding domain is linked to the one or more viral structural proteins and a protease cleavage site is linked to the protein, and a fusogenic protein, or fragment or derivative thereof to the target cell providing a second VLP comprising one or more viral structural proteins, or fragments or derivatives thereof, linked to a protein, wherein the protein is a protease and a fusogenic protein, or fragment or derivative thereof to the target cell; and contacting the target cell with the first and second VLP, wherein the protease from the second VLP recognizes the protease cleavage site from the first VLP and releases the protein; thereby providing protein therapy to the cell.

Protein therapy can be achieved using the *E. coli* Tus protein, NLS, or NES as described herein.

Accordingly, the invention features a method of providing protein therapy to a target cell comprising contacting the cell with a nucleic acid molecule that comprises a sequence encoding at least a portion of SEQ ID NO: 1 and a sequence encoding a protein of interest, thereby providing protein therapy to the target cell.

The invention also features a method of providing protein therapy to a target cell comprising contacting the cell with a nucleic acid molecule that comprises a sequence encoding at least a portion of SEQ ID NO: 2 and a sequence encoding a protein of interest, thereby providing protein therapy to the target cell.

The invention also features a method of providing protein therapy to a target cell comprising contacting the cell with a nucleic acid molecule that comprises a sequence encoding at least a portion of SEQ ID NO: 3 and a sequence encoding a protein of interest, thereby providing protein therapy to the target cell.

Cell Differentiation

One application of protein delivery by is manipulation of pluri-potent stem cells to differentiate to desired cell lineage by delivering required proteins. In certain embodiments. VLPs can be used to deliver proteins to effect cell differentiation.

Accordingly, featured in the invention are methods of promoting differentiation of a cell comprising providing a first VLP comprising one or more viral structural proteins, or fragments or derivatives thereof, wherein a binding domain is linked to the one or more viral structural proteins and a protease cleavage site is linked to the protein, and a fusiogenic protein, or fragment or derivative thereof to the target cell, providing a second VLP comprising one or more viral structural proteins, or fragments or derivatives thereof, linked to a protein, wherein the protein is a protease and a fusiogenic protein, or fragment or derivative thereof to the target cell; and contacting the target cell with the first and second VLP, wherein the protease from the second VLP recognizes the protease cleavage site from the first VLP and releases the protein, thereby promoting differentiation of the cell.

In preferred embodiments, contacting is defined as any method of cell transfection that is known by one of skill in the art. In further embodiments, the contacting occurs simultaneously, that is the cell is contacted with one, two, three or more VLPs at the same time.

Delivery may be to a cell in vivo, in vitro or ex vivo. The cell may be in isolation, in culture with other cells or in situ in a tissue.

IV. Methods of Treating Disease

The invention further provides methods for treating, preventing and/or attenuating diseases or conditions in a subject.

Treating a disease or disorder can be accomplished, in certain examples, by providing one or more VLPs as described herein to the cell, and contacting the target cell with the one or more VLPs, and thereby treating a disease or disorder in a subject.

In other examples, the invention provides methods for treating or preventing a disease or disorder in a subject comprising providing a first VLP comprising one or more viral structural proteins, or fragments or derivatives thereof, linked to a protein, wherein a protease cleavage site is linked to the protein and a fusiogenic protein, or fragment or derivative thereof to the target cell, providing a second VLP comprising one or more viral structural proteins, or fragments or derivatives thereof, linked to a protein, wherein the protein is a protease and a fusiogenic protein, or fragment or derivative thereof to the target cell; and contacting the target cell with the first and second VLP, wherein the protease from the second VLP recognizes the protease cleavage site from the first VLP and releases the protein, thereby treating or preventing a disease or disorder in a subject.

Treating a disease or disorder can be accomplished, in other certain examples, by contacting the cell with a nucleic acid molecule that comprises a sequence encoding at least a portion of SEQ ID NO: 1, SEQ ID NO: 2 or SEQ ID NO: 3 and a sequence encoding a protein of interest, thereby treating or preventing a disease or disorder in a subject.

Contacting the cell can be by any form of transfection that is known to one of skill in the art.

For any of the methods as described above, one skilled in the art will readily understand how these therapeutic techniques can be applied to in vitro scenarios and thus the invention is of great utility as a in vitro research tool for the delivery of proteins of interest to experimental systems.

V. Pharmaceutical Compositions

The mode of administration of the VLP in any of the methods as described herein will vary depending on the disease being treated since different diseases will require administration of the VLP at different sites in the body. For instance treatment of a pulmonary disease or disorder is likely to involve administration to the airway epithelium of the respiratory tract.

Typically the VLP will be administered in a pharmaceutically acceptable composition.

The present invention therefore also provides a pharmaceutical composition comprising a VLP as defined above together with at least one pharmaceutically acceptable carrier, diluent or excipient.

In preferred embodiments, the invention features a pharmaceutical composition comprising one or more of the VLPs as described herein, in combination with a pharmaceutically acceptable carrier, diluent or excipient.

As would be understood by one of ordinary skill in the art, when compositions of the invention are administered to an animal, they can be in a composition which contains salts, buffers, adjuvants or other substances which are desirable for improving the efficacy of the composition. Examples of materials suitable for use in preparing pharmaceutical compositions are provided in numerous sources including REMINGTON'S PHARMACEUTICAL SCIENCES (Osol, A, ed., Mack Publishing Co., (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The VLP in such compositions may comprise from 0.05% to 99% by weight of the formulation, more preferably 0.1% to 10%.

Alternatively the VLP (or composition) may be administered to cells ex vivo prior to implantation or re-implantation. One application, for instance, could be the transfer of growth factor receptors to stem cells to confer upon them the capacity of multiplication and expansion in vitro before re-administration to the patients from whom they were obtained.

Stem cell growth ex vivo is a difficult process, as the cultures usually stabilize at a plateau level of about $3 \times 10^9$ cells, at which they stop dividing. By transferring a growth factor receptor to plateauing stem cells using the protein transfer method of the invention these cells could be induced to proliferate further.

Another application would be the transfer of specific immunogenic proteins (e.g. tumor antigens) to dendritic cells (DC) ex vivo, using the intracellular protein delivery method of the invention, so that these antigens will be processed into immunogenic peptides and expressed at the cell surface by MHC-class II molecules. MHC-class II presentation of these immunogenic peptides will induce or re-enforce the immune response to tumor cells when treated-DC are re-administrated in vivo.

Yet another ex vivo application of consists of transferring tissue-specific cell surface molecules to stem cells isolated from a patient to ensure retargeting of the stem cells to specific organs upon systemic administration.

As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

The compositions of the present invention can be administered by various methods known in the art. The particular mode selected will depend of course, upon the particular composition selected, the severity of the condition being treated and the dosage required for therapeutic efficacy. The methods of the invention, generally speaking, can be practiced using any mode of administration that is medically acceptable, meaning any mode that produces effective levels of the active compounds without causing clinically unacceptable adverse effects. Such modes of administration include oral, rectal, parenteral, intracisternal, intravaginal, intraperitoneal, topical (as by powders, ointments, drops or transdermal patch), bucal, or as an oral or nasal spray. The term "parenteral" as used herein refers to modes of administration which include intravenous, intramuscular, intraperitoneal, intrasternal, subcutaneous and intraarticular injection and infusion. The composition of the invention can also be injected directly in a lymph node.

Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyloleate. Carriers or occlusive dressings can be used to increase skin permeability and enhance antigen absorption.

Combinations can be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Dosage levels depend on the mode of administration, the nature of the subject, and the quality of the carrier/adjuvant formulation. Typical amounts for VLPs, are in the range of about 0.001 ug to about 20 mg per subject. Preferred amounts are at least about 10 ug to about 500 ug per subject. Multiple administration may be preferred, in certain cases, and protocols are those standard in the art adapted to the subject in question.

The compositions can conveniently be presented in unit dosage form and can be prepared by any of the methods well-known in the art of pharmacy. Methods include the step of bringing the compositions of the invention into association with a carrier which constitutes one or more accessory ingredients.

Compositions suitable for oral administration can be presented as discrete units, such as capsules, tablets or lozenges, each containing a predetermined amount of the compositions of the invention. Other compositions include suspensions in aqueous liquids or non-aqueous liquids such as syrup, an elixir or an emulsion.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art.

Other embodiments of the invention include processes for the production of the compositions of the invention and methods of medical treatment for diseases such as cancer, inflammatory diseases, cardiovascular diseases, apoptotic disorders, aging diseases, and allergies using said compositions.

VI. Kits

In yet another aspect, the invention provides kits.

Kits of the invention can comprise the VLP of any one of the aspects as described herein, and a host cell line.

In certain aspects, kits of the invention can comprise the plasmid comprising the VLP as described herein, and a host cell line. Kits of the invention can also comprise, a first plasmid comprising a nucleic acid sequence encoding one or more viral structural proteins, or fragments or derivatives thereof, linked to a nucleic acid sequence encoding a protein of interest; and a second polypeptide comprising a nucleic acid sequence encoding one or more viral structural proteins, or fragments or derivatives thereof, linked to a nucleic acid sequence encoding a protease, and a second plasmid comprising a nucleic acid sequence encoding a fusogenic protein, and instructions for use for making a VLP.

In certain examples, the kits can comprise a first plasmid comprising one or more viral structural proteins, or fragments or derivatives thereof, linked to a protein and a second plasmid comprising a fusogenic protein, or fragment or derivative thereof, and instructions for use for making a VLP. In other examples, the kits can comprise one or more viral structural proteins, or fragments or derivatives thereof, wherein one or more of a cleavage site or a binding domain is linked to the one or more viral structural proteins and a protease cleavage site is linked to the protein and a second plasmid comprising a fusogenic protein, or fragment or derivative thereof, and instructions for use for making a VLP.

In other examples, the kits can comprise one or more viral structural proteins, or fragments or derivatives thereof, linked to a protein, wherein the protein is a protease, a second plasmid comprising a fusogenic protein, or fragment or derivative thereof, and instructions for use for making a VLP.

Kits of the invention can also feature one or more of SEQ ID NO: 1, 2 or 3 and instructions for use in treating a disease or disorder.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

EXAMPLES

Standard techniques well known in the art or the techniques specifically described below were utilized.

Example 1

Virus Like Particles and In Vitro Delivery to Cells

Virus like particles (VLPs) are retroviral particles that are devoid of genomic RNA and envelope. In the examples described herein, the VLP is used in a novel way to deliver biologically active proteins into target cells.

Figure 1A:
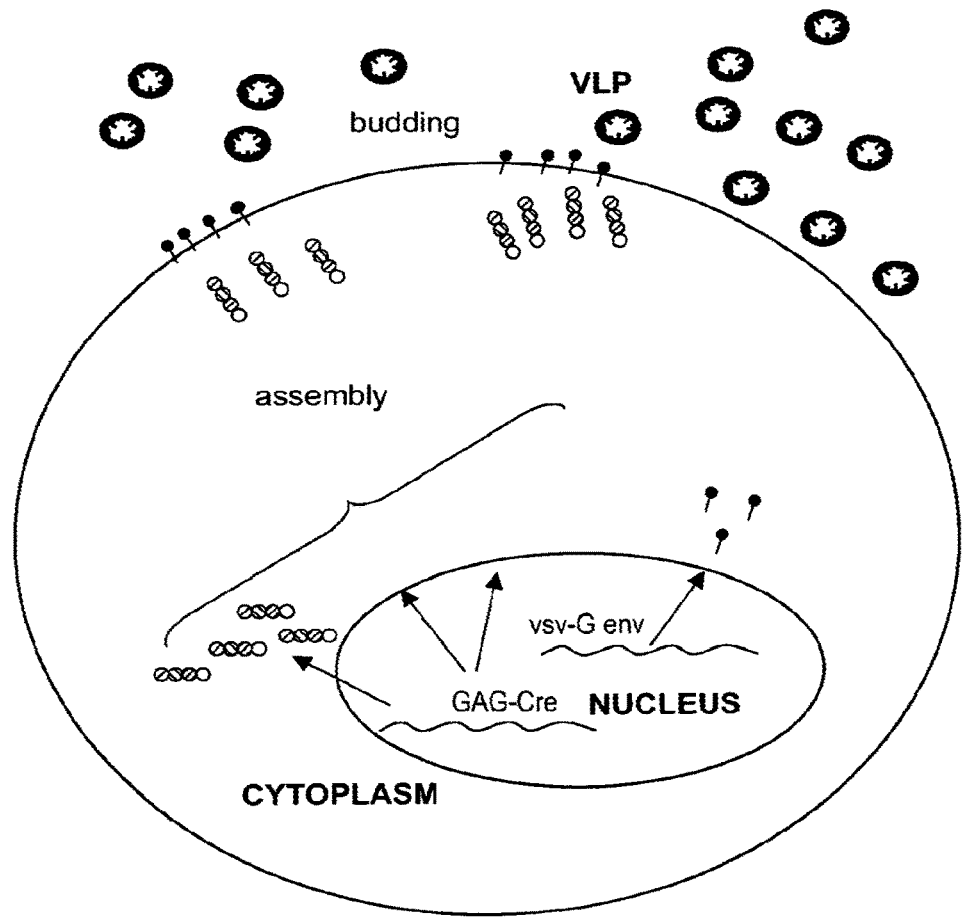
FIGS. 1(a-c) are schematics that illustrate the concept of the VLP technology according to preferred embodiments of the present invention. (a) shows generation of a Cre recombinase containing VLP in 293T cell line. (b) shows a VLP containing different proteins as a GAGfusion. (c) shows transduction of a PC3 reporter cell line with a VLP containing GAG–Cre recombinase as the GAG-protein of interest (POI).
Figure 1B:
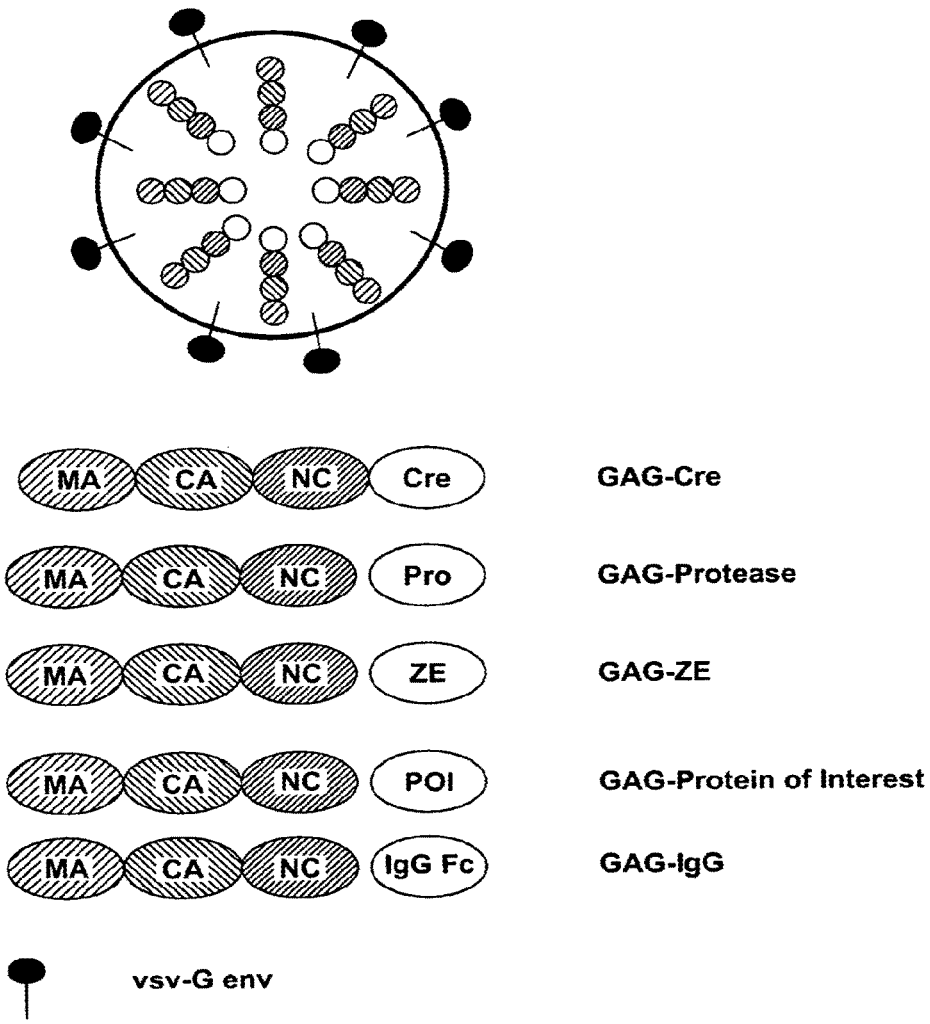

There are three components of VLPs to deliver proteins. The concept of the technology as exemplified in preferred embodiments of the present invention is shown in FIGS. 1(a-c). In certain preferred embodiments, and as exemplified in these experiments, the protein to be delivered is fused as GAG poly-protein. FIGS. 1(a-c) are schematics that illustrate the concept of the VLP technology according to preferred embodiments of the present invention. (a) shows generation of a Cre recombinase containing VLP in 293T cell line. (b) shows a VLP containing different proteins as a Gag fusion. (c) shows transduction of a PC3 reporter cell line with a VLP containing GAG–Cre as the GAG-protein of interest (POI).

In a first set of experiments, VLPs were generated. A 293T cell line was transfected with two plasmids, one expressing GAG-fusion-protein of interest (GAG-POI) and the other plasmid expressing retroviral envelope (preferably, but not limited to, VSV–G or ASLV envA envelope) which targets VLP protein to a target cell. The GAG could be derived from murine, avian, or human retrovirues. VLP attachment to the target cell occurs via specific cellular receptor expressed on the cell surface, and as a result the VLP is endocytosed into the cell interior. The process of endocytosis allows internalization of VLP into endosomal compartments where upon a pH change (from pH 7.4 to pH 5.5) in the endosomal compartment, the pH dependent fusion of VLP and endosomal membranes takes place, resulting in delivery of VLP core particles to the cytosol. The disassembly of cores in the cytosol liberates GAG-POI, allowing the POI to effect its biological activity.

The expression of protein of interest as part of GAG-fusion can sometimes compromise biological activity of POI. In order to maintain biological activity of POI, chimeric VLPs consisting of GAG-POI and GAG-protease co-packaged at 10:1 molar ratio to the same VLP have been generated. Upon maturation of VLPs, protease cleaves all GAG components resulting in the generation of native POI. In these VLPs the cargo protein was successfully processed and was delivered to its target—the cellular nucleus—as biologically active Cre recombinase. This is shown in FIG. 5. FIG. 6 shows processing of GAG and GAG–Cre fusion in the presence of protease.

In another set of experiments, VLPs are generated containing Cre recombinase as GAG–Cre fusion protein. These experiments can serve as proof of principle experiments. Here, the VLPs were used to transduce reporter cell lines. Biologically active GAG–Cre protein has been detected in the transduced reporter cell line using VLPs made with the fusion, suggesting Gag that biologically active Cre (FIG. 1c).

This described technology for tissue specific delivery of active proteins can be exploited for site specific or organ specific protein delivery as a single protein module or as multi-protein modules. This technology is very flexible for further modification.

Figure 2A:
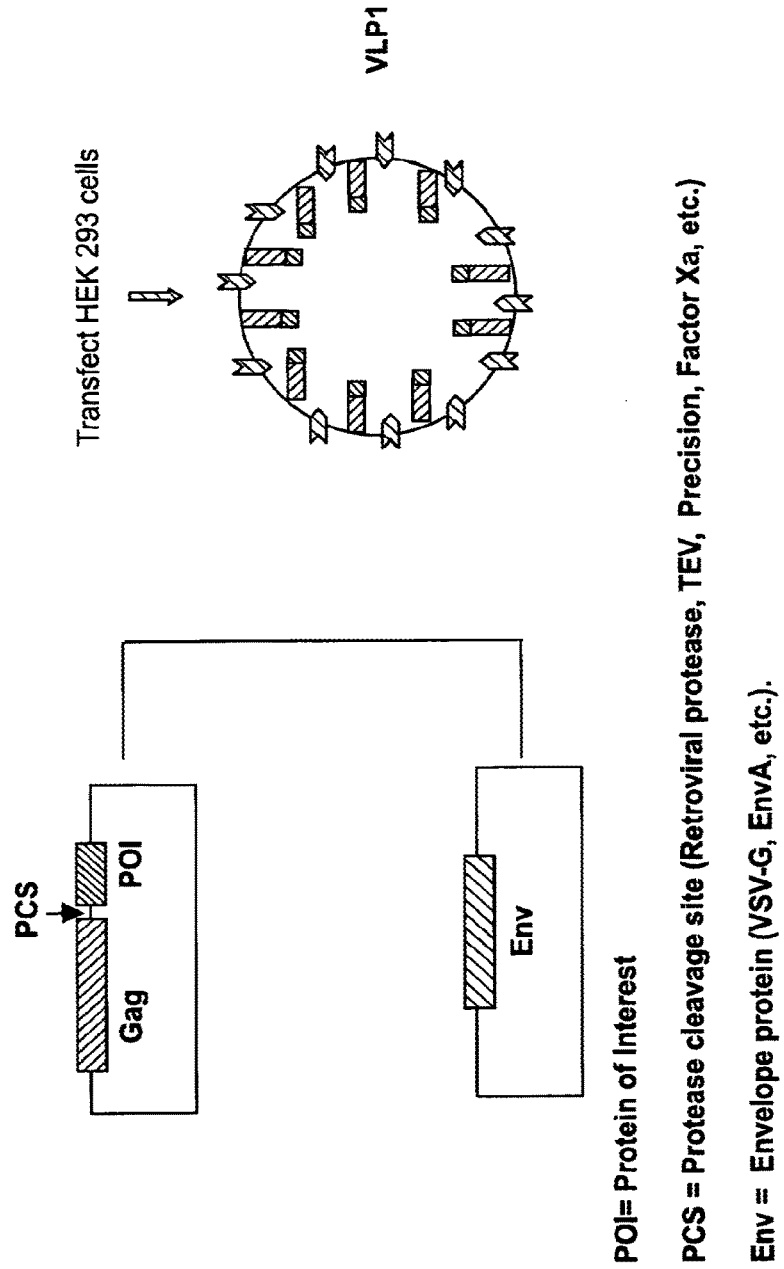
FIGS. 2 (a-c) illustrates various VLPs of the invention. (a) shows plasmid components needed to make VLP1. (b)
Figure 2B:
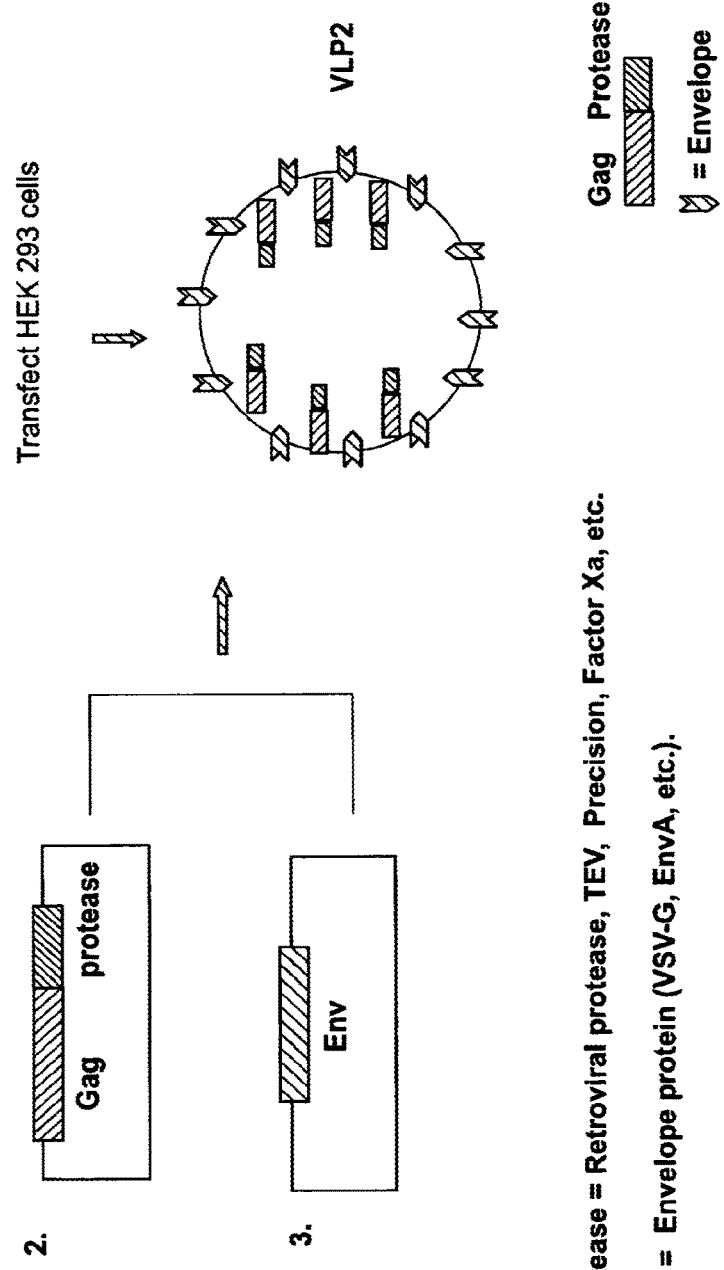
Figure 2C:
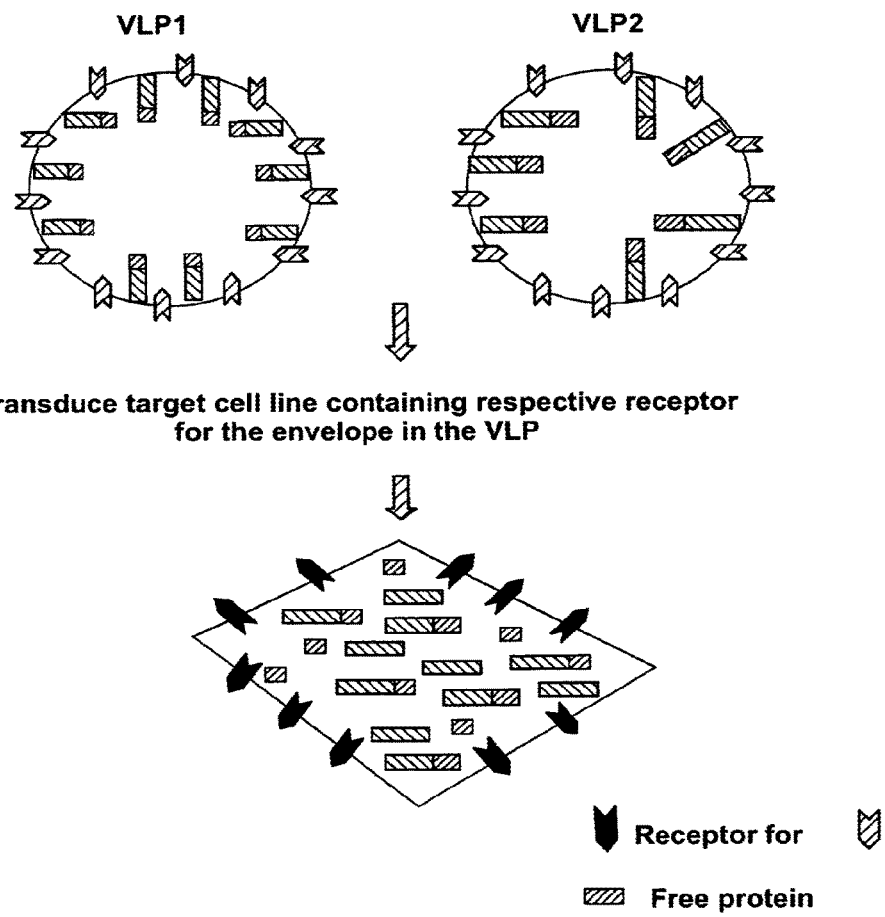

In some examples, the therapeutic application of fusion proteins may be compromised by low biological activity of the protein as fusion with Gag may interfere with the biological activity. In those situations, the passenger or the cargo proteins may need to be separated from the fusion. Accordingly, there are several ways cargo proteins can be removed from the fusion partner. One possibility is to make one VLP population (VLP1) consisting of Gag-protease cleavage site-protein of interest (FIG. 2a). The second VLP (VLP2) would consist of Gag-protease fusion (FIG. 2b). The protease in VLP2 should be specific for the cleavage site introduced in the other fusion construct (FIG. 2a). The target cells or organs are simultaneously transduced with both VLPs (VLP1 and VLP2) resulting in delivery of therapeutic protein processed in target site by the specific protease (FIG. 2c).

Figure 3D:
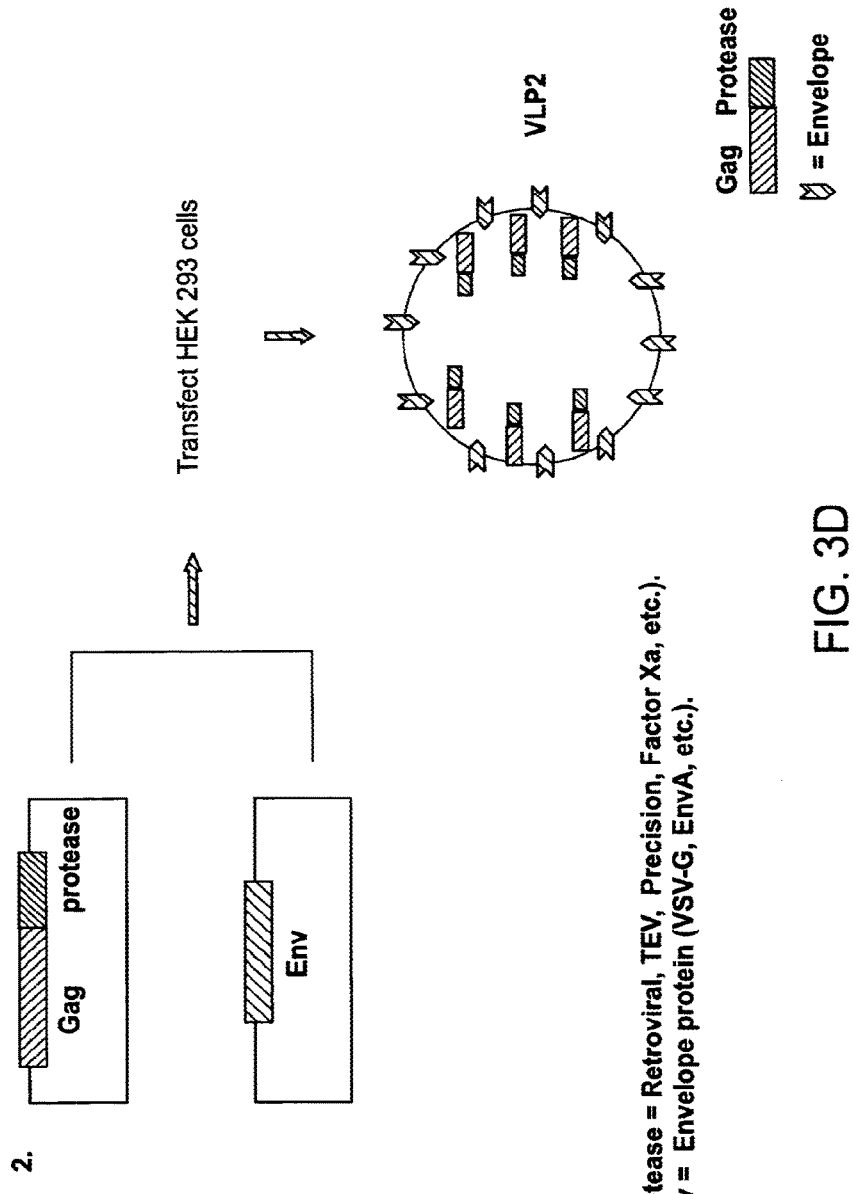

Another possibility is to generate VLPs capable of packaging therapeutic proteins (as the proteins of interest) containing affinity tags, such as Fc region of IgG or one component of leucine zipper, for example ZE or ZR (Moll et al. Protein Science 2001, 10:649-655). This approach also delivers two VLP modules. The first module (VLP1) consists of an expression vector coding for VLPs, where the GAG-Fc region of IgG (FIG. 3a) or ZE (FIG. 3b) is expressed as a fusion protein. The purpose of the Fc region of IgG or ZE is to provide an anchor for the affinity tagged protein of interest with the respective partner, protein A or ZR, respectively (FIG. 3c A and FIG. 2c B). The second module (VLP2) consists of VLP containing GAG-TEV protease fusion protein (FIG. 3d and FIG. 2c). The target cells or organs are simultaneously transduced with both VLPs (VLP1 and VLP2) resulting in delivery of therapeutic protein processed in target site by TEV protease (FIG. 3e). The Gag or structural protein could be suitably derived from murine, avian, human or any other species. It could be full length or could be a deletion version capable of packaging into virus like particle. The protease could be TEV, Precision or Factor Xa or any other proteases. Exemplary VLPs for use in vivo studies are shown in FIG. 4. FIGS. 4 (a and b) are schematics, where (a) shows generation of the GAG–Cre VLP used for in vivo studies and (b) is a schematic of the in vivo studies using VLPs.

FIG. 5 shows GAG–Cre fusion and processed Cre activity in PC3 cell line. The expression of the POI as part of GAG-fusion can sometimes compromise biological activity of POI. In order to maintain biological activity of POI, chimeric VLPs have been generated consisting of GAG-POI and GAG-protease co-packaged at 10:1 molar ratio to the same VLP. Upon maturation of VLPs, protease cleaves all GAG components resulting in the generation of native POI. In these VLPs the cargo protein was successfully processed and was delivered to its target—cellular nucleus as biologically active Cre recombinase. FIG. 6 shows processing of GAG and GAG–Cre fusion in the presence of protease. VLPs were probed with anti-p27 (Ca of GAG) and anti-Cre. The processed Gag (p27) can be observed only where VLPs were co-packaged with GAG-Pr (lanes 3 and 4). Lanes 1 and 2 show unprocessed GAG due to absence of protease. On lower panel the processed Cre recombinase is observed only where VLPs were co-packaged with GAG-Protease (lane 3), unprocessed GAG–Cre is observed in lanes 1 and 2.

Delivery of Interferon into Cells.

In one set of experiments, VLPs are generated that consist of GAG, interferon gamma (IFNg), human or mouse. A schematic of an exemplary VLP for use in this method is shown in FIG. 7. In these experiments, the 293T cell line was transduced with VLPs consisting of GAG-IFn-gamma (human or mouse) pseudotyped with VSV-G envelope, and $3.0 \times 10^6$ cells were plated in 10 cm dish (10 ml of DMEM containing 10% FBS) 24 hr before transduction. At the time of transduction fresh complete culture medium was added to cells (total 10 ml supplemented with VLPs (proxy $2 \times 10^6$ VPLs). The flow cytometry assay was performed 1 hr post-transduction. The results are shown in FIG. 8.

Delivery of Cytotoxic Enzymes that Convert Pro-Drug into Active Drug into Cells.

In another set of experiments, VLPs are generated to deliver cytotoxic enzymes and to test effectiveness of GAG-fusion-Fcy::Fur in the cell killing process. Fcy and Fur enzymes convert pro-drug 5FC into cell toxic 5FU. The VLPs were pseudotyped with wild type VSV-G as indicated. This is shown in FIG. 9. FIG. 10 shows the results of treatment of 293T cells with VLPs consisting of GAG-Fcy::Fur-/+VSV-G envelope, in dose dependent manner of 5FC. As shown in FIG. 10, an extensive killing of cells was observed where VLPs were pseudotyped with VSV-G envelope. In further experiments, PC3 cells were simultaneously exposed to given VLPs and 5FC and different doses. FIG. 11 shows the results of VLPs mediated cytotoxicity on PC3 (prostate cancer) cell line. FIG. 12 shows the killing of PC3 (prostate cancer cell line) with VLP containing Fcy::Fur in the presence of 5FC.

Mutant VSV-G Envelope Protein.

In another set of experiments, mutant VSV-G proteins were generated. These mutants preferably kept their fusiogenic activity while also having low or no ligand binding activity.

Accordingly, as shown in FIG. 13, VSV-G mutant Cys2 (C2) was generated to keep its fusogenic activity with low or no ligand biding activity. The VSV-G mutant (s) are used for target (ligand) specific delivery of proteins. The VSV-G wild type (w/t) and VSV-G(C2) envelope can be efficiently incorporated into retrovirus. The targeted delivery of VLPs carrying therapeutic or cytotoxic proteins to target cell and organs in vivo would make very attractive method for in vivo therapy. FIG. 14 shows that VSV-G Cys2 mutant has fusogenic activity. FIG. 14 shows that mutant VSV-G (C2) contains non-functional binding domain but functional fusion domain. This mutant was isolated to complement its fusogenic activity with target specific binding mediated by cell specific ligand (protein expressed on VLPs surface). The VSV-G(C2) mutant shown good fusion activity in cell fusion assay at pH 5.14 compared to wild type VSV-G envelope. As seen in FIG. 14, binding to cellular receptor on 293T cells using VSV-G(C2) is very limited, resulting in only fractional infectivity compared to retrovirus pseudotyped with w/t VSV-G envelope. Three independent mutants of Cys 2-2, 4 and 6 were tested.

In preferred embodiments, the mutant VSV-G can be used in a targeted delivery system for therapeutic protein delivery.

Therapeutic protein delivery using lentiviral nanoparticles was recently described (Nucleic Acids Res, 2006 Jan. 30; 34(2):e16). This system relies on three expression plasmids; plasmid coding for GAG-POL-VIFNPR/TAT/VPU, where mutation in POL inactivates POL protein, plasmid coding for VPR-PC-POI (protein of interest) and plasmid coding for envelope (e.g. VSV-G). In this system, fusion protein consisting of VPR-PC (protease cleavage site) POI (protein of interest) is expressed in packaging cell line together with GAG-POL-VIFNPR/TAT/PVU. The co-package of VPR-POI fusion protein with GAG is due to association of VPR with GAG and number of co-packaged VPR-POI particles in VLPs is limited. The system described herein does not contain any retroviral accessory proteins apart from GAG making the system much safer compared to human lentiviral system Targeting Cells Using Haemagglutinin (HA) and Neuraminidase (NA).

Haemagglutinin (HA) and neuraminidase (NA) are two other envelope proteins that can be used for targeted delivery. In other experiments, it was shown that mutated HA of H7 influenza virus can also be used for targeted delivery. It was shown that this mutated for of HA (mtm) envelope results in limited infectivity compared to wild type (w/t) H7 HA envelope. FIG. 15 shows that the fusogenic activity of mutated envelope is as good as w/t. Therefore, this is another potential candidate for complementation with target specific ligand for targeted VLPs delivery.

NA can also be used for targeted delivery. FIG. 16 shows an exemplary VLP containing a protein of interest (POI) psuedotyped with VSV-GC2 (fusion) and NA-Ligand (Target). This schematic illustrates the concept of delivering of VLPs consisting of POI and cell specific targeting ligand through neuraminidase, NA-Ligand, (for targeting) complemented by fusogenic activity of VSV-G (C2) envelope.

In the VLP illustrated in FIG. 17, peptide ligand is expressed on VLP surface as fusion Ligand-HA protein for targeting and VSV-G(C2) for fusion.

Induction of Apoptosis.

In certain cases, VLPs of the invention can be used to induce apoptosis in target cells. FIG. 18 shows the design of VLPs where the protein of interest is a caspase, and in particular the caspase is human caspase 8. Caspases (cysteine-aspartic proteases) are a family of cysteine proteases, which play essential roles in apoptosis, necrosis and inflammation. Caspases exist within the cell as inactive pro-forms or zymogens. These zymogens can be cleaved to form active enzymes following the induction of apoptosis. Induction of apoptosis via death receptors (e.g. FAS, TRAIL) typically results in the activation of an initiator caspase such as caspase 8 or caspase 10.

Further, the VLP comprising the caspase also comprises TRAIL targeting ligand on the VLP surface that is used to target the VLP to cancer cells. Accordingly, in preferred embodiments, the VLP consists of GAG-human Caspase 8 and TRAIL targeting ligand on VLPs surface for delivery to cells over-expressing DR4 (death receptor) and DR5. This type of VLPs will be used to target cancer cells and induce programmed cell death (apoptosis) through TRAIL receptor and Caspase 8 activity in target cells.

It has been previously shown that there is a dramatic cytotoxic effect on PC3 cell line transduced with VLPs consisting of TRAIL ligand on VLPs surface. In order to provoke targeted cell killing in vivo VLPs have been designed where TRAIL ligand is displayed on the surface of the VLP to target cell via DR4 and DR5. These receptors are present only in cancer cells. VLPs have previously been generated that are pseudotyped with w/t of VSV-G envelope protein. These VLPs showed enhanced killing property compared to VLPs displaying TRAIL ligand without VSV-G. It may be possible though that pseudotyping with w/t VSV-G envelope in vivo would have the effect of transducing non-target cells due to the pantropic nature of VSV-G mediated transduction. Thus, to eliminate off target transduction the w/t VSV-G envelope has been modified where cellular receptor binding capacity is decreased by two orders of magnitude but pH dependent fusion capacity (VSV-G(C2) is maintained comparable to w/t VSV-G. In this approach TRAIL ligand directed cell specificity is retained, eliminating pantropic transduction through w/t VSV-G envelope but uncompromised fusion trough VSV-G(C2).

As seen on FIG. 25, transduction of the recipient cell line with VLPs consisting of GAG-GFP+NA-TRAIL+VSV-G (C2) caused over 90% cell death, where s-TRAIL at 100 ng/ml and GAG-GFP+NA-TRAIL caused 60% and 80% cell death respectively. This finding demonstrated usefulness of the VSV-G(C2) envelope for in vivo applications.

Stem Cell Generation and Cell Differentiation

Figure 19:
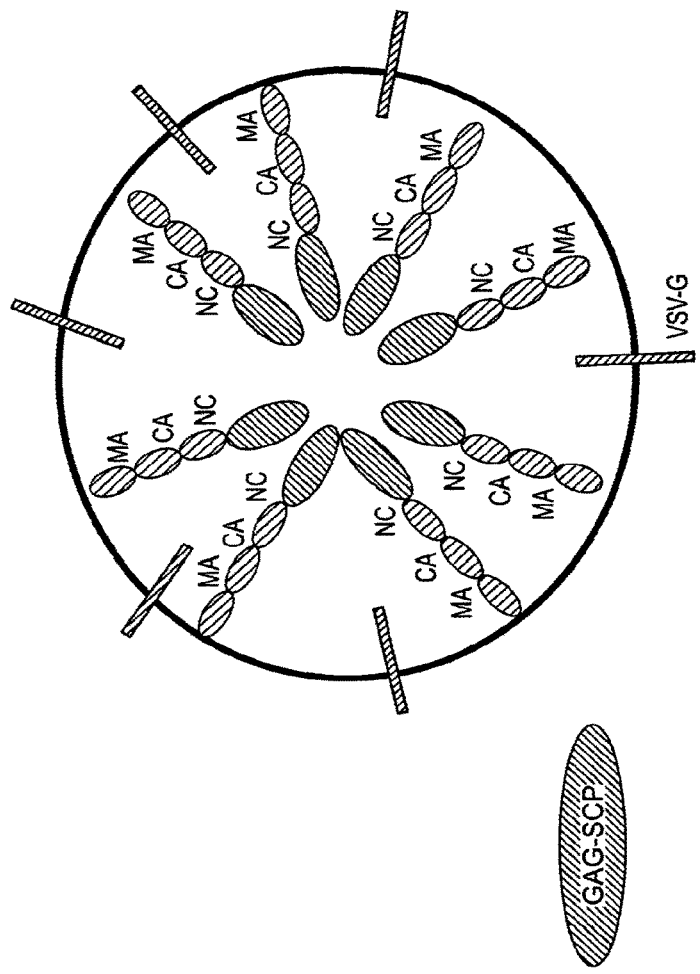

FIG. 19 shows generation of VLPs for generation of i-stem cells. Here, stem cells transcription factors are cloned as GAG-fusion for stem cell generation from fibroblasts. Exemplary stem cell transcription factors include, but are not limited to Oct-3, Oct-4, Fox-D3, Sox2, Nanog, Klf4.

One application of protein delivery by VLPs is manipulation of pluri-potent stem cells to differentiate to desired cell lineage by delivering required proteins. In a recent report, it was shown that human skin cells can be transformed into stem cells by supplying only four proteins into skin cells. The authors used retroviruses with their genetic materials to deliver the proteins. The problem with this delivery is that retroviruses first incorporate themselves into the genome of the host cells. The incorporated retrovirus can pose two problems: first, they can incorporate into essential genes causing inactivation of the function of the gene and second, they can produce cancer later. VLPs do not contain any genomic materials. Thus, all four genes, or any combination of the required genes, can be delivered by different VLPs each containing one protein, and the target cells can be transfected with a mixture of four VLPs resulting in the same stem cells.

Example 2

VLPs for Study of Metastasis and Tissue Specific Gene Delivery In Vivo

Animal models are routinely used as tools for study of cancer etiology and therapy. At present transgene expression or knock out models of cancer established in mice falls short of addressing all aspects of cancer disease: such as initiation, progression and metastatic invasion of cancer. Most of these in vivo models do not generate metastatic tumors. There is immediate need for a simple in vivo model for sensitive detection and possible assessment of therapeutic agents for early detection of tumor initiation and metastatic invasion.

Figure 4A:
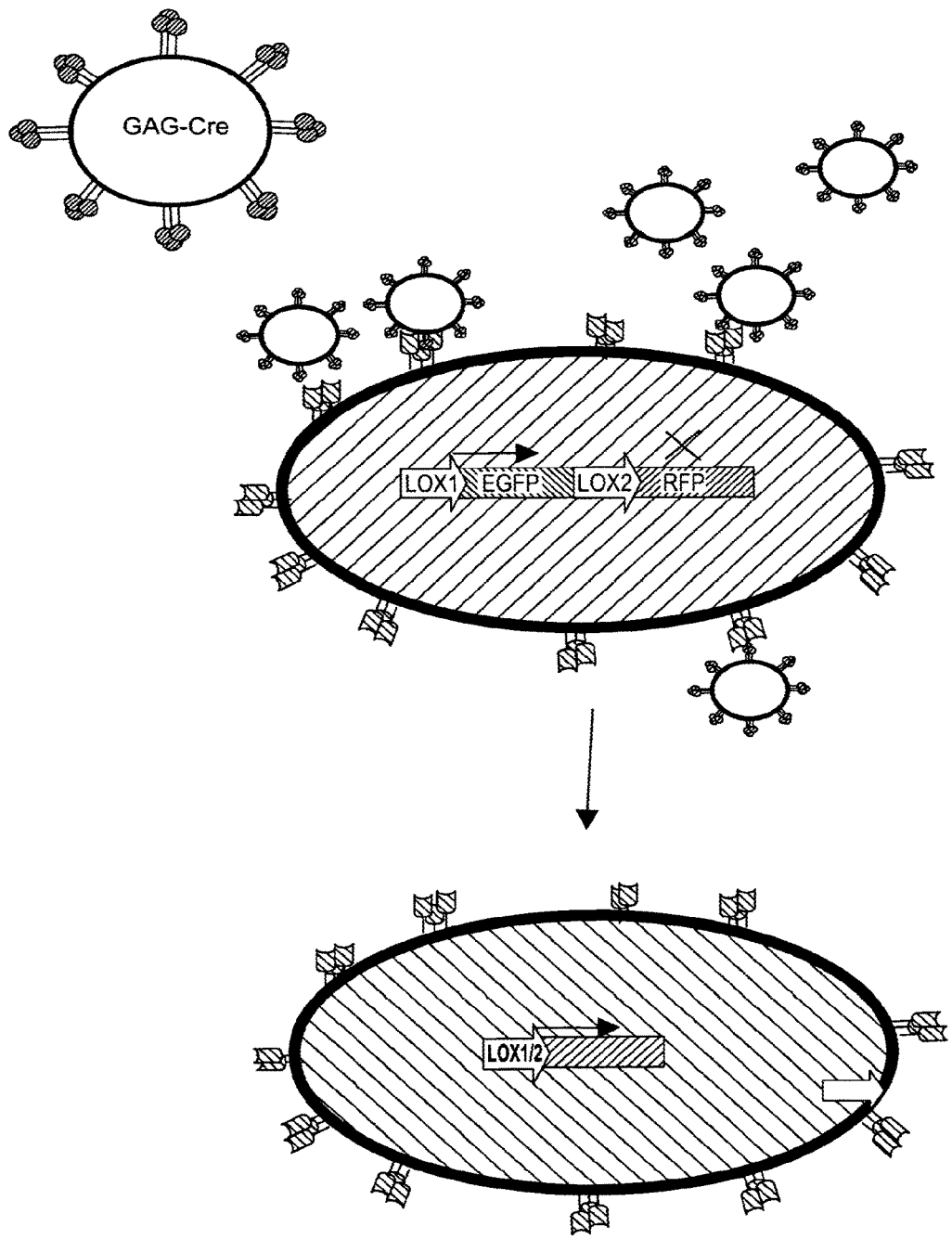
Figure 4B:
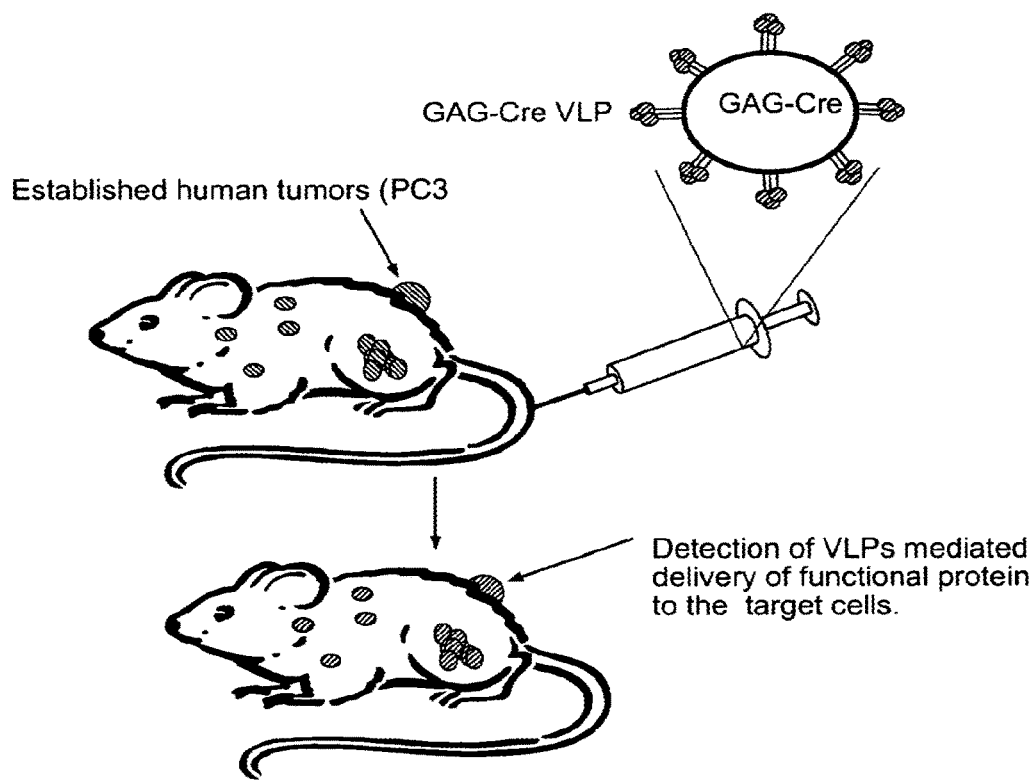

To address this issue, established cell lines derived form human tumors can be used and implanted into immuno-compromised mice to establish tumor growth (FIGS. 4a and 4b). Such tumor bearing animal will be used for experimentation addressing different aspect of cancer research. The human PC3 cell line is derived from carcinoma of prostate after failed antiandrogen chemotherapy. This cell line is androgen receptor insensitive, highly metastatic in nude mice and is an extensively used cell line in cancer research. This cell line can be used as a tool for an in vivo model of early detection of metastatic invasion of primary tumors.

In other embodiments, the invention described herein can be used as a potential organ and cell specific delivery system in vivo using the modified retroviral based VLP delivery system as means of detection for not only primary tumors but also early metastases, and also possible target specific genetic therapy.

One of commonly used delivery vehicles in animal models are retroviral vectors based on murine retroviruses (e.g. mouse Moloney leukemia virus). The advantage of using retroviral vectors is the apparent lack of immune response of host to retroviruses; however the integration of the retroviral genome into recipient host cell represents a potential hazard and it is a potential source of genetic mutations which could cause disease. On the other hand the application of VLPs for therapeutic purposes eliminates the danger of carrying genetic material of retroviruses to target cells, as VLPs are DNA deficient.

Example 3

Tus, an *E. coli* Protein, Contains Mammalian Nuclear Targeting and Export Signals Replication of the circular *E. coli* chromosome starts at the origin of replication (oriC), and proceeds bidirectionally to a region on the opposite side called Ter, where replication is terminated (1, 2). Within the Ter region are found ten short (approximately 20 bp) DNA sequences, called "Ter" sites, which are similar but not identical (3). Binding of Tus, a 35 kDa trans-acting protein, to the Ter sequences blocks movement of the DNA replication complex in an orientation-specific manner: Ter sites (with bound Tus) in the permissive orientation allow the replication complex to pass, whereas Tus/Ter complexes in the non-permissive orientation block its movement (4 and references there in).

The full length sequence of TUS is encoded NCBI Accession No. AAC74682, represented by the amino acid sequence set forth in SEQ ID NO: 1, shown below:

```
                                                              SEQ ID NO: 1
  1  marydlvdrl  nttfrqmeqe  laifaahleq  hkllvarvfs  lpevkkedeh  npinrievkq 61  hlgndaqsla  lrhfrhlfiq  qqsenrsska  avrlpgvlcy  qvdnlsqaal  vshiqhinkl 121  kttfehivtv  eselptaarf  ewvhrhlpgl  itlnayrtlt  vlhdpatlrf  gwankhiikn 181  lhrdevlaql  ekslksprsv  apwtreewqr  klereyqdia  alpqnaklki  krpvkvqpia 241  rvwykgdqkq  vqhacptpli  alinrdngag  vpdvgellny  dadnvqhryk  pqaqplrlii 301  prlhlyvad
```

The binding of Tus to the TerB site, with an observed binding constant ($K_{obs}$) of $3\text{-}10 \times 10^{-13}$M (5), is one of the strongest known DNA-protein interactions involving a monomeric protein. The crystal structure of Tus-Ter complex showed that Tus protein binds duplex DNA tightly through a novel two-domain structure with inter-domain β-strands and cannot be released without a large conformational change of the Tus protein (6). A total of 42 amino acid residues out of the 309 amino acids of Tus interact with the DNA. Of these, 18 residues lie within the β-strands (FGHI), which lie partially within the major groove of the Ter DNA and the remaining 24 residues are dispersed along the Tus protein between amino acids 50 and 302. Alterations of some of amino acids in these domains exhibit partial or complete loss of DNA binding or DNA replication arrest activity (7, 8, 9).

In mammalian cells, active transport of proteins into the nucleus is facilitated by the presence of a nuclear localization signal (NLS) that is recognized by and associated with nuclear import receptors (10, 11, 12, 13). Similarly, nuclear export of proteins is facilitated by the presence of a nuclear export signal (NES), in association with an export receptor, probably CRM-1 (13, 14) in human cells. Although the presence of nuclear targeting sequences are common in mammalian proteins, the widely use Cre recombinase of bacteriophage P1 is the only prokaryotic protein known to contain a sequence that functions as an NLS (15). In addition, VirD2 of *Agrobacterium* also shown to possesses NLS sequence (16). However, there was no report to show that these prokaryotic proteins contain NES in addition to NLS in the same protein. The present experiments demonstrate with GFP fusion constructs that the *E. coli* Tus protein contains both NLS and NES motifs that function efficiently in human cells. Accordingly, Tus may be the first prokaryotic protein known to carry both nuclear import and nuclear export sequences.

Several eukaryotic proteins have the ability to travel through biological membranes. Examples include the HIV-1 TAT protein, the herpes simplex virus 1 (HSV-1) DNA-binding protein VP22, and the *Drosophila* Antennapedia (Antp) homeotic transcription factor (17). The small protein transduction domains (PTDs) from these proteins can be fused to other macromolecules, peptides or proteins to successfully transport them into a cell (17, 18). So far, there have been no examples of any prokaryotic proteins or peptides derived from prokaryotic proteins to do similar function. The present experiments show that full length Tus protein or a peptide (NLS) is capable of transporting proteins into mammalian cells from the culture media.

Nuclear Import of GFP-Tus Fusion

Figure 20A:
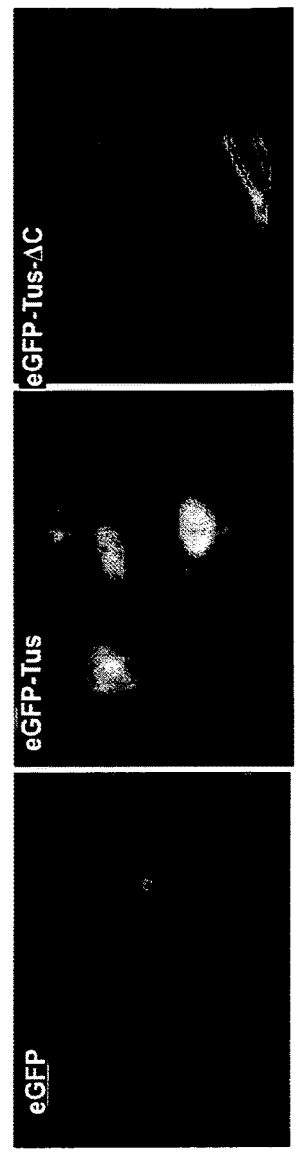
Figure 20B:
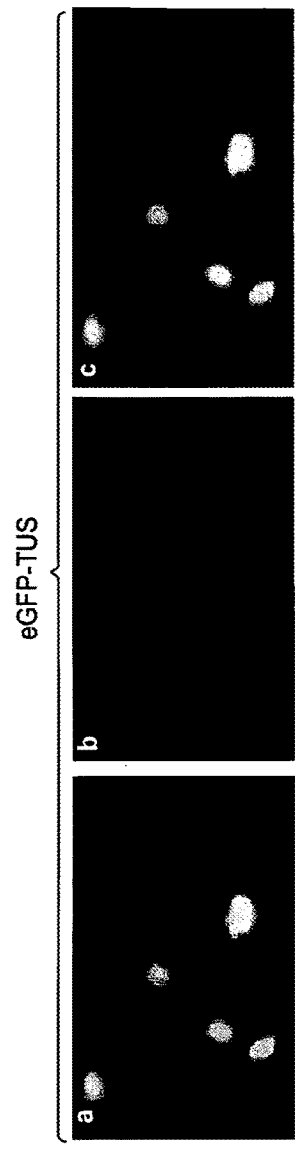

The Tus protein was fused to the carboxy terminus of GFP as described in the Methods section herein. The fusion was made initially as a model to develop a novel protein microarray-on-demand technology. For this purpose, the expression of the GFP fusion in mammalian cells by transient expression was examined. GFP expression alone showed fluorescence distributed throughout the cells (FIG. 20A(a)). In contrast, transfection of PC3 cells with pDest 472-GFP-Tus resulted in strong green fluorescence almost exclusively in the nucleus of the cells (FIG. 20A(b)). In order to conclusively determine nuclear localization of GFP-Tus protein, following transfection cells were examined for green fluorescence as well as DAPI nuclear staining. The results as shown in FIG. 20B clearly suggest that GFP-Tus fusion protein is indeed localized in the nucleus. As Tus is a bacterial protein, specific targeting to the nucleus was unexpected. Nuclear pores in eukaryotic cells consist of channels of 9-10 nm in diameter that might allow smaller proteins (<40 kDa), to diffuse in and out of the nucleus freely, but import of larger proteins is an active process (12). The size of the GFP-Tus fusion protein is about 62 kDa and thus, it would be difficult for this large fusion protein to pass the nuclear membrane by simple diffusion. The result suggests the presence of a nuclear targeting signal in Tus.

Location of Nuclear Localization Signal in Tus

In order to identify the location of the nuclear localization signal (NLS) within Tus, a series of N- and C-terminal deletion mutants of Tus were constructed, which were fused to GFP to determine the subcellular distribution of green fluorescence in the PC3 cell line. Transfection of PC3 cell lines with all of these fusion constructs were performed and the results are summarized FIG. 21A.

The results suggest that fusion of up to 217 amino acids from the N-terminus of Tus protein (full length 309 amino acids) with GFP causes loss of nuclear targeting. However, the fusion of amino acids 218 to 309 of Tus to the C-terminus of GFP restored nuclear targeting. Thus, the nuclear targeting signal must be located within the 92 amino acids at the C-terminus of Tus. Fusion of the Tus fragment corresponding to amino acids 264 to 309 with GFP did not result in nuclear targeting. Therefore, the location of the NLS must be confined within 48 amino acids (218-264) near the carboxy end of Tus.

Figure 22A:
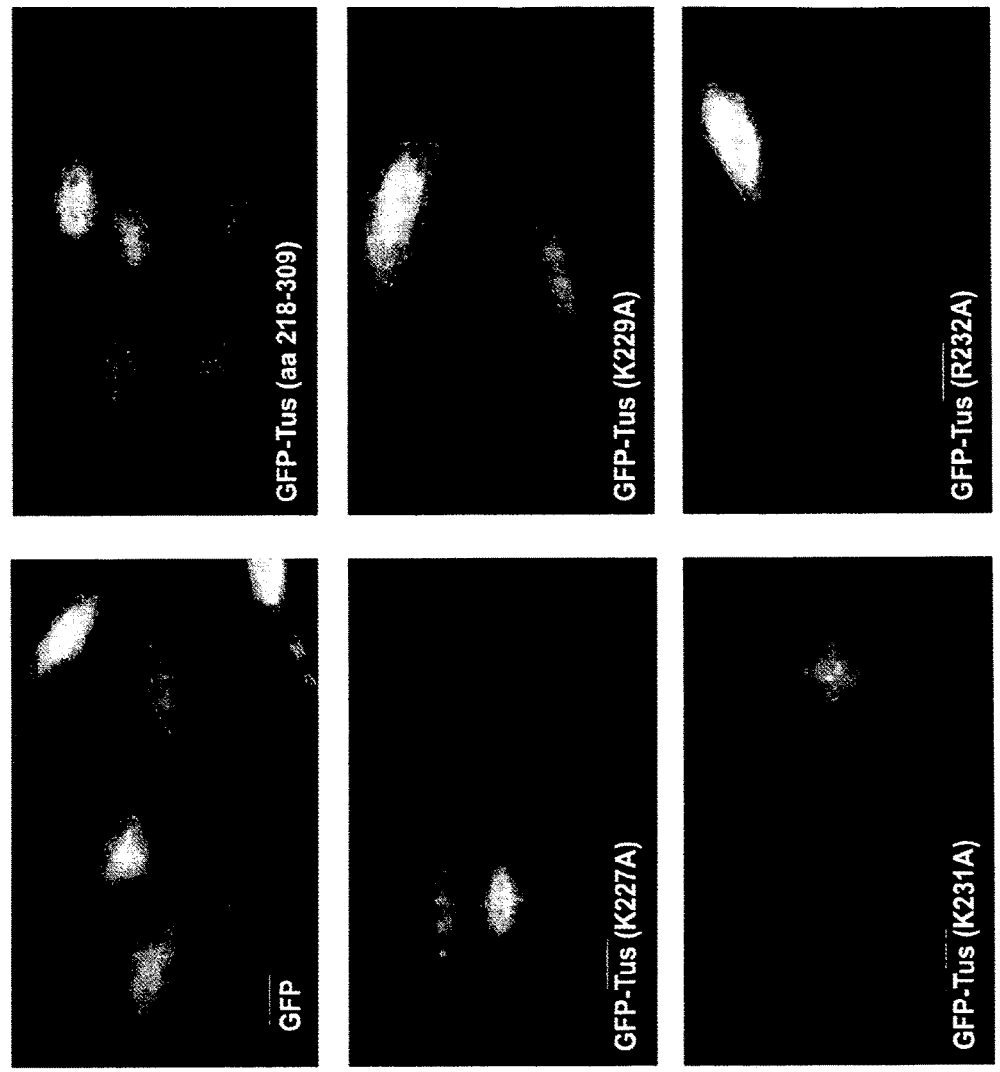
Figures 22B, 23A, 23B:
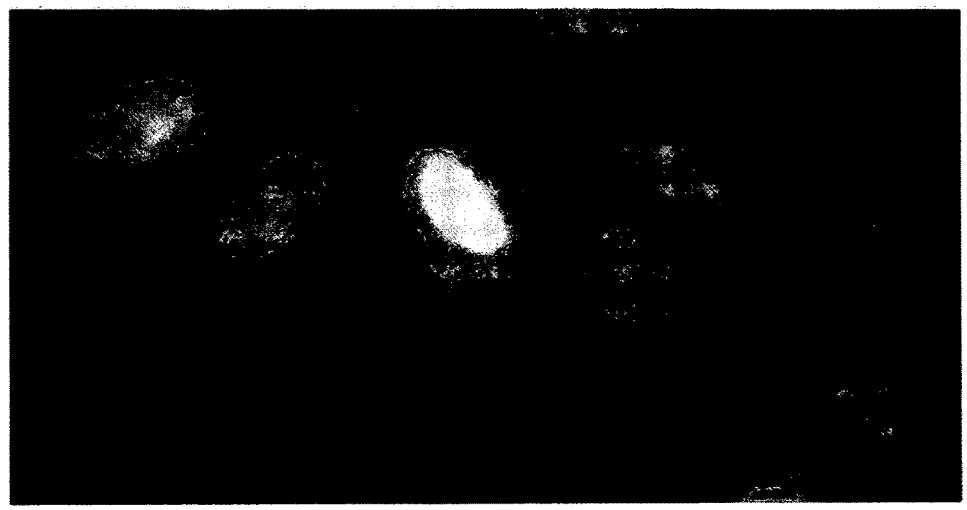

Nuclear localization signals do not fit a tight consensus but generally fall into two classes: short stretches of four to seven basic amino acids (SV40 type; 18); and longer bipartite sequences comprising two stretches of basic amino acids separated by several less conserved spacer amino acids (19). There was no detection of any bipartite-like nuclear localization sequences within amino acids 218 to 264. However, a careful examination of the amino acid sequence revealed a short stretch of basic amino acids resembling an NLS-like sequence of KLKIKRPVK (SEQ ID NO:2) (amino acids 227-235) as shown in FIG. 22B. This sequence might be the putative nuclear targeting signal in Tus. In the crystal structure of Tus, this region is present in the β-strand H, one of the interdomains of Tus protein that forms the main elements of Ter DNA sequence recognition.

Mapping of Nuclear Localization Signal (NLS)

To further demonstrate the importance of the basic amino acids in the putative NLS-like sequence, the basic amino acids were systematically mutated and the subcellular distribution of green fluorescence was examined following transfection into PC3 cells. The construct used for the mutation contains amino acids 218-309 of Tus fused to GFP. As can be seen in FIG. 22A, alteration of any one of the basic amino acids resulted in pronounced perturbation of nuclear targeting of the fusion proteins. These results suggest that each of these basic amino acids play a crucial role in nuclear transport. Finally, we cloned amino acids KLKIKRPVK (SEQ ID NO:2) (amino acids 227 to 235), at the end of GFP and showed that these amino acids are all that is needed for nuclear transport of GFP (FIG. 22B).

It has been proposed that NLS sequences often overlap with the nucleic acid binding domain of proteins (20). It is true that the residues KLKIKRPVK (SEQ ID NO:2) of Tus protein are indeed involved in interacting with ter sequences (8). However, the results show it is very unlikely that the DNA binding activity of Tus is essential for nuclear targeting. Purified GFP fusion protein containing Tus residues 218-309 showed no apparent binding affinity towards Ter (unpublished observation), yet it still localized to the cell nucleus. The loss of Ter binding activity was expected as important amino acids in the interdomain β-strands FG (8) and at other locations in the Tus protein were missing in the deleted construct. Thus, these results suggest that for nuclear targeting the NLS sequence must have basic amino acids but need not bind nucleic acids.

A bacteriophage DNA binding protein, Cre and VirD2 of *Agrobacterium* were shown to possess a putative NLS sequence (16, 21). However, unlike Tus, both Cre and VirD2 have a bipartite-like NLS sequence. There are some other subtle differences with respect to the location of NLS in these two proteins. In VirD2, the NLS is present at the carboxy terminus while in the Cre, the bipartite-like NLS is present at the amino terminus. In VirD2, two regions encompassing 417-420 and 430-434 were needed for NLS function. However, Cre needs two long regions, Region I and Region II, encompassing about 172 (100-271) amino acids for nuclear targeting. Interestingly, Tus only needs a few amino acids for nuclear targeting very similar to most mammalian type NLS sequence. Active nuclear import of proteins is believed to occur in two steps: binding to cytoplasmic surface of the nuclear pore complex followed by the energy dependent translocation into nucleus (9, 14, 22). Experiments are underway to understand the mechanism of nuclear transport in eukaryotic cells mediated by Tus.

Localization of GFP-RFP Hybrid Protein with Tus, Tus NLS and SV40 NLS.

The results presented herein have shown that GFP-Tus fusion protein (approximately 62 kDa) is capable of translocating into the nucleus of PC3 cells. In order to find if a lager protein would be able to translocate into nucleus Tus was cloned at the carboxy terminus of a GFP-RFP fusion protein (total size approximately 90 kDa). Our result suggests that the fusion protein was present all over the cell and no specific nuclear localization was detected (results not shown). Similar results were obtained when full length Tus was replaced with Tus NLS or SV40 NLS (results no shown). It was very surprising that well characterized SV40 NLS was also incapable of nuclear targeting of GFP-RFP fusion. The RFP protein used in this experiment was monomeric. Thus, no multimerization of RFP could be anticipated. Interestingly, similar to Tus NLS, SV40 NLS was capable of targeting GFP only as expected (not shown). It can be concluded, then, that both Tus NLS and a well characterized NLS (SV40) functioned identically when fused to GFP or GFP-RFP. It is possible that GFP-RFP fusion yielded an unusual structure that prevented it from nuclear translocation.

Identification of Nuclear Export Signal (NES)

Figure 20C:
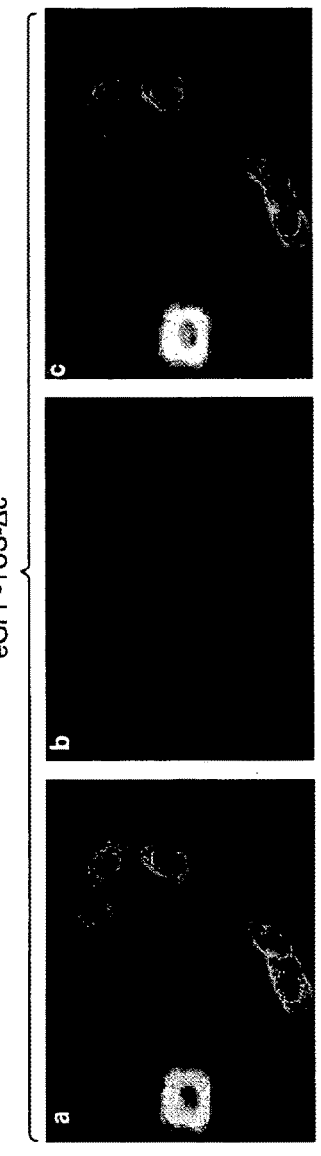

In mapping the NLS region of Tus, it was noticed that deletion of the carboxy terminus (amino acids 218 to 309) caused fluorescence of GFP to concentrate mainly in the cytoplasm (FIG. 20). This result suggested the presence of a nuclear export signal (NES) within the first 217 amino acids of Tus. To narrow down the region required for nuclear export, further deletions were made and the distribution of fluorescence was assessed. As can be seen from the FIG. 21, the NES region is located within the first 77 amino acids of Tus. The primary amino acid sequence of Tus was examined in the first 77 amino acids to determine whether it contains a leucine-rich sequence with hydrophobicity, which is the hallmark criterion established for an NES (13, 20, 23). A possible consensus nuclear export sequence is $LX_{1-3}LX_{2-3}LXL$ (SEQ ID NO: 6), where L=leucine and X=any amino acid and the last leucine can be replaced by conservative substitutions (isoleucine, valine, etc). A careful examination of the Tus amino acids sequence showed the presence of several candidate regions. To localize the NES region, several regions of Tus within the first 77 amino acids were cloned at the carboxy terminus of GFP (FIG. 23A). The clones containing GFP fused with indicated amino acids portion of Tus were transfected into PC3 cell lines and the distribution of GFP was observed. As indicated in the FIG. 23A, the NES was localized within 21 amino acids (amino acids 21 and 41 of Tus). Deletion of leucine residue from either end of 21 amino acids abolished the NES function. It appears that all 21 amino acids seem to be required for NES to function. This region contains several clusters of leucine and other hydrophobic amino acids that are hallmarks of NES (FIG. 23B). Finally, mutation of amino acids L33A and L34A almost completely abolished the function of NES, suggesting the important roles of leucine in NES function (FIG. 23C). However, the length of Tus NES is almost twice the length of other known NES sequences.

Similar to nuclear import, nuclear export is also thought to use the nuclear pore complexes for exporting large proteins (24, 25, 26, 27). However, compared to nuclear import, nuclear export is poorly understood. Some proteins which need to shuttle between the nucleus and cytoplasm through the nuclear pore contain both NLS and NES (26, 27). Examples include the Rev protein of HIV1 and the nuclear factor of activated T cells (NFAT). The Rev protein plays a key role in the regulation of viral expression. NFAT is the target of immunosuppressive drugs widely used in organ transplantation. However, the presence of both NLS and NES in a bacterial protein is unexpected and very unusual as there is no nuclear membrane for protein translocation between nucleus and cytoplasm.

To understand the mechanism of nuclear export of Tus, the effect of leptomycin, an inhibitor of CRM-1 (13, 14) mediated nuclear export, was examined. This result indicates that Tus NES is probably exported through other mechanism unknown to us at this time. It is possible the Tus uses the same mechanism used by two other known proteins, Tax protein of HTLV-1 (28) and Smad3 (29). Both proteins contain similar leucine rich NES for nuclear export as Tus.

NLS and NES are Unique to Tus

It could be argued that given that there may not be any selective pressure against NLS or NES occurring in a bacterial protein, and that basic regions often occur in a DNA binding proteins and leucine-rich sequence often occur in the hydrophobic core of protein, it is not unusual that Tus being a DNA binding protein fortuitously has sequences that function as NLS or NES. As reported before, Cre, a DNA binding protein of P1 bacteriophage, does have a bipartite-like NLS sequence, however, no NES was detected or reported for this protein. To eliminate the possibility that not all DNA binding proteins possess both NLS and NES, a GFP fusion was made with a well characterized bacterial DNA binding protein (TetR) in a similar manner as Tus and distribution of the fusion protein in PC3 cell line was monitored. The results suggest that distribution of the GFP-TetR fusion protein was not localized and similar to unfused GFP protein both fusion proteins were localized in both cytosol and nucleus of the cell (FIG. 23D). Similar results were obtained when lad, another well known DNA binding protein, was fused with GFP (data not shown). These results imply that localized distribution of GFP-Tus fusion was due to the presence of specific signals (NLS or NES) in Tus and not necessarily present in random DNA binding protein.

Example 4

Protein Delivery by Tus and Tus-NLS Functions as PTD

The direct introduction of proteins into cells may be useful to study cell cycle regulation, control of apoptosis and transcription regulation. In addition, protein transduction has been shown to be an effective and safer way of delivering biologically active proteins into cells to correct diseases. The plasma membrane is the natural barrier that excludes proteins among other molecules and seems to be the limiting factor in the development of effective protein delivery systems. Over the years, several proteins including HIV-1 TAT, HSV1-VP22 and *Drosophila*-Antp, and peptides derived from those proteins have been shown to have the capability to travel (or transduce) through plasma membranes (17, 30, 31). All of these proteins and peptides were derived from eukaryotic sources. To date, there has been no example of any bacterial protein(s) that possess similar attributes. Cre, though it contains a putative NLS sequence, has been shown to transduce very poorly unless it was fused to TAT and another NLS sequence (32). The present inventors have found and reported that when purified GFP-Tus fusion protein (61 kDa) is included in the culture media, the fusion protein is internalized very rapidly into PC3 (prostate cancer) human cell line (FIG. 24A). Similarly, fusion protein containing GFP plus 9 amino acid NLS sequence of Tus also has similar cell-penetrating activity and helps transduce the GFP passenger protein from the culture media to inside of PC3 cells in a time dependent manner (FIGS. 24B and C). In contrast, no internalization was observed when equal amount of purified GFP (without NLS) was used under identical conditions. This suggests that Tus-NLS also has the ability to transport proteins inside mammalian cells. Further, there is similar internalization of GFP-Tus or GFP-Tus-NLS fusion proteins into HEK293 cells similar to PC3 cell line (data not shown). Thus, though preliminary, this is the first report on protein delivery using a bacterial protein.

The experiments and results described herein demonstrate the presence of both nuclear targeting (NLS) as well as nuclear exporting (NES) signals in a single bacterial protein, Tus. This may be the first known bacterial protein to contain both signals normally present in some mammalian proteins required for shuttling between nucleus and cytoplasm. Both NLS and NES contain putative consensus-like sequences. The results presented herein suggest that Tus indeed contains a putative NLS signal and that mutations of essential amino acids in this sequence completely abolished nuclear targeting. NLS sequences often overlap with DNA binding regions. Although the putative NLS region identified in Tus contains some DNA (Ter) binding amino acids, the results presented here have shown that DNA binding is not essential for nuclear targeting. In addition, when other well characterized DNA binding proteins, LacI and TetR, were fused GFP in a similar manner as Tus, they failed to show any preferential localization (nuclear or cytoplasmic). This suggests that Tus is a unique protein to have both nuclear importing and exporting signals.

It is also noteworthy that full-length Tus fused to GFP directs mostly in the nucleus, suggesting that the NLS is a dominant signal compared to NES.

A Blast search (NCBI GCG-Lite plus parallel Fasta search for protein sequence), has shown that 21-amino acids NES of Tus has sequence identity of about 83% with both human and mouse transcription factor (E2F6) and about 75% identity with human and mouse nuclear factor of kappa light polypeptide gene enhancer in B-cells 2 (NFKb2) and *Drosophila* DNA polymerase subunit a B. In addition, it has various level of identity with many more human and other mammalian proteins.

In addition to the discovery of NLS and NES in Tus protein, the results and experiments suggest that full length Tus and its 9 residue NLS peptides may be useful for protein delivery into mammalian cells. GFP fused to either full length or its NLS is capable of internalization in PC3 or 293 cells within 2 hrs after the addition of fusion proteins. This is the first example of a bacterial protein-mediated protein delivery into mammalian cells and may added to the list of known mammalian proteins with similar attributes.

Methods

The foregoing experiments were performed with, but not limited to, the following methods and materials.

Packaging of VLPs

The 293T cell line was used as packaging cells for VLPs generation: $3.3 \times 10^6$ cells were plated in 10 cm dish (10 ml of DMEM containing 10% FBS were plated 24 hr before transfection). At day of transfection fresh culture medium was added to cells and 2 hr later transfection reagent (DNA and FuGene 6 (Roche™)) was added to cells according to manufacturer instructions. Each dish was transfected with total of 15 ug of DNA. GAG-Cre transfection conditions consisted of 9 ug of pCMV-GAG-Cre plasmid and 6 ug of ssDNA (as filler DNA), GAG-Cre+VSV-G conditions received 9 ug of pCMV-GAG-Cre plasmid, 5 ug of pCMV-VSV-G plasmid and 1 ug ssDNA, and GAG-Cre+VSV-G+GAG-PR conditions received 9 ug of pCMV-GAG-Cre plasmid, 5 ug of pCMV-VSV-G plasmid and 1 ug of pCMV-GAG-PR plasmid. The supernatants were collected 64 hr p/t. The supernatants were clarified by centrifugation at 3000 rpm for 10 min at 40 C. Clarified supernatants were treated with DNAse 1 at 10 units/ml for a period of 30 min at RT then filtered through 0.45 um filter. The generated VLPs were used for immediate transduction or were stored at −80 C.

Transduction of PC3-Lox1-gfp-Lox2-RFP reporter cell line. The PC3 reporter cell line consisting of stable integrated CMV-Lox1-GFP-Lox2 RFP expression cassette ($1 \times 10^5$ cell per well in 2 ml of complete culture medium (DMEM+10% FCS) in 6 well plate) was transduced with 1 ml of VLPs corresponding to each of the experimental conditions. 72 hr post transduction, data was collected using fluorescence microscopy.

Plasmid constructions. All DNA manipulations were performed using standard procedures. The wild type Tus protein gene was cloned from the *E. coli* chromosome by PCR using the primers, 5'-ATT TTA GCTAGC GGA GGT GCG CGT TAC GAT CTC GTA GAC CGA CTC-3' (SEQ ID NO: 7) (oligo 1) and 5'-TAT ATT CAATTG TTA ATC TGC AAC ATA CAG GTG CAG CCG TG-3' (SEQ ID NO:8) (oligo 2) containing NheI and MunI restriction enzyme sites (underlined), respectively. The PCR product was cloned into a derivative of a Gateway destination vector, pDest 47, (Invitrogen) at the NheI-MunI sites and designated pDest 472-Tus. GFP was cloned into this vector by site-specific recombination using Gateway (Invitrogen) cloning technology. The final expression vector containing GFP-Tus fusion was under a strong CMV promoter. The entire fusion construct was verified by sequencing. The plasmid is called pDest GFP-Tus.

Amino terminal deletion derivatives of Tus protein were cloned by replacing the full-length Tus from pDest 472-GFP-Tus with PCR fragments. To clone amino acids 217 to 309 and 264 to 309 of Tus at the end of GFP, oligos 5'-ATA TTT GCTAGC GAT ATC GCT GCC CTG CCA CAG AAC-3' (SEQ ID NO:9) and 5'-ATA TT T GCTAGC ATT AAT CGG GAT AAT GGC GC-3' (SEQ ID NO:10), respectively were used with oligo 2 above as the 3' oligo for PCR. The restriction site NheI is underlined. For carboxy terminal end deletions, oligo 1 (above) was used in conjunction with the following oligos: 5'-ATA ATA CAATTG TTA TAA ATG GCG GAA ATG ACG CAA CGC-3' (SEQ ID NO11) (amino acids 1-77), 5'-ATA ATA <u>CAATTG</u> TTA GAG TTC TGA TTC AAC CGT GAC G-3' (SEQ ID NO:12) (amino acids 1-133), 5'-ATA ATA <u>CAATTG</u> TTA TGA TTT CAG GCT TTT TTC CAG CTG TG-3' (SEQ ID NO:13) (amino acids 1-195). The PCR fragments were cloned at NheI and MunI sites of pDest 472-GFP-Tus to replace the full-length Tus. All clones were sequence verified. To clone amino acids 1-217 of Tus, the plasmid pDest 472-GFP-Tus was cut with EcoRV and MunI, filled in with Klenow fragment and the largest fragment was self-ligated.

To clone the NLS of Tus, the following oligos were used:

```
                                              (SEQ ID NO: 14)
5'-CTAGCAAGTTAAAAATCAAACGTCCGGTGAAGTAATAAC-3'
and
                                              (SEQ ID NO: 15)
5'-AATTGTTATTACTTCACCGGACGTTTGATTTTTAACTTG-3'.
```

The underlined bases are complementary to NheI and MunI restriction sites following digestion. The oligos were annealed using standard procedures and ligated to pDest GFP-Tus digested with NheI and MunI. This replaced the full length Tus with the NLS sequence.

Several GFP-RFP fusions have been generated in order to determine if Tus, Tus NLS or SV40 NLS (AVPKKKRKV) (SEQ ID NO:16) would be capable to transporting the fusion protein into the nucleus. To clone Tus, Tus NLS and SV40NLS oligos were designed and cloned as EcoRI and BamHI fragments at the C-end of GFP-RFP. Clones were sequenced and confirmed. The plasmids, GFP-RFP-Tus, GFP-RFP-Tus NLS and GFP-RFP-SV40 NLS, were purified and PC3 cells were transfected by standard procedure (see below).

Mutation of Tus Proteins. Mutation of Tus was done using the QUICK CHANGE procedure developed by Stratagene (California). To change the amino acid K277 to A227 (K227A), the oligos used were 5'-GCTGCCCTGCCACA-GAACGC<u>AGCGCT</u>AAAAATCAAA CGTCCGGTG3' (SEQ ID NO:17) (top oligo) and 5'-CACCGGACGTTT-GATTTTT<u>AGCGCT</u> GCGTTCTGTGGCAGGGCA-GC-3' (SEQ ID NO:18) (bottom oligo), a restriction site, AfeI (underlined) was created to screen the mutants. For K229A mutation, the oligos were 5'-GCCCTGCCACAGAACGC-GAA<u>GCTAGC</u>AATCAAACGTCCG-GTGAAG-3' (SEQ ID NO:19) (top oligo) and 5'-CTTCACCGGACGTTT-GATT<u>GCTAGC</u>TTCGCGTTCTGTGGCAG GGC-3' (SEQ ID NO:20) (bottom oligo), a restriction site NheI (underlined) was created to screen mutants. For K231A, the oligos used were 5'-CAGAACGCGAAGTTAAAAATC <u>GCGCGC</u>CCGGTGAAGGTGCAGCCG-3' (SEQ ID NO:21) (top oligo) and 5'-CGGCTGC ACCTTCACCGG <u>GCGCGC</u>GATTTTTAACTTCGCGTTCTG-3' (SEQ ID NO:22) (bottom oligo), a restriction enzyme BssHII site (underlined) was created for screening mutants. For R232A mutation the following oligos were used, 5'-CAGAACGC-GAAGTTAAAAATCAA<u>GGCGCC</u>GGTGAAGGTGCA-GCCG-3' (SEQ ID NO:23) (top) and 5'-CGGCTGCACCT-TCACC<u>GGCGCC</u>TTGATTTTTAACTTCGCGTTCTG-3' (SEQ ID NO:24), a restriction site, KasI (underlined) was created for easy screening. All mutations and clones were verified by DNA sequencing.

Cell culture, transfection and microscopy. A human prostate carcinoma cell line PC-3 was cultured in DMEM (Invitrogen) supplemented with 10% FCS and antibiotics. Cells were plated 24 hr before transfection at $10^6$ cells per well (in six well culture dishes) in a final volume of 2 ml of complete culture medium. The following day, 2 hr before transfection, culture medium was replaced with 2 ml of fresh complete culture medium. Plasmids coding for GFP-Tus fusion proteins were diluted at 2 μg/10 μl in TE buffer and used for transfection using FuGene-6 transfection reagent (Roche Biochemicals).

After transfection (24 hr) gene expression was monitored using a set of fluorescence filters specific for eGFP detection using ZEISS fluorescence microscopy. Images were archived using SPOT-2 image camera.

Delivery of TUS-GFP fusion protein into PC3 cells. The PC3 cells were plated at $1\times10^5$ per well in 6-well in tissue culture plates 24 hr before transfection. Next day, culture medium was replaced with 2 ml of fresh medium containing 7.5 μg Tus-GFP or Tus-GFP-NLS protein to each well. For control experiments, the cells were treated with the same amount of GFP (without NLS). At indicated time points, cells were washed in PBS and the green fluorescence was observed under fluorescence microscopy.

DAPI staining. Plates containing adherent cells were washed with PBS and fresh PBS supplemented with DAPI at 1:1000 dilution of stock solution (1 m/mL) was added to plates and plates were incubated for 10 min in tissue culture incubator. After this time plates were washed again with PBS and fresh complete culture medium was added. The blue fluorescence was detected under fluorescence microscopy using DAPI filter.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

REFERENCES

1. Masters, M., and Broda, P. (1971). Evidence for the bidirectional replication of the *Escherichia coli* chromosome. Nat New Biol. 232:137-40.
2. Kuempel, P. L., Maglothin, P., and Prescott, D. M. (1973). Bidirectional termination of chromosome replication in *Escherichia coli*. Mol Gen Genet. 125:1-8.
3. Coskun-Ari, F. F., and Hill, T. (1997). Sequence-specific interactions in the Tus-Ter complex and the effect of base pair substitutions on arrest of DNA replication in *Escherichia coli*. J. Biol. Chem., 272: 26448-24456.
4. Neylon, C., Kralicek, A, V., Hill, T. M and Dixon, N. E. (2005). Replication termination in *Escherichia coli*: structure and antihelicase activity of the Tus-Ter complex. Micro. Mol. Biol. Rev., 69: 501-526.
5. Gottlieb, P. A., Wu, S., Zhang, X., Tecklenburg, M., Kuempel, P., and Hill, T. (1992). Equilibrium, kinetic, and footprinting studies of the Tus-Ter protein-DNA interaction. J. Biol. Chem., 267: 7434-7443.
6. Neylon, C., Brown, S. E., Kralicek, A. V., Miles, C. S., Love, C. A and Dixon, N. E. (2000). Interaction of the *Escherichia coli* replication terminator protein (Tus) with DNA: a model derived from DNA-binding studies of mutant proteins by surface plasmon resonance. Biochemistry, 39: 11989-11999.
7. Skokotas, A., Hiasa, H., Marians, K. J., O'Donnell, L., and Hill, T. (1995). Mutations in the *Escherichia coli* Tus protein define a domain positioned close to the DNA in the Tus-Ter complex. J. Biol. Chem., 270: 30941-30948.
8. Kamada K., Horiuchi, T., Ohsumi, K., Shimamoto, N. and Morikawa, K. (1996). Structure of a replication-terminator protein complexed with DNA. Nature, 383: 598-603.
9. Mulugu, S., Potnis, A., Shamsuzzaman, Taylor, J., Alexander, K., and Bastia, D. (2001). Mechanism of termination of DNA replication of *Escherichia coli* involves helicase-contrahelicase interaction. Proc Natl Acad Sci USA. 98:9569-74.
10. Richardson, W. D., Mills, A. D., Dilworth, S. M., Laskey, R. A., Dingwall, C. (1988). Nuclear protein migration involves two steps: rapid binding at the nuclear envelope followed by slower translocation through nuclear pores. Cell, 52: 655-664.
11. Jans, D. A., Xiao, C. Y. and Lam, M. H. (2000). Nuclear targeting signal recognition: a key control point in nuclear transport? Bioessays, 22: 532-544.
12. Patel, S. S., Belmont., B. J, Sante., J. M., and Rexach, M. F. (2007). Natively unfolded nucleoporins gate protein diffusion across the nuclear pore complex. Cell, 129: 83-96.
13. Fischer, U., J. Huber, W. C. Boelens, I. W. Mattaj, and R. Luhrmann. (1995). The HIV-1 Rev activation domain is a nuclear export signal that accesses an export pathway used by specific cellular RNAs. Cell 82:475-483.
14. Fornerod, M., M. Ohno, M. Yoshida, and I. W. Mattaj. (1997). CRM1 is an export receptor for leucine-rich nuclear export signals. Cell 90:1051-1060.
15. Gangeten, S., Le, Y., Miller, J., and Sauer, B. (1997). Brief expression of a GFP Cre fusion gene in embryonic stem cells allows rapid retrieval of site-specific genomic deletions. Nucleic Acids Res., 25: 3326-3331.
16. Pelczar, P., Kalck, V., Gomez, D. and Hohn, B. (2004). *Agrobacterium* protein VirD2 and VirE2 mediate precise integration of synthetic T-DNA complexes in mammalian cells. EMBO reports. 5: 632-637.
17. Chauhan, A., Tikoo. A., Kapur, A. K., and Singh, M. The taming of the cell penetrating domain of HIV Tat: Myths and realities. (2007). J. Control. Release, 117: 148-162.
18. Kalderon, D., Roberts, B. L., Richardson, W. D., and Smith, A. E. (1984). A short amino acid sequence able to specify nuclear location. Cell, 39: 499-509.
19. Robbins, J., Dilworth, S. M., Laskey, R. A., and Dingwall, C. (1991). Two interdependent basic domains in nucleoplasmin nuclear targeting sequence: identification of a class of bipartite nuclear targeting sequence. Cell, 64: 615-623.
20. Bogerd, H. P., Fridell, R. A., Benson, R. E., Hua, J., and Cullen, B. R. (1996). Protein sequence requirements for function of the human T-cell leukemia virus type 1 Rex nuclear export signal delineated by a novel in vivo randomization-selection assay. Mol. Cell. Biol., 16: 4207-4214.
21. Le, Y., Gagneten, S., Tombaccini, D., Bethke, B., Sauer, B. (1999). Nuclear targeting determinants of the phage P1 Cre DNA recombinase. Nucleic Acids Res., 27: 4703-4709.
22. Newmeyer, D. D., and Forbes, D. J. (1988). Nuclear import can be separated into distinct steps in vitro: nuclear pore binding and translocation. Cell, 52: 641-653.
23. Ikuta, T., Eguchi, H., Tachibana, T., Yoneda, Y., and Kawajiri, K. (1998). Nuclear localization and export signals of the human aryl hydrocarbon receptor. J Biol. Chem., 273: 2895-2904.
24. Cyert, M. S. (2001). Regulation of nuclear localization during signaling. J. Biol. Chem., 276: 20805-20808.
25. Dworetzky, S. I., and Fledherr, C. M. (1988). Translocation of RNA-coated gold particles through the nuclear pores of oocytes. J. Cell. Biol., 106: 575-584.
26. Gerace, L. (1995). Nuclear export signals and the fast track to the cytoplasm. Cell, 82: 341-344.
27. Gorlich, D., and Mattaj, I. W. (1996). Nucleocytoplasmic transport. Science, 271: 1513-1518.
28. Alefantis, T., Barmak, K., Harhaj, E. W., Grant, C. and Wigdahl, B. (2003). Characterization of a nuclear export signal within the HTLV-1 transactivator protein Tax. J. Biol. Chem., 278: 21814-21822.
29. Kurisaki, A., Kurisaki, K., Kowanetz, M., Sugino, H., Yoneda, Y., Heldin. C.-H., Moustakas. (2006). The mechanism of nuclear export of Smad3 involves Exportin 4 and Ran. Mol. Cell. Biol, 26:1318-1332.
30. Schwarze, S. R., Hruska, K. A., and Dowdy, S. F. (2000). Protein transduction: unrestricted delivery into all cells? Trends Cell. Biol, 10: 290-295.
31. Murriel, C. L., and Dowdy, S. F. (2006). Influence of protein transduction domains on intracellular delivery of macromolecules. Expert Opin. Drug Deliv. 3: 739-746.
32. Peitz, M., Pfannkuche, K., Rajewsky., K and Edenhofer, F. (2002). Ability of the hydrophobic FGF and basic TAT peptides to promote cellular uptake of recombinant Cre recombinase: a tool for efficient genetic engineering of mammalian genomes. Proc. Natl. Acad. Sci. 99: 4489-4494.

What is claimed is:

1. A VLP comprising:
   a Gag fusion protein comprising a matrix protein, a capsid protein, a nucleocapsid protein, covalently linked to a protein of interest selected from the group consisting of a cytotoxic enzyme, an interferon, a tumor suppressor, a recombinase, a hormone, and a stem cell transcription factor;
   a fusogenic protein having reduced ligand-binding activity; and
   a nuclear localization signal (NLS) comprising at least a portion of SEQ ID NO: 1 or SEQ ID NO: 2.

2. The VLP of claim 1, wherein the fusogenic protein is selected from the group consisting of: an influenza haemagglutinin, a respiratory syncytial virus fusion protein, a tick borne encephalitis virus or dengue fever virus E protein, a Semliki Forest virus E1 protein, a rabies virus or vesicular stomatitis virus (VSV) G protein, a baculovirus gp64, and fragments thereof.

3. The VLP of claim 1, wherein the NLS consists of SEQ ID NO: 1.

4. The VLP of claim 1, wherein the NLS consists of SEQ ID NO: 2.

5. The VLP of claim 1, wherein the Gag fusion protein does not comprise a reverse transcriptase, a protease, or an integrase.

6. The VLP of claim 1, further comprising a second Gag fusion protein comprising a protease.

7. The VLP of claim 1, wherein the fusogenic protein is an envelope glycoprotein or fragment thereof.

8. The VLP of claim 7, wherein the envelope glycoprotein is from a RNA virus or a retrovirus.

9. The VLP of claim 1, wherein the fusogenic protein is a VSV-G glycoprotein comprising a substitution at the second amino acid of (phenylalanine (F)) for cysteine (C) of the mature VSV-G protein.

10. A method of targeting one or more proteins to a cell, comprising contacting a cell with a VLP comprising:
    a Gag fusion protein comprising a matrix protein, a capsid protein, a nucleocapsid protein, covalently linked to a protein of interest selected from the group consisting of a cytotoxic enzyme, an interferon, a tumor suppressor, a recombinase, a hormone, and a stem cell transcription factor;
    a fusogenic protein having reduced ligand-binding activity; and,
    a nuclear localization signal comprising at least a portion of SEQ ID NO: 1 or SEQ ID NO: 2,
    thereby targeting one or more proteins to the cell.

11. The method of claim 10, wherein the fusogenic protein is selected from the group consisting of: an influenza haemagglutinin, a respiratory syncytial virus fusion protein, a tick borne encephalitis virus or dengue fever virus E protein, a Semliki Forest virus E1 protein, a rabies virus or vesicular stomatitis virus (VSV) G protein, a baculovirus gp64, and fragments thereof.

12. The method of claim 10, wherein the nuclear localization signal consists of SEQ ID NO: 1.

13. The method of claim 10, wherein the nuclear localization signal consists of SEQ ID NO: 2.

14. The method of claim 10, wherein the Gag fusion protein does not comprise a reverse transcriptase, a protease, or an integrase.

15. The method of claim 10, further comprising a second Gag fusion protein comprising a protease.

16. A method of providing protein therapy to a target cell, comprising contacting the cell with a VLP comprising:
 a Gag fusion protein comprising a matrix protein, a capsid protein, a nucleocapsid protein, covalently linked to a protein of interest selected from the group consisting of a cytotoxic enzyme, an interferon, a tumor suppressor, a recombinase, a hormone, and a stem cell transcription factor;
 a fusogenic protein having reduced ligand-binding activity; and,
 a nuclear localization signal comprising at least a portion of SEQ ID NO: 1 or SEQ ID NO: 2,
 thereby providing protein therapy to the target cell.

17. The method of claim 16, wherein the nuclear localization signal consists of SEQ ID NO: 1.

18. The method of claim 16, wherein the nuclear localization signal consists of SEQ ID NO: 2.

19. The method of claim 16, wherein the Gag fusion protein does not comprise a reverse transcriptase, a protease, or an integrase.

20. The method of claim 16, further comprising a second Gag fusion protein comprising a protease.

\* \* \* \* \*

SEQUENCE LISTING

```
<160> NUMBER OF SEQ ID NOS: 29

<210> SEQ ID NO 1
<211> LENGTH: 309
<212> TYPE: PRT
<213> ORGANISM: Escherichia coli

<400> SEQUENCE: 1

Met Ala Arg Tyr Asp Leu Val Asp Arg Leu Asn Thr Thr Phe Arg Gln
1               5                   10                  15

Met Glu Gln Glu Leu Ala Ile Phe Ala Ala His Leu Glu Gln His Lys
            20                  25                  30
```

```
Leu Leu Val Ala Arg Val Phe Ser Leu Pro Glu Val Lys Glu Asp
            35                  40                  45
Glu His Asn Pro Leu Asn Arg Ile Glu Val Lys Gln His Leu Gly Asn
 50                  55                  60
Asp Ala Gln Ser Leu Ala Leu Arg His Phe Arg His Leu Phe Ile Gln
 65                  70                  75                  80
Gln Gln Ser Glu Asn Arg Ser Ser Lys Ala Ala Val Arg Leu Pro Gly
                 85                  90                  95
Val Leu Cys Tyr Gln Val Asp Asn Leu Ser Gln Ala Ala Leu Val Ser
            100                 105                 110
His Ile Gln His Ile Asn Lys Leu Lys Thr Thr Phe Glu His Ile Val
            115                 120                 125
Thr Val Glu Ser Glu Leu Pro Thr Ala Ala Arg Phe Glu Trp Val His
130                 135                 140
Arg His Leu Pro Gly Leu Ile Thr Leu Asn Ala Tyr Arg Thr Leu Thr
145                 150                 155                 160
Val Leu His Asp Pro Ala Thr Leu Arg Phe Gly Trp Ala Asn Lys His
                165                 170                 175
Ile Ile Lys Asn Leu His Arg Asp Glu Val Leu Ala Gln Leu Glu Lys
            180                 185                 190
Ser Leu Lys Ser Pro Arg Ser Val Ala Pro Trp Thr Arg Glu Glu Trp
        195                 200                 205
Gln Arg Lys Leu Glu Arg Glu Tyr Gln Asp Ile Ala Ala Leu Pro Gln
    210                 215                 220
Asn Ala Lys Leu Lys Ile Lys Arg Pro Val Lys Val Gln Pro Ile Ala
225                 230                 235                 240
Arg Val Trp Tyr Lys Gly Asp Gln Lys Gln Val Gln His Ala Cys Pro
                245                 250                 255
Thr Pro Leu Ile Ala Leu Ile Asn Arg Asp Asn Gly Ala Gly Val Pro
            260                 265                 270
Asp Val Gly Glu Leu Leu Asn Tyr Asp Ala Asp Asn Val Gln His Arg
        275                 280                 285
Tyr Lys Pro Gln Ala Gln Pro Leu Arg Leu Ile Ile Pro Arg Leu His
    290                 295                 300
Leu Tyr Val Ala Asp
305

<210> SEQ ID NO 2
<211> LENGTH: 9
<212> TYPE: PRT
<213> ORGANISM: Escherichia coli

<400> SEQUENCE: 2

Lys Leu Lys Ile Lys Arg Pro Val Lys
1               5

<210> SEQ ID NO 3
<211> LENGTH: 21
<212> TYPE: PRT
<213> ORGANISM: Escherichia coli

<400> SEQUENCE: 3

Leu Ala Ile Phe Ala Ala His Leu Glu Gln His Lys Leu Leu Val Ala
1               5                   10                  15

Arg Val Phe Ser Leu
            20
```

```
<210> SEQ ID NO 4
<211> LENGTH: 22
<212> TYPE: PRT
<213> ORGANISM: Vesicular stomatitis virus

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe
            20

<210> SEQ ID NO 5
<211> LENGTH: 22
<212> TYPE: PRT
<213> ORGANISM: Vesicular stomatitis virus

<400> SEQUENCE: 5

Met Lys Cys Leu Leu Tyr Leu Ala Phe Leu Phe Ile Gly Val Asn Cys
1               5                   10                  15

Lys Cys Thr Ile Val Phe
            20

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: misc_feature
<222> LOCATION: (2)..(4)
<223> OTHER INFORMATION: This region may encompass 1 to 3 residues
<220> FEATURE:
<221> NAME/KEY: MOD_RES
<222> LOCATION: (6)..(8)
<223> OTHER INFORMATION: Any amino acid
<220> FEATURE:
<221> NAME/KEY: misc_feature
<222> LOCATION: (6)..(8)
<223> OTHER INFORMATION: This region may encompass 2 to 3 residues
<220> FEATURE:
<221> NAME/KEY: MOD_RES
<222> LOCATION: (10)..(10)
<223> OTHER INFORMATION: Any amino acid
<220> FEATURE:
<221> NAME/KEY: misc_feature
<222> LOCATION: (1)..(11)
<223> OTHER INFORMATION: see specification as filed for detailed
      description of substitutions and preferred embodiments

<400> SEQUENCE: 6

Leu Xaa Xaa Xaa Leu Xaa Xaa Xaa Leu Xaa Leu
1               5                   10

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
attttagcta gcggaggtgc gcgttacgat ctcgtagacc gactc           45
```

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tatattcaat tgttaatctg caacatacag gtgcagccgt g         41

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atatttgcta gcgatatcgc tgccctgcca cagaac              36

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atatttgcta gcattaatcg ggataatggc gc                  32

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ataatacaat tgttataaat ggcggaaatg acgcaacgc           39

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ataatacaat tgttagagtt ctgattcaac cgtgacg             37

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ataatacaat tgttatgatt tcaggctttt ttccagctgt g        41

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctagcaagtt aaaaatcaaa cgtccggtga agtaataac                              39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aattgttatt acttcaccgg acgtttgatt tttaacttg                              39

<210> SEQ ID NO 16
<211> LENGTH: 9
<212> TYPE: PRT
<213> ORGANISM: Simian virus

<400> SEQUENCE: 16

Ala Val Pro Lys Lys Lys Arg Lys Val
1               5

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gctgccctgc cacagaacgc agcgctaaaa atcaaacgtc cggtg                       45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caccggacgt ttgatttta gcgctgcgtt ctgtggcagg gcagc                        45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gccctgccac agaacgcgaa gctagcaatc aaacgtccgg tgaag                       45

<210> SEQ ID NO 20
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttcaccgga cgtttgattg ctagcttcgc gttctgtggc agggc              45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagaacgcga agttaaaaat cgcgcgcccg gtgaaggtgc agccg              45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cggctgcacc ttcaccgggc gcgcgatttt aacttcgcg ttctg               45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cagaacgcga agttaaaaat caaggcgccg gtgaaggtgc agccg              45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggctgcacc ttcaccggcg ccttgatttt aacttcgcg ttctg               45

<210> SEQ ID NO 25
<211> LENGTH: 6
<212> TYPE: PRT
<213> ORGANISM: Simian virus

<400> SEQUENCE: 25

Pro Lys Lys Arg Lys Val
1               5

<210> SEQ ID NO 26
<211> LENGTH: 9
<212> TYPE: PRT
<213> ORGANISM: Unknown
<220> FEATURE:
```

```
-continued

<223> OTHER INFORMATION: Description of Unknown: C-Myc-type
      peptide

<400> SEQUENCE: 26

Pro Ala Ala Lys Arg Val Lys Leu Asp
1               5

<210> SEQ ID NO 27
<211> LENGTH: 11
<212> TYPE: PRT
<213> ORGANISM: Human immunodeficiency virus

<400> SEQUENCE: 27

Leu Gln Leu Pro Pro Leu Glu Arg Leu Thr Leu
1               5                   10

<210> SEQ ID NO 28
<211> LENGTH: 11
<212> TYPE: PRT
<213> ORGANISM: Unknown
<220> FEATURE:
<223> OTHER INFORMATION: Description of Unknown: Protein
      kinase inhibitor peptide

<400> SEQUENCE: 28

Leu Ala Leu Lys Leu Ala Gly Leu Asp Ile Asn
1               5                   10

<210> SEQ ID NO 29
<211> LENGTH: 12
<212> TYPE: PRT
<213> ORGANISM: Homo sapiens

<400> SEQUENCE: 29

Met Phe Arg Glu Leu Asn Glu Ala Leu Glu Leu Lys
1               5                   10
```